United States Patent
Herschkowitz et al.

(10) Patent No.: US 11,776,675 B2
(45) Date of Patent: Oct. 3, 2023

(54) SYSTEMS FOR TRACKING MEDICATIONS

(71) Applicant: Above the Fold, LLC, Brooklyn, NY (US)

(72) Inventors: Samuel Herschkowitz, Brooklyn, NY (US); Abby Herzig, Brooklyn, NY (US); Joshua Kornberg, Brooklyn, NY (US); Seymour Fein, New City, NY (US); Deborah Adler, New York, NY (US); Eric Freitag, Brooklyn, NY (US); Robert R. Pascazio, New York, NY (US); Matthew Chin, New York, NY (US); Gareth Brown, Jersey City, NJ (US); Stephen Kaes, New York, NY (US); Troy Yoshimoto, Brooklyn, NY (US); Ritik Dholakia, Brooklyn, NY (US); Mike Klodginski, Brooklyn, NY (US); Khoi Uong, Brooklyn, NY (US); Erin Woo, Brooklyn, NY (US); Pepin Gelardi, Brooklyn, NY (US); Theodore Ullrich, New York, NY (US)

(73) Assignee: Above the Fold, LLC, Brooklyn, NY (US)

( * ) Notice: Subject to any disclaimer, the term of this patent is extended or adjusted under 35 U.S.C. 154(b) by 0 days.

(21) Appl. No.: 16/880,039

(22) Filed: May 21, 2020

(65) Prior Publication Data
US 2022/0392601 A1    Dec. 8, 2022

Related U.S. Application Data

(63) Continuation of application No. 16/181,123, filed on Nov. 5, 2018, now Pat. No. 10,699,539, which is a
(Continued)

(51) Int. Cl.
*G16H 20/17* (2018.01)
*G08B 21/02* (2006.01)
(Continued)

(52) U.S. Cl.
CPC .......... *G16H 20/17* (2018.01); *A61B 5/0002* (2013.01); *A61B 5/0022* (2013.01);
(Continued)

(58) Field of Classification Search
CPC ........ G16H 20/17; G16H 20/10; G16H 40/67; G16H 50/70; A61B 5/0002; A61B 5/0022;
(Continued)

(56) References Cited

U.S. PATENT DOCUMENTS

| 4,731,765 A | 3/1988 | Cole et al. |
| 5,973,121 A | 10/1999 | Burks, Jr. et al. |

(Continued)

FOREIGN PATENT DOCUMENTS

| CA | 2 786 885 A1 | 2/2014 |
| GB | 2 446 987 | 8/2008 |

(Continued)

OTHER PUBLICATIONS

International Search Report and Written Opinion issued (dated Apr. 28, 2017) in corresponding International Application No. PCT/US2017/018222.
(Continued)

*Primary Examiner* — Omar Casillashernandez
(74) *Attorney, Agent, or Firm* — Jon E. Gordon; Haug Partners LLP

(57) ABSTRACT

The present disclosure relates to integrated systems, methods and apparatuses for assisting individuals in managing acute life-threatening conditions. A system in accordance with the current disclosure may comprise an electronic
(Continued)

circuit configured to be attached to a container of a medication and one or more devices in communication with the electronic circuit in a private network. In an aspect, the one or more devices may work in concert to determine the safety level of an individual based on predetermined usage settings. In some aspects, the system may be configured to determine whether a medication would expire before its manufactured expiry date. In another aspect, the system may assist an individual in locating a medication. In a further aspect, the system may determine whether an individual is having an anaphylactic reaction. In some aspects, the system may detect a known allergen and alert the individual.

4 Claims, 64 Drawing Sheets

Related U.S. Application Data continuation of application No. 15/435,145, filed on Feb. 16, 2017, now Pat. No. 10,163,311.

(60) Provisional application No. 62/295,973, filed on Feb. 16, 2016.

(51) Int. Cl.
*H04W 64/00* (2009.01)
*G08B 21/18* (2006.01)
*A61B 5/00* (2006.01)
*H04W 76/10* (2018.01)
*G08B 25/00* (2006.01)
*G08B 25/01* (2006.01)
*G16H 20/10* (2018.01)
*G16H 40/67* (2018.01)
*G08B 7/06* (2006.01)
*H04W 88/08* (2009.01)
*H04W 4/80* (2018.01)
*A61M 5/20* (2006.01)
*A61M 15/00* (2006.01)
*G16H 50/70* (2018.01)

(52) U.S. Cl.
CPC .......... *A61B 5/4833* (2013.01); *A61B 5/6824* (2013.01); *A61B 5/6898* (2013.01); *A61B 5/7405* (2013.01); *A61B 5/7455* (2013.01); *G08B 7/06* (2013.01); *G08B 21/0272* (2013.01); *G08B 21/0277* (2013.01); *G08B 21/0288* (2013.01); *G08B 21/182* (2013.01); *G08B 25/001* (2013.01); *G08B 25/016* (2013.01); *G16H 20/10* (2018.01); *G16H 40/67* (2018.01); *H04W 64/00* (2013.01); *H04W 76/10* (2018.02); *A61M 5/20* (2013.01); *A61M 15/00* (2013.01); *A61M 2205/18* (2013.01); *A61M 2205/3368* (2013.01); *A61M 2205/3569* (2013.01); *A61M 2205/3592* (2013.01); *A61M 2205/50* (2013.01); *A61M 2205/505* (2013.01); *A61M 2205/52* (2013.01); *A61M 2205/581* (2013.01); *A61M 2205/587* (2013.01); *A61M 2209/086* (2013.01); *G16H 50/70* (2018.01); *H04W 4/80* (2018.02); *H04W 88/08* (2013.01)

(58) Field of Classification Search
CPC ... A61B 5/4833; A61B 5/6824; A61B 5/6898; A61B 5/7405; A61B 5/7455; G08B 7/06; G08B 21/0272; G08B 21/0277; G08B 21/0288; G08B 21/182; G08B 25/001; G08B 25/016; H04W 64/00; H04W 76/10; H04W 4/80; H04W 88/08; A61M 5/20; A61M 15/00; A61M 2205/18; A61M 2205/3368; A61M 2205/3569; A61M 2205/3592; A61M 2205/50; A61M 2205/505; A61M 2205/52; A61M 2205/581; A61M 2205/587; A61M 2209/086
USPC ..................................... 340/539.12
See application file for complete search history.

(56) References Cited

U.S. PATENT DOCUMENTS

| | | |
|---|---|---|
| 6,629,932 B2 | 10/2003 | Weber et al. |
| 6,812,840 B2 | 11/2004 | Gehlot et al. |
| 6,937,150 B2 | 8/2005 | Medema et al. |
| 6,985,771 B2 | 1/2006 | Fischell et al. |
| 7,323,991 B1 | 1/2008 | Eckert et al. |
| 7,344,866 B2 | 3/2008 | Yamakawa et al. |
| 7,382,268 B2 | 6/2008 | Hartman |
| 7,627,334 B2 | 12/2009 | Cohen et al. |
| 7,715,277 B2 | 5/2010 | de la Huerga |
| 7,734,476 B2 | 6/2010 | Wildman et al. |
| 7,844,362 B2 | 11/2010 | Handfield et al. |
| 7,855,654 B2 | 12/2010 | Katz |
| 8,296,077 B2 | 10/2012 | Almiman |
| 8,537,343 B2 | 9/2013 | Zhang |
| 8,556,866 B2 | 10/2013 | Krulevitch et al. |
| 8,582,421 B2 | 11/2013 | Sloan |
| 8,630,660 B2 | 1/2014 | Ray et al. |
| 8,661,121 B1 | 2/2014 | Mendis |
| 8,843,104 B2 | 9/2014 | Adibi et al. |
| 8,916,390 B2 | 12/2014 | Ozcan et al. |
| 8,948,935 B1 | 2/2015 | Peeters et al. |
| 9,000,933 B2 | 4/2015 | Ray et al. |
| 9,041,538 B2 | 5/2015 | Peeters et al. |
| 2004/0265234 A1 | 12/2004 | Morimatsu et al. |
| 2005/0062603 A1 | 3/2005 | Fuerst et al. |
| 2007/0122840 A1 | 5/2007 | Cousins |
| 2007/0275427 A1 | 11/2007 | Akimoto et al. |
| 2008/0027679 A1 | 1/2008 | Dror Shklarski |
| 2008/0176253 A1 | 7/2008 | Christodoulides et al. |
| 2008/0180259 A1 | 7/2008 | Jung et al. |
| 2008/0199894 A1 | 8/2008 | Galasso |
| 2009/0134181 A1* | 5/2009 | Wachman ............... G16H 20/13 220/200 |
| 2009/0187424 A1 | 7/2009 | Grabowski |
| 2009/0294521 A1* | 12/2009 | de la Huerga .......... A61J 1/035 235/375 |
| 2009/0322513 A1 | 12/2009 | Hwang et al. |
| 2009/0326339 A1 | 12/2009 | Horvitz |
| 2010/0007501 A1 | 1/2010 | Yang |
| 2010/0062748 A1 | 3/2010 | Steinmetz |
| 2010/0065633 A1 | 3/2010 | Nelson et al. |
| 2010/0122709 A1 | 5/2010 | Janatpour et al. |
| 2010/0210033 A1 | 8/2010 | Scott |
| 2010/0211005 A1 | 8/2010 | Edwards |
| 2010/0222224 A1 | 9/2010 | Suni et al. |
| 2011/0139871 A1 | 6/2011 | Yturralde |
| 2012/0248134 A1* | 10/2012 | Santmyer ................. G07F 5/26 221/92 |
| 2013/0197445 A1 | 8/2013 | Schabbach et al. |
| 2014/0073262 A1 | 3/2014 | Gutierrez et al. |
| 2014/0155827 A1 | 6/2014 | Ostrander |
| 2014/0235171 A1 | 8/2014 | Molettiere et al. |
| 2014/0243749 A1 | 8/2014 | Edwards et al. |
| 2014/0309544 A1 | 10/2014 | Keenan et al. |
| 2014/0357304 A1 | 12/2014 | Ostrander et al. |
| 2015/0002281 A1 | 1/2015 | Berkobin et al. |
| 2015/0082542 A1 | 3/2015 | Hayes et al. |
| 2015/0137972 A1 | 5/2015 | Nepo |
| 2015/0154847 A1 | 6/2015 | Oliver et al. |
| 2015/0161558 A1* | 6/2015 | Gitchell ................. G06Q 50/22 235/375 |
| 2015/0161876 A1 | 6/2015 | Sal Castillo |

(56) References Cited

U.S. PATENT DOCUMENTS

| | | | |
|---|---|---|---|
| 2015/0170545 A1* | 6/2015 | Baker | G09B 23/285 |
| | | | 434/262 |
| 2015/0182115 A1 | 7/2015 | DeHennis | |
| 2015/0182696 A1 | 7/2015 | Kelly et al. | |
| 2015/0188311 A1 | 7/2015 | Kato et al. | |
| 2015/0221194 A1 | 8/2015 | Sarkar | |
| 2015/0360834 A1* | 12/2015 | Mikhail | B65D 51/248 |
| | | | 340/384.5 |
| 2017/0041769 A1 | 2/2017 | Shim | |
| 2019/0340900 A1* | 11/2019 | Herschkowitz | G08B 21/182 |
| 2022/0319659 A1* | 10/2022 | Lafauci | G16H 20/13 |

FOREIGN PATENT DOCUMENTS

| | | |
|---|---|---|
| KR | 10-2006-0124082 A | 12/2006 |
| WO | WO 2002/044865 | 6/2002 |
| WO | WO 2003/063754 | 8/2003 |
| WO | WO 2004/052204 | 6/2004 |
| WO | WO 2004/061412 | 7/2004 |
| WO | WO 2005/041131 | 5/2005 |
| WO | WO 2005/081707 | 9/2005 |
| WO | WO 2008/008451 | 1/2008 |
| WO | WO 2012/142623 | 10/2012 |
| WO | WO 2013/163326 | 10/2013 |
| WO | WO 2014/113785 | 7/2014 |
| WO | WO 2014/144548 | 9/2014 |
| WO | WO 2015/023895 | 2/2015 |
| WO | WO 2015/095172 | 6/2015 |
| WO | WO 2015/189700 A | 12/2015 |

OTHER PUBLICATIONS

Extended European Search Report dated Oct. 7, 2019 in corresponding European Application No. 17753860.0.

* cited by examiner

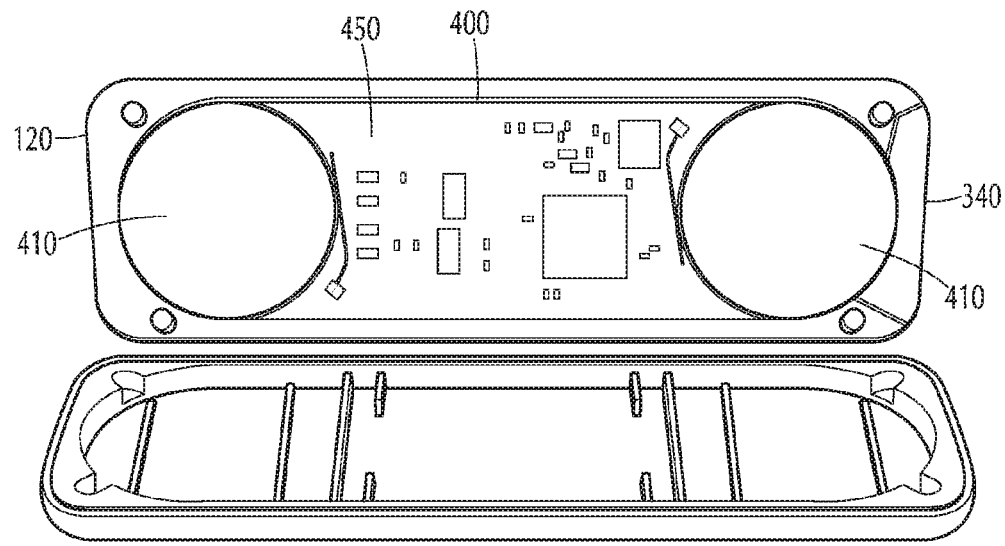
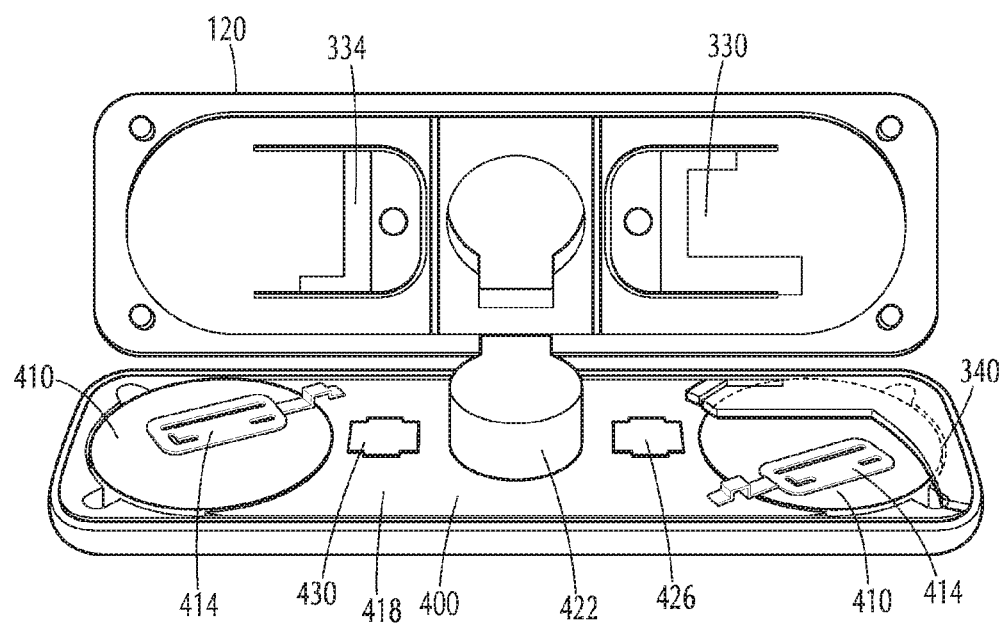
FIG. 4

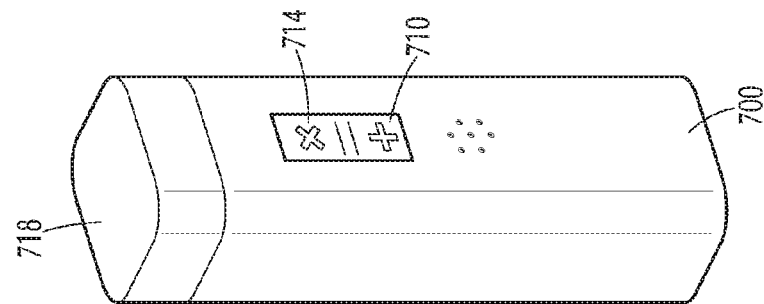
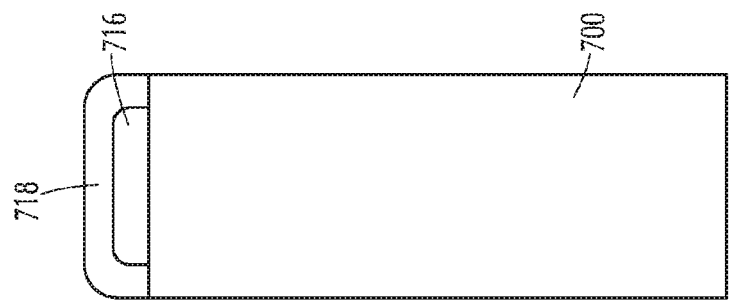
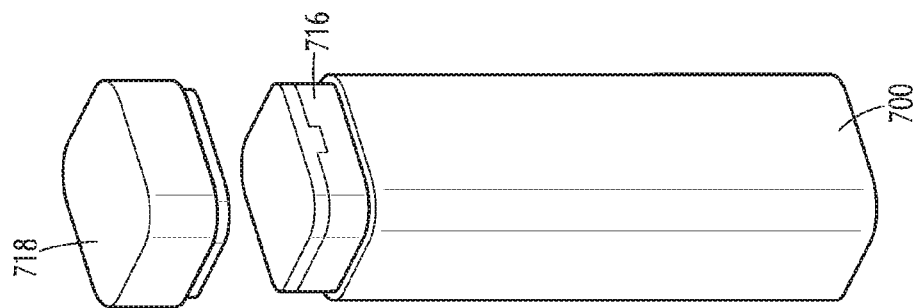
FIG. 6

FIG. 10F
Programming and Debugging
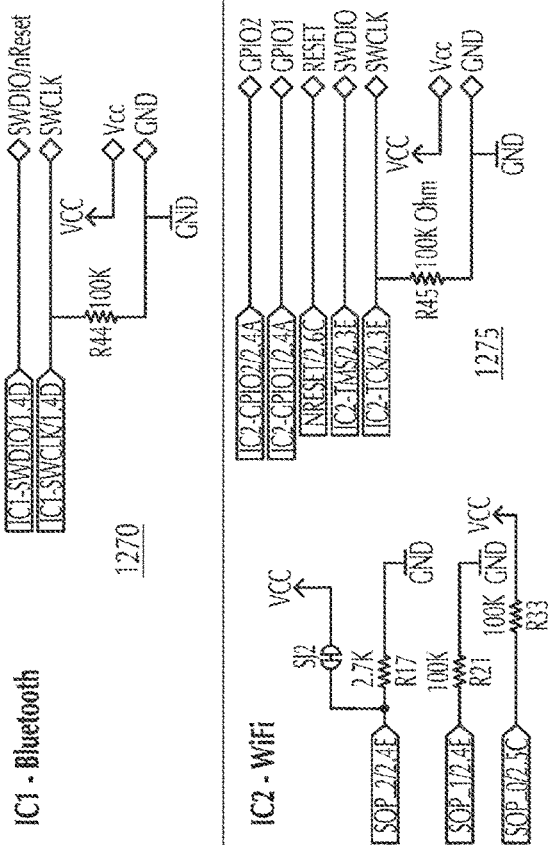
IC1 - Bluetooth  1270
IC2 - WiFi
IC3 - for loading files to Audio Decoder  1275
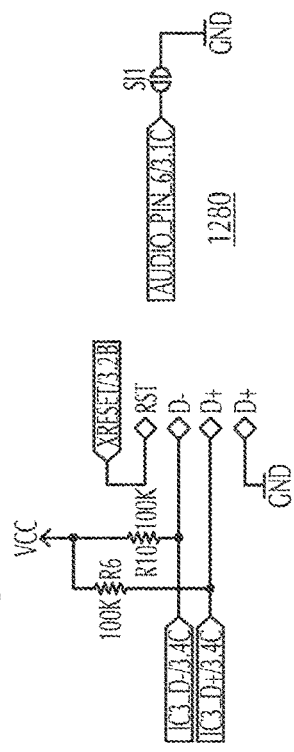
1280
POWER CIRCUIT
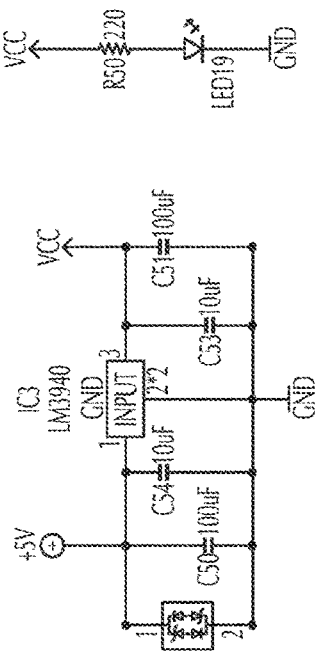
3.3V Voltage Regulation
total Amps needed: ~2A    1260
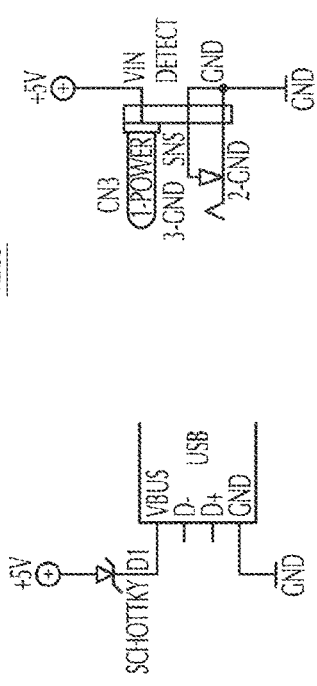
1265

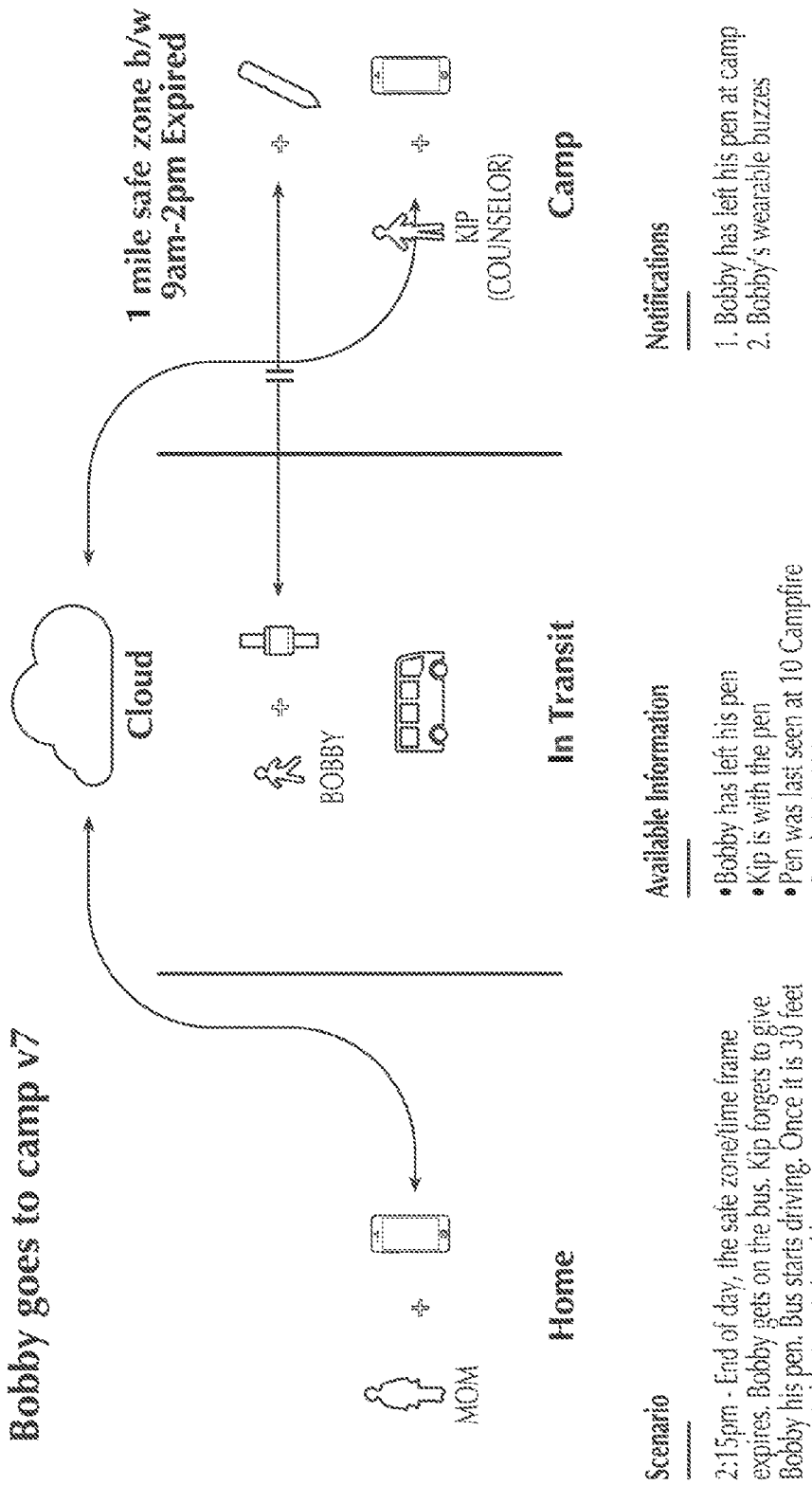

SYSTEMS FOR TRACKING MEDICATIONS

CROSS-REFERENCE TO RELATED APPLICATION

This application is a continuation of U.S. patent application Ser. No. 16/181,123, filed 5 Nov. 2018 and titled "Systems for Tracking Medications"; which is a continuation of U.S. patent application Ser. No. 15/435,145, now U.S. Pat. No. 10,163,311, filed 16 Feb. 2017 and titled "Systems for Tracking Medications"; and this application claims the benefit of U.S. provisional patent application No. 62/295,973, filed 16 Feb. 2016 and titled "Systems for Tracking Medications", all of which applications are hereby incorporated by reference in their entirety, including without limitation all appendices.

FIELD OF THE INVENTION

The present disclosure relates to integrated systems, methods, and apparatus that are capable of monitoring the absolute and relative locations and status of people and objects that are associated with them and to such systems, methods, and apparatus for helping individuals to manage acute life-threatening conditions such as food allergies, asthma, diabetes, migraines, and the like.

BACKGROUND OF THE INVENTION

This application contains material relating to medical services and medical information. The provision and handling of some medical services and medical information are regulated, as for example, by the United States Government, the various state governments, and other governmental agencies within the United States and elsewhere. The disclosure herein is made solely in terms of logical and financial possibility and advantage, without regard to possible statutory, regulatory, or other legal considerations. Nothing herein is intended as a statement or representation of any kind that any method or process proposed or discussed herein does or does not comply with any statute, law, regulation, or other legal requirement whatsoever, in any jurisdiction; nor should it be taken or construed as doing so.

Sometimes, keeping track of people and things is a matter of life and death.

Consider severe food allergies, for example. An allergic reaction to food can affect the skin, the gastrointestinal tract, the respiratory tract, and in the most serious cases, the cardiovascular system. Reactions can range from mild to severe, including the potentially life-threatening condition of anaphylaxis. During an anaphylactic event, an individual may have difficulty breathing and experience a drop in blood pressure. Anaphylaxis can result in death if not treated immediately with an epinephrine injection.

And food allergies are not particularly rare. To the contrary, according to the World Allergy Organization, the burden of food allergies is on the rise in both developed and developing countries. Worldwide, 240-550 million people have food allergies, and it is estimated that, in the United States, up to 15 million Americans have food allergies. This affects roughly 1 in every 13 children, which averages to about 2 children in every classroom. Further, food allergies in children increased at an alarming rate of approximately 50% between 1997 and 2011.

As of this writing, children's food allergies cost nearly S25 billion per year. Among children under the age of 18 in the United States, this life threatening medical condition has caused more than 200,000 visits to the emergency room and more than 300,000 ambulatory care visits each year. A food allergy reaction sends someone to the emergency room every 3 minutes.

Notwithstanding the seriousness of the condition and the immense cost, no clear cause of food allergies has been identified, much less a cure for this medical condition. The only known way to prevent anaphylaxis is a total avoidance of foods that contain the allergen, which is an endless, anxious challenge for the allergic individual.

Once an allergen is consumed, leading to anaphylaxis, epinephrine is the only life-saving form of treatment. Thus, individuals with food allergies are advised to carry 2 doses of epinephrine with them at all times, but it is often a burden for them and their families or other caregivers. For example, parents of young children need to make sure there are epinephrine injectors at school and with all daycare providers. Teenagers may not want to carry the injectors with them due to inconvenience, shame, bullying, or simple adolescent rebellion. And people forget things.

Further, epinephrine is worthless in an anaphylactic emergency if it is not administered. A person who may be experiencing signs of an allergic reaction may nonetheless hesitate to administer the epinephrine, maybe out of uncertainty that an anaphylactic reaction has begun or for fear of administering the injection. Individuals with allergies are sometimes not quite sure when they need to administer epinephrine, especially if they have not (to their knowledge) ingested an allergen, and they may hesitate because they do not want to deal with going to the hospital after injecting themselves with epinephrine. Those who do not have allergies may fear to use an epinephrine injector on someone else.

A number of U.S. patents relate to monitoring locations of portable medical devices, including U.S. Pat. No. 6,937,150 issued to Medema, et al., on Aug. 30, 2005, which discusses a remote locating service situated in an emergency response central dispatch. U.S. Patent Application Publication 2014/0155827, assigned to Mylan, Inc., discusses an application server configured to periodically receive location information of a medicament device from a mobile device. U.S. Patent Application Publication 2014/0243749, assigned to Intelliject, Inc., discusses a monitoring device that assists a patient in determining the location of a medicament delivery device and an alarm on the monitoring device to alert users of separation from the medicament delivery device.

Nevertheless, none of these patents and patent applications provides a reliable and integrated system that provides different levels of alerts and reminders for assisting an individual to manage and use his or her medication delivery devices across different day-to-day settings.

SUMMARY OF THE INVENTION

Embodiments of the invention relate to systems, methods, and apparatus for tracking the absolute and relative locations of individuals and objects that may be associated with them. Although the invention is of general applicability, embodiments of the invention may be used, e.g., in connection with medical conditions and devices and/or medications intended for use in treating and/or managing the conditions. Thus, embodiments of the invention may help individuals to manage medical conditions.

According to an embodiment of the invention, a system may help an individual to manage the use of a medication. The system comprises a first device configured to adhere to a container of the medication and a second device configured to communicate wirelessly with the first device. The second device comprises one or more processors and one or more computer-readable storage media electronically coupled to at least one of the processors. The computer-readable storage media are encoded with instructions that cause the second device at least to attempt to form a wireless connection with the first device. The instructions further comprise both (1) instructions that detect success of the attempt to establish a wireless connection with the first device and as a consequence of this detection cause the second device to provide output that indicates that the second device is connected to the first device, and (2) instructions that detect failure of the attempt to establish a wireless connection with the first device and as a consequence of this detection cause the second device to emit an alert.

In an embodiment of the invention, the container is a medical device. In an embodiment, the container is an autoinjector. In a further embodiment, the autoinjector comprises epinephrine.

In an embodiment of the invention, the second device comprises a locate button. When pressed, the locate button causes the second device to transmit a signal to the first device, the signal comprising a command to the first device to emit sound, light, or both.

In an embodiment of the invention, the first device comprises a temperature sensor. In an embodiment, the first device comprises one or more processors, one or more memories operatively coupled to at least one of the processors, and one or more computer-readable storage media operatively coupled to at least one of the processors. The computer-readable storage media is encoded with instructions that, when executed by at least one of the processors, cause the first device at least to store in at least one of the memories a temperature reading obtained from the temperature sensor, and, based on the temperature reading, emit a signal from the group that consists of a temperature warning signal and temperature damage signal. In an embodiment, the first device is configured to emit the temperature warning signal when the temperature sensor detects a temperature about 5% outside of a predetermined temperature range. In an embodiment, the first device is configured to emit the temperature damage signal when the temperature sensor detects a temperature about 10% outside of a predetermined temperature range.

In an embodiment of the invention, the second device is a base station. In an embodiment, the alarm signal triggers the base station to generate a sound. In an embodiment, the base station comprises a light emitting diode (LED), and receiving the alarm signal causes the base station to illuminate the LED. In an embodiment, the base station is configured to hold more than one type of medical devices.

In an embodiment of the invention, the second device is a wearable. In a further embodiment, the wearable comprises a vibration module, and in still a further embodiment, the alarm signal activates the vibration module. In an embodiment, the wearable comprises an audible alarm, and in a still further embodiment, the alarm signal activates the audible alarm.

In an embodiment of the invention the second device is a mobile phone. In an embodiment, the signal is communicated by the mobile phone to a support infrastructure.

In an embodiment of the invention, the second device is a wearable or a base station, and the system comprises a third device configured to communicate with the second device. The third device comprises one or more processors and one or more computer-readable storage media operatively coupled to at least one of the processors. The computer-readable storage medium is encoded with instructions that, when executed by at least one of the processors, cause the third device at least to try to establish a connection with the second device, determine the last visible location of the first device if a connection cannot be established, record the location of the first device if a connection is established, and report the location to a cloud server. In an embodiment, the third device is a mobile phone.

In an embodiment of the invention, the second device is a wearable or a base station, and the system comprises a third device configured to communicate with the second device. The third device comprises one or more processors and one or more computer-readable storage media operatively coupled to at least one of the processors. The computer-readable storage media are encoded with instructions that, when executed by at least one of the processors, cause the third device at least to establish a connection with a support infrastructure, determine, using the connection with the support infrastructure, whether the second device is in a safe zone, and provide, via the support infrastructure, a notification to the second device if the second device is determined to be outside of the safe zone.

In an embodiment, the safe zone is defined by a geographical location. In an embodiment, the safe zone is defined by a geographical location and a time schedule. In an embodiment, the third device is a mobile phone.

Although the invention may be discussed here primarily in connection with embodiments related to medical conditions and related devices and medications, the invention is not limited to such embodiments. To the contrary, embodiments of the invention may be applicable to various different circumstances in which it may be useful to track, e.g., the location and/or status of a person and an object.

For example, according to an embodiment of the invention, a system may enable monitoring, e.g., of a courier carrying sensitive information. A first electronic circuit or device may be affixed to a container (e.g., a briefcase or satchel) holding papers and/or computer-readable media. A second device may be configured to attempt to connect to the first device and to indicate whether the connection was successful, possibly causing an alert or alarm if the connection is not successful.

Similarly, in an embodiment of the invention, a system may help prevent, e.g., accidentally leaving an infant behind in a car. A first electronic circuit or device may be configured, e.g., to be worn securely but comfortably by the child. A second device may be configured to attempt to connect to the first device and to indicate whether the connection was successful, possibly causing an alert or alarm if the connection is not successful. The first device may in an embodiment of the invention incorporate, e.g., a temperature sensor and may transmit information reflecting temperature measurements.

BRIEF DESCRIPTION OF THE DRAWINGS

Some aspects of the disclosure are herein described, by way of example only, with reference to the accompanying drawings. With specific reference now to the drawings in detail, it is stressed that the particulars shown are by way of example and are for purposes of illustrative discussion of embodiments of the disclosure. In this regard, the description, taken with the drawings, make apparent to those skilled in the art how aspects of the disclosure may be practiced.

FIG. 4 is an exploded view of a sticker according to an embodiment of the invention.

FIG. 6 depicts a container that may perform functions of a sticker according to an embodiment of the invention.

FIGS. 10A-F combine to depict, as a schematic diagram, circuitry implementing an exemplary home base station according to an embodiment of the invention.

FIGS. 58-62 illustrate an exemplary system use scenario as described in Example 7.

DETAILED DESCRIPTION

Figure 1:
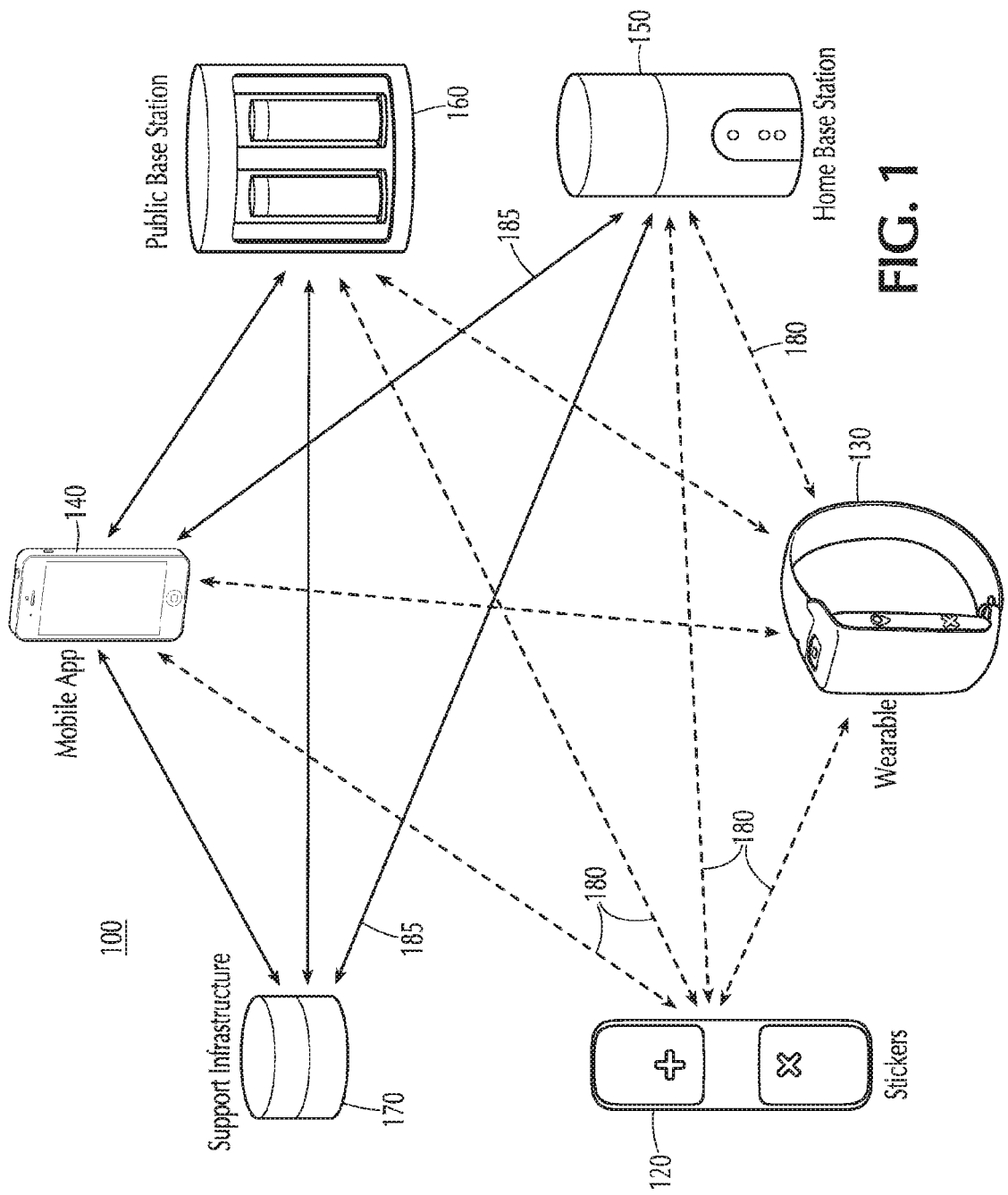
FIG. 1 depicts elements of a system and possible paths of communication between them according to an embodiment of the invention.

This description is not intended to be a detailed catalog of all the different ways in which the disclosure may be implemented, or all the features that may be added to the instant disclosure. For example, features illustrated with respect to one embodiment may be incorporated into other embodiments, and features illustrated with respect to a particular embodiment may be deleted from that embodiment. Thus, the disclosure contemplates that in some embodiments of the disclosure, any feature or combination of features set forth herein can be excluded or omitted. In addition, numerous variations and additions to the various embodiments suggested herein will be apparent to those skilled in the art in light of the instant disclosure, which do not depart from the instant disclosure. In other instances, well-known structures, interfaces, and processes have not been shown in detail in order not to unnecessarily obscure the invention. It is intended that no part of this specification be construed to effect a disavowal of any part of the full scope of the invention. Hence, the following descriptions are intended to illustrate some particular embodiments of the disclosure, and not to exhaustively specify all permutations, combinations and variations thereof.

Unless explicitly stated otherwise, the definition of any term herein is solely for identification and the reader's convenience; no such definition shall be taken to mean that any term is being given any meaning other than that commonly understood by one of ordinary skill in the art to which this disclosure belongs, unless the definition herein cannot reasonably be reconciled with that meaning. Further, in the absence of such explicit definition, all technical and scientific terms used herein have the same meaning as commonly understood by one of ordinary skill in the art to which this disclosure belongs. The terminology used in the description of the disclosure herein is for the purpose of describing particular embodiments only and is not intended to be limiting of the disclosure.

All publications, patent applications, patents, and other references cited herein are incorporated by reference in their entireties for the teachings relevant to the sentence and/or paragraph in which the reference is presented. References to techniques employed herein are intended to refer to the techniques as commonly understood in the art, including variations on those techniques or substitutions of equivalent techniques that would be apparent to one of skill in the art.

Unless the context indicates otherwise, it is specifically intended that the various features of the disclosure described herein can be used in any combination. Moreover, the present disclosure also contemplates that in some embodiments of the disclosure, any feature or combination of features set forth herein can be excluded or omitted.

The methods disclosed herein comprise one or more steps or actions for achieving the described method. The method steps and/or actions may be interchanged with one another without departing from the scope of the present invention. In other words, unless a specific order of steps or actions is required for proper operation of the embodiment, the order and/or use of specific steps and/or actions may be modified without departing from the scope of the present invention.

As used in the description of the disclosure and the appended claims, the singular forms "a", "an", and "the" are intended to include the plural forms as well, unless the context clearly indicates otherwise.

As used herein, "and/or" refers to and encompasses any and all possible combinations of one or more of the associated listed items, as well as the lack of combinations when interpreted in the alternative ("or").

The term "about," as used herein when referring to a measurable value such as distance and the like, is meant to encompass variations of ±20%, ±10%, ±5%, ±1%, ±0.5%, or even ±0.1% of the specified amount.

As used herein, phrases such as "between X and Y" and "between about X and Y" should be interpreted to include X and Y. As used herein, phrases such as "between about X and Y" mean "between about X and about Y" and phrases such as "from about X to Y" mean "from about X to about Y."

The terms "comprise," "comprises", and "comprising", as used herein, specify the presence of the stated features, integers, steps, operations, elements, and/or components, but do not preclude the presence or addition of one or more other features, integers, steps, operations, elements, components, and/or groups thereof.

The term "computer-readable storage medium", as used herein, specifically does not refer to transitory propagating signals.

As used herein, the transitional phrase "consisting essentially of" means that the scope of a claim is to be interpreted to encompass the specified materials or steps recited in the claim and those that do not materially affect the basic and novel characteristic(s) of the claimed disclosure. Thus, the term "consisting essentially of", when used in a claim of this disclosure, is not intended to be interpreted to be equivalent to "comprising".

As used herein, the term "subject" refers to an individual who has a medical condition such as, but not limited to, a food allergy, diabetes, asthma, and/or migraines.

As used herein, the term "team" refers to a group of individuals associated with a subject through the systems as described herein.

As used herein, the term "team member" refers to any individual in a team associated with a subject.

As used herein, the term "public user" refers to an individual who is a team member in another team.

As used herein, the term "recipient" refers to an individual who receives shared information, but is not a team member of any teams.

As used herein, the term "paired" refers to the establishment of a connection between two devices to form the systems as described herein.

As used herein, the term "connected" refers presence of communication between at least two devices in the systems described herein, including transmitting or receiving a signal.

As used herein, the term "epinephrine pen" refers a single dose of epinephrine provided in an autoinjector in accordance with the present disclosure.

As used herein, the term "home" refers to a reference starting location. It does not necessarily refer to the home at which a subject resides.

As used herein, the term "cloud" refers to one or more computer servers that are built, hosted, and delivered through a platform over internet according to the present disclosure.

As used herein, the term "wearable" refers to an electronic device that is worn by an individual.

As used herein, "prevention" or "preventing," with respect to a condition or a disease, is an approach for reducing the risk of developing a condition or a disease before it manifests in a patient. Prevention approaches include, but are not limited to: identifying a disease at its earliest stage so that prompt and appropriate management can be initiated, protecting a tissue prone to a condition or a disease prior to its manifestation, reducing or minimizing the consequences of a disease, and a combination thereof.

As used herein, "treatment" or "treating", with respect to a condition or a disease, is an approach for obtaining beneficial or desired results including preferably clinical results after a condition or a disease manifests in a patient. Beneficial or desired results with respect to a disease include, but are not limited to, one or more of the following: improving a condition associated with a disease, curing a disease, lessening severity of a disease, delaying progression of a disease, alleviating one or more symptoms associated with a disease, increasing the quality of life of one suffering from a disease, prolonging survival, and a combination thereof. Likewise, for purposes of this disclosure, beneficial or desired results with respect to a condition include, but are not limited to, one or more of the following: improving a condition, curing a condition, lessening severity of a condition, delaying progression of a condition, alleviating one or more symptoms associated with a condition, increasing the quality of life of one suffering from a condition, prolonging survival, and a combination thereof.

Embodiments of the invention discussed here may relate primarily to persons with potentially life-threatening medical conditions and devices for administration of medications. Those embodiments may relate more specifically to persons with severe food allergies and epinephrine autoinjectors. But it will be appreciated that the invention is not limited such circumstances, and embodiments of the invention may relate to any analogous circumstance in which it is wished to track the relative and absolute locations of two or more persons and/or objects and possibly take one or more automated actions based on detected changes in the status and/or locations of some or all of the tracked persons and/or objects.

In connection with an embodiment, a medication may be contained in a container. For example, the container may be a medical device or, alternatively, an enclosure that contains a medical device. For this purpose, a medical device may be, e.g., an autoinjector, an injector, or an inhaler, but may be another device or type of device.

In an embodiment of the invention, the medical device may be an autoinjector filled with injectable epinephrine. As used herein, "epinephrine" refers to a natural or synthesized compound that binds to a variety of adrenergic receptors, including but not limited to the major subtypes $\alpha_1$, $\alpha_2$, $\beta_1$, $\beta_2$, and $\beta_3$. Epinephrine may be racemic or non-racemic. Epinephrine may be used to treat medical conditions including, but not limited to, anaphylaxis.

In connection with some embodiments of the invention, a single dose of injectable epinephrine may be provided in commercially available forms including but not limited to, an EpiPen®, an Auvi-Q®, an Allerject®, an Adrenaclick®, or a Twinject®.

In connection with other embodiments of the invention, the medical device may be an inhaler filled with bronchodilators including, but not limited to, salbutamol, albuterol, levosalbutamol, levalbuterol, pirbuterol, epinephrine, ephedrine, terbutaline, salmeterol, clenbuterol, formoterol, bambuterol, and indacaterol. In connection with other embodiments, the medical device may be an injector or autoinjector filled with insulin, which may be long-acting or short-acting. In connection with other embodiments of the invention, the medical device may be an injector or an autoinjector filled with epilepsy medications, including, but not limited to, lorazepam, fosphenytoin sodium, valproate sodium, phenytoin, adrenocorticotropin hormone (ACTH), and diazepam. In connection with other embodiments of the invention, the medical device may be an injector or an autoinjector filled with migraine medications including, but not limited to, ergotamine, dihydroergotamine, chloropromazine, droperidol, haloperidol, metoclopramide, prochlorperazine, sumatriptan, nonsteroidal anti-inflammatory drug (NSAIDs), merperidine, nalbuphine, and tramadol.

FIG. 1 depicts, conceptually, interacting components of a system 100 for tracking medication according to an embodiment of the invention. As depicted, a system 100 may include one or more "stickers" 120, which may be devices that are intended to adhere, e.g., to medication containers (not pictured). In an embodiment of the invention, a sticker 120 may be capable of transmitting information, which may include information representing the identity and status of the sticker 120 and/or the medication and/or medication container that it adheres to. A sticker 120 in an embodiment may also be capable of emitting, e.g., sound and or light in response to a signal, to aid in locating the medication container.

A system 100 may also include one or more "wearables" 130, which, as the name suggests, may be devices designed, e.g., to be worn by a subject and/or clipped or otherwise removably attached to clothing or other article worn by a subject. A wearable 130 in an embodiment of the invention may be configured, e.g., to attempt to detect signals from one or more stickers 120, thereby indicating proximity of the sticker 120 and the wearable 130. The wearable 130 may also be capable in an embodiment of transmitting information, e.g., to cause at sticker 120 to emit light and/or sound, and/or to indicate the location of or other information about the wearer.

In an embodiment of the invention, a mobile application ("app") 140 on a device such as, e.g., a smartphone, may support and/or coordinate operation of the system for one or more persons, including, e.g., one or more subjects. A system may also include one or more home base stations 150 and/or one or more public base stations 160. Operation of the system may be coordinated, e.g., by a network-based server infrastructure 170.

FIG. 1 should be understood to depict types of elements, some or all of which may exist in a system 100 according to embodiments of the invention. Multiples of any or all depicted elements may exist, operate, and interoperate in an embodiment of the invention. For example, in connection with an embodiment of the invention, thousands of subjects may have the mobile app 140 installed on their respective mobile devices, while each subject may have one or more wearables 130, one or more home base stations 150 and multiple stickers 120. Other home base stations 150 and/or public base stations 160.

According to embodiments of the invention, communication paths may exist between elements, including elements of different types. For example, in an embodiment such as FIG. 1 depicts, stickers 120 may communicate with wearables 130, mobile apps 140, home base stations 150, and public base stations 160. In FIG. 1, these paths are depicted by dashed arrows 180, indicating that in the depicted embodiment, the communication between devices takes place over a short-range connection that is directly between the devices, using, e.g., Bluetooth® Low Energy.

Similarly, in an embodiment such as FIG. 1 depicts, a home base station 150 may communicate with stickers 120, wearables 130, mobile apps 140, and the support infrastructure 170. Again, as depicted, dashed arrows 180 indicate short-range direct connections. Further, the solid arrows 185 connecting the home base station 150 with the mobile app 140 and the support infrastructure 170 indicate connections via a network such as, e.g., a wired or wireless LAN or the Internet.

It will be appreciated that FIG. 1 merely depicts possible communication paths according to an exemplary embodiment of the invention. Except as explicitly disclosed herein, devices may potentially be capable of any one or more communication methods or pathways consistent with the nature and purpose of the devices.

Figure 2:
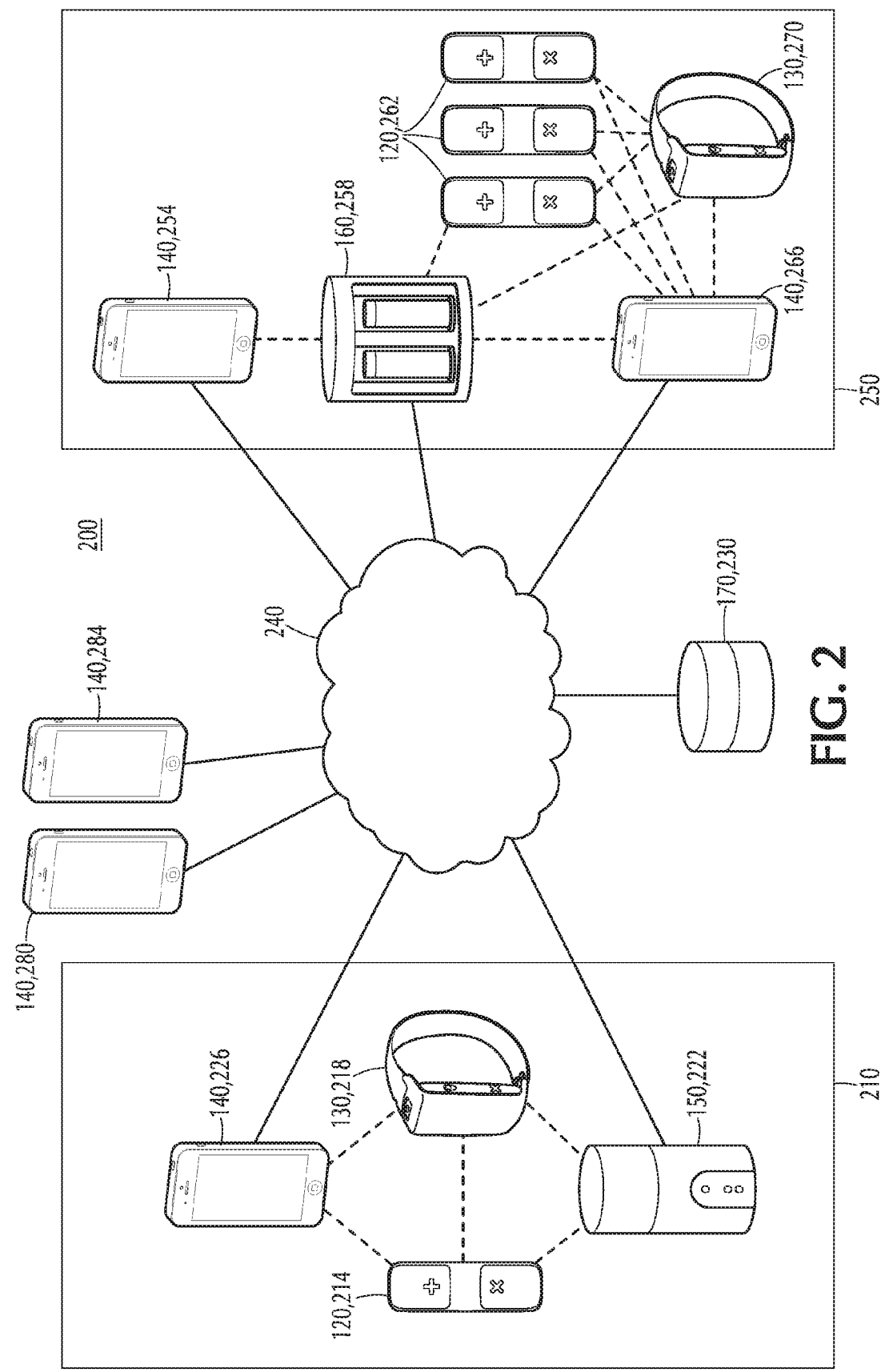
FIG. 2 depicts schematically a network architecture of a system according to an embodiment of the invention.

FIG. 2 depicts a simplified network architecture 200 to further illustrate conceptually potential methods and paths of interaction according to embodiments of the invention. For example, in a home 210, a sticker 214 may communicate, e.g., via Bluetooth® Low Energy with a wearable 218, a home base station 222, and an app 226 on a mobile device.

The wearable 218 may additionally and similarly communicate with the home base station 222 and the app 226. The home base station 222 and app 226 may further be in communication with each other and with other components, including, e.g., the support infrastructure 230, via, e.g., the Internet 240.

It will be appreciated that other communication paths and methods may be used within a home 210 in addition to or instead of some or all of the depicted paths. For example, the home base station 222 may communicate (not pictured) with the app 226 on the mobile device, e.g., via a shared wired or wireless network (not pictured), a Bluetooth® connection (not pictured), a USB connection (not pictured), and/or any other convenient method.

FIG. 2 also depicts a public location 250, such as, e.g., a restaurant. An app 254 at this location 250 may communicate with a public base station 258 and via the Internet 240 with other components. A group of stickers 262 may communicate with the public base station 258, an app 266 on a second mobile device, and a wearable 270, all of which may also communicate with each other. The public base station 258 and the app 266 may also communicate with other components via the Internet 240.

FIG. 2 further depicts two other apps 280, 284 on other devices at unspecified locations, which communicate with other components, including, e.g., the support infrastructure 230 via the Internet 240.

It bears repeating that FIG. 2 depicts merely a simplified set of devices and communication paths for the purpose of illustrating the principles that may operate in an embodiment of the invention. In an embodiment of the invention, other pathways and/or protocols may be used in addition to or instead of any one or more depicted pathways, and in any or all of the depicted roles.

Figure 3:
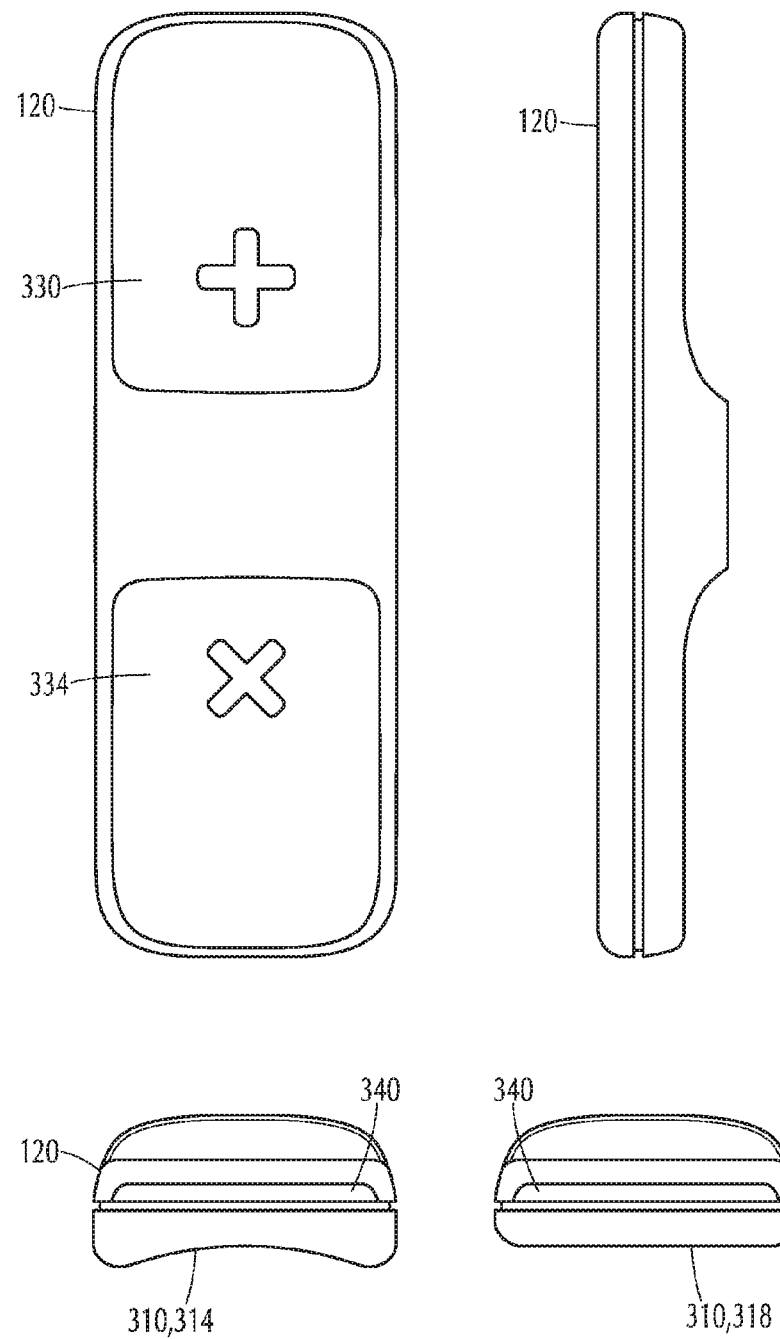
FIG. 3 depicts a sticker according to an embodiment of the invention.

FIG. 3 depicts a sticker 120 according to an embodiment of the invention, viewed from the front (a), one side (b), and one end (c). In embodiments of the invention, the dimensions of the sticker 120 may reflect the size of its components, but may also reflect a desire to minimize (or at least reduce) the bulk that the sticker 120 adds when affixed to a container. In embodiments, sticker 120 may be of a size and or shape chosen to not cover any medical label information on the container.

In an embodiment, the sticker 120 may comprise an adhesive, e.g., affixed to the underside 310 of the sticker 120, that allows the sticker 120 to permanently or removably (depending on the embodiment) adhere to the container. The underside 310 may in an embodiment be shaped to facilitate adhesion of the sticker 120 to the container. For example, in an embodiment, the underside 314 may be curved to enhance adhesion to a curved medication container, while in an embodiment, the underside 318 may be flatter to enhance adhesion to a correspondingly shaped container.

A sticker 120 in an embodiment such as FIG. 3 depicts may have two buttons on the front: an emergency button 330 and a cancel/pair button 334. In an embodiment of the invention, a subject may trigger an emergency alert (discussed further below) by pressing the emergency button 330. It will be appreciated that, to reduce the chance of false alarms, a sticker 120 may be configured not to signal an emergency immediately, but only after the emergency button 330 has been held down for a predetermined interval. For example, in an embodiment of the invention, a sticker 120 may not signal an emergency until the emergency button 330 has been held down for at least 3 seconds.

In an embodiment of the invention, once an emergency has been signaled, the alert may be canceled by pressing the cancel/pair button 334. As before, to prevent accidental cancellation of the alert during an actual emergency, the sticker 120 may be configured to require that the cancel/pair button 334 be held down continuously for a predetermined interval. For example, in an embodiment of the invention, the sticker may not cease indicating the emergency until the cancel/pair button 334 has been held down for at least 3 seconds.

The cancel/pair button 334 may also be used to pair a sticker, e.g., with a mobile device or an app on that device, e.g., as described elsewhere in this document.

A sticker 120 in an embodiment of the invention may also be configured to emit light, e.g., during an emergency or, on request, as a way to help find the sticker and the medication container it is attached to. For example, in an embodiment of the invention, a red LED light pipe 340 may emit light from the top of the sticker 120 when suitably powered.

As already described, a sticker 120 according to embodiments of the invention may communicate with other devices. In an embodiment of the invention, a sticker may be configured to use Bluetooth® Low Energy (BLE) technology to communicate with other devices. BLE, which is well known in the art, is a technology for wirelessly creating ad hoc networks of electronic devices. (The name reflects the fact that BLE consumes less energy than its predecessors.) To be detected, a BLE device broadcasts advertising packets, which other BLE devices scan for. When a scanner detects an advertising packet, it may respond and begin negotiating a link between itself and the source of the packet.

iBeacon™ is a protocol promoted as a technology for location and proximity detection. A device that uses iBeacon™ emits BLE advertising packets that follow a strict format that is defined in the protocol. As it is typically used, an iBeacon™ device periodically broadcasts these advertising packets that include information that uniquely identifies the device. A device such as a smartphone that receives the packet may determine from that fact that it is near the iBeacon™, and thereby deduce its own location based on the known location of the iBeacon™.

According to the iBeacon™ standard, the identifying information in an advertising packet comprises a 16-byte Universally Unique Identifier (UUID), a 2-byte major ID, and a 2-byte minor ID. As conventionally used, the UUID is unique to the user, the major ID identifies the user-defined group of devices that includes the particular iBeacon™, and the minor ID identifies the particular iBeacon™ within that group.

Thus, for example, devices using the iBeacon™ protocol may be placed throughout a department store; the UUID may identify the store or store owner, the major ID of a particular iBeacon™ may identify the floor on which the device has been placed, and the minor ID may identify the particular iBeacon™ on that floor. The department store may also offer an app to its customers. The app, when used within the store, may use the identifying data of the device or devices detected at any location to find the user's location within the store and then use this information, e.g., to give the user directions to some other specified part of the store.

A sticker 120 in embodiments of the invention may broadcast one or more signals or types of signals to make its presence discoverable by other devices. In one embodiment, a sticker 120 may include a communication module configured to transmit signals using the iBeacon® protocol. In such an embodiment, the UUID and Major ID may identify, e.g., the device and the subject. But in an embodiment of the invention, the identification data in the minor ID may be changed, according to programming in the device, to provide certain information about the device.

For example, in an embodiment of the invention, the minor ID may be used to signal, e.g., whether the sticker 120 is signaling an emergency, whether the battery is low, whether the ambient temperature puts the medication at risk, and/or whether the device (and therefore the medication) has been exposed to temperatures such that the medication or medication container may be damaged and possibly unusable. Table 1 presents, in the form of hexadecimal numbers, values that may be associated with each of these conditions: in an embodiment, a sticker 120 using iBeacon™ may broadcast a minor ID that is a logical OR of the values associated with each applicable state, with a minor ID of zero indicating that none of listed conditions applies.

TABLE 1

Exemplary Minor ID mapped to various sticker device statuses

| Data Sets Communicated To/From Cloud | Data Type (in hexadecimal) |
| --- | --- |
| Emergency state | Minor ID 0 × 01 |
| Low battery state (<25%) | Minor ID 0 × 02 |
| Temperature at risk state | Minor ID 0 × 04 |
| Temperature damaged state | Minor ID 0 × 08 |
| Find My Pen state | Minor ID 0 × 10 |

Thus, for example, emergency state (0x01) and low battery state (0x02) may be transmitted as 0x03. If the emergency is subsequently canceled, the low battery state may still apply, so the broadcast minor ID may change from 0x03 to 0x02 to reflect the cancellation.

It will be appreciated that in embodiments of the invention, a Minor ID as described above may be used to encode any desired information, including, e.g., information about the state and/or of the transmitting device, consistent with the requirements of the applicable protocol or protocols.

It will be appreciated that a subject may suffer a serious or potentially life-threating episode while in possession of a medication container with a sticker 120 attached. For example, due to a severe food allergy, a subject may carry an epinephrine autoinjector with a sticker 120 attached. In case of exposure to an allergen or onset of symptoms of anaphylaxis, the subject may wish to summon help and/or to alert caregivers, in addition to administering the epinephrine. Thus, in such a circumstance, in connection with an embodiment of the invention, the subject or other person may press the emergency button 330 on the sticker, e.g., as described above.

In response, the sticker may change the state information that it broadcasts using iBeacon™ to reflect the emergency, and this change may be detected and acted upon, e.g., as described below. But in an embodiment of the invention, the sticker may also be configured to attract attention locally, e.g., by emitting sound and or light. For example, a sticker 120 may include a light pipe 340 that may, e.g., brightly flash red. In addition to or instead of the light, a sticker 120 in an embodiment of the invention may be configured to make a loud noise, e.g., by including a buzzer.

It will be appreciated that transmitting iBeacon™ broadcasts consumes energy. To improve battery life, in an embodiment of the invention, a variable broadcast interval may be used. In an exemplary embodiment of the invention, the broadcast interval may be set by an algorithm such as: 1) start with a broadcast interval of 60 seconds; 2) if not connected to BLE central within 1 hour, increase broadcast interval to 120 seconds; 3) if not connected to BLE central within 3 hours, increase broadcast interval to 180 seconds; 4) upon connection with BLE central, if broadcast interval is greater than 60 seconds, reduce broadcast interval to 60 seconds.

In addition to its iBeacon™ function, a sticker 120 according to an embodiment of the invention may also operate in BLE connected device mode, e.g., to enable receipt of commands, such as the command to enter "Find My Pen" mode. For example, in an embodiment, a sticker 120 may accept commands, e.g., to enter and exit emergency mode, to activate and cancel "Find My Pen" state, to enter setup state, to tag the medication as damaged and/or expired, and to alter the iBeacon advertising interval.

FIG. 4 depicts a circuit board 400 inside a sticker 120 according to an embodiment of the invention. In an embodiment such as FIG. 4 depicts, power is provided by two lithium coin cells 410 in contact with the circuit board 400, each held in position by a clip 414. In one embodiment, the batteries 410 may be non-rechargeable 3-volt CR1616 cells.

As depicted, the upper side 418 of the circuit board 400 includes a buzzer 422 and two switches 426, 430 that are aligned to be actuated by the emergency button 330 and the cancel/pair button 334.

Figure 5A:
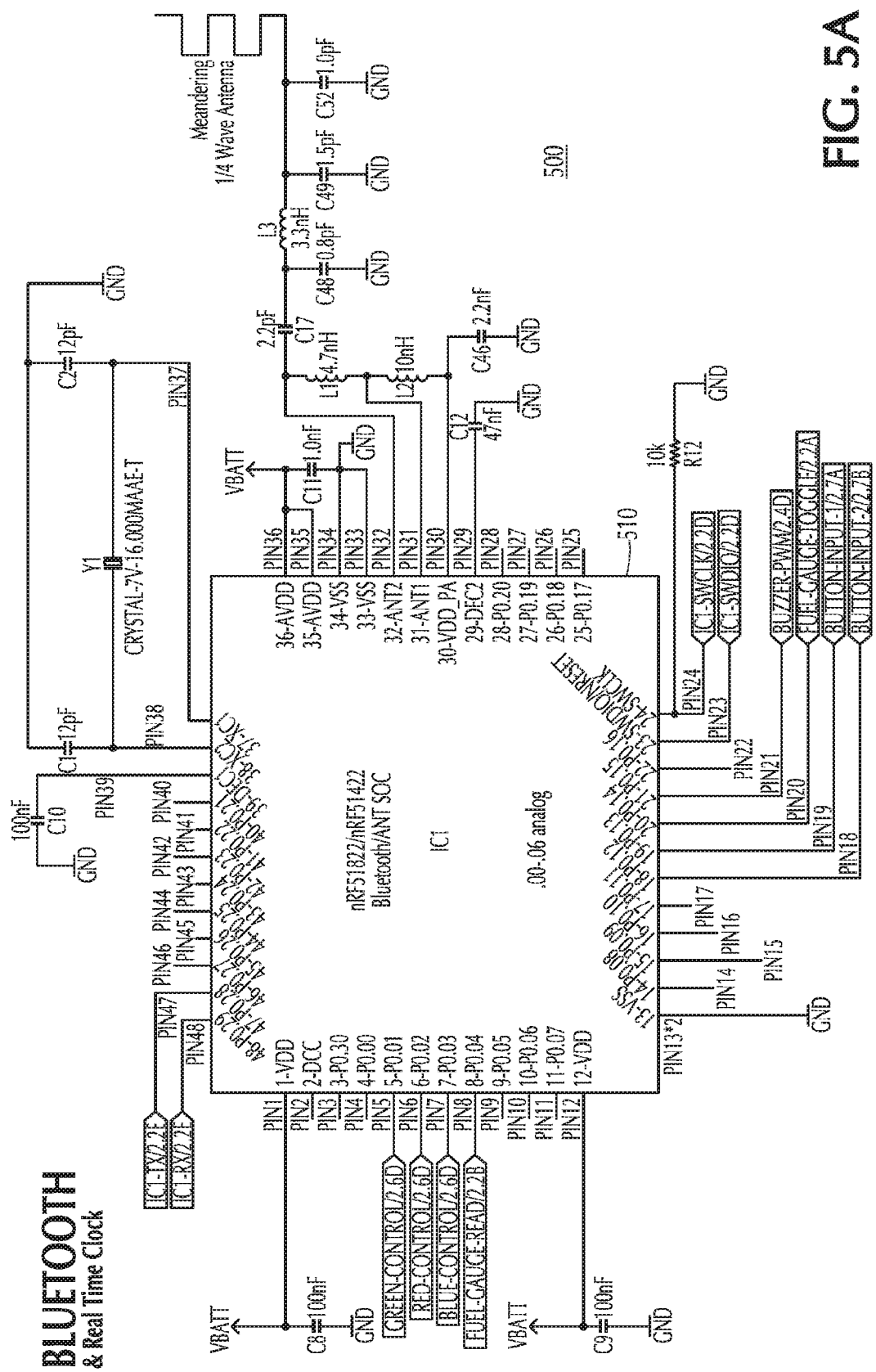
FIGS. 5A-B combine to depict, as a schematic diagram, circuitry implementing an exemplary sticker according to an embodiment of the invention.
Figure 5B:
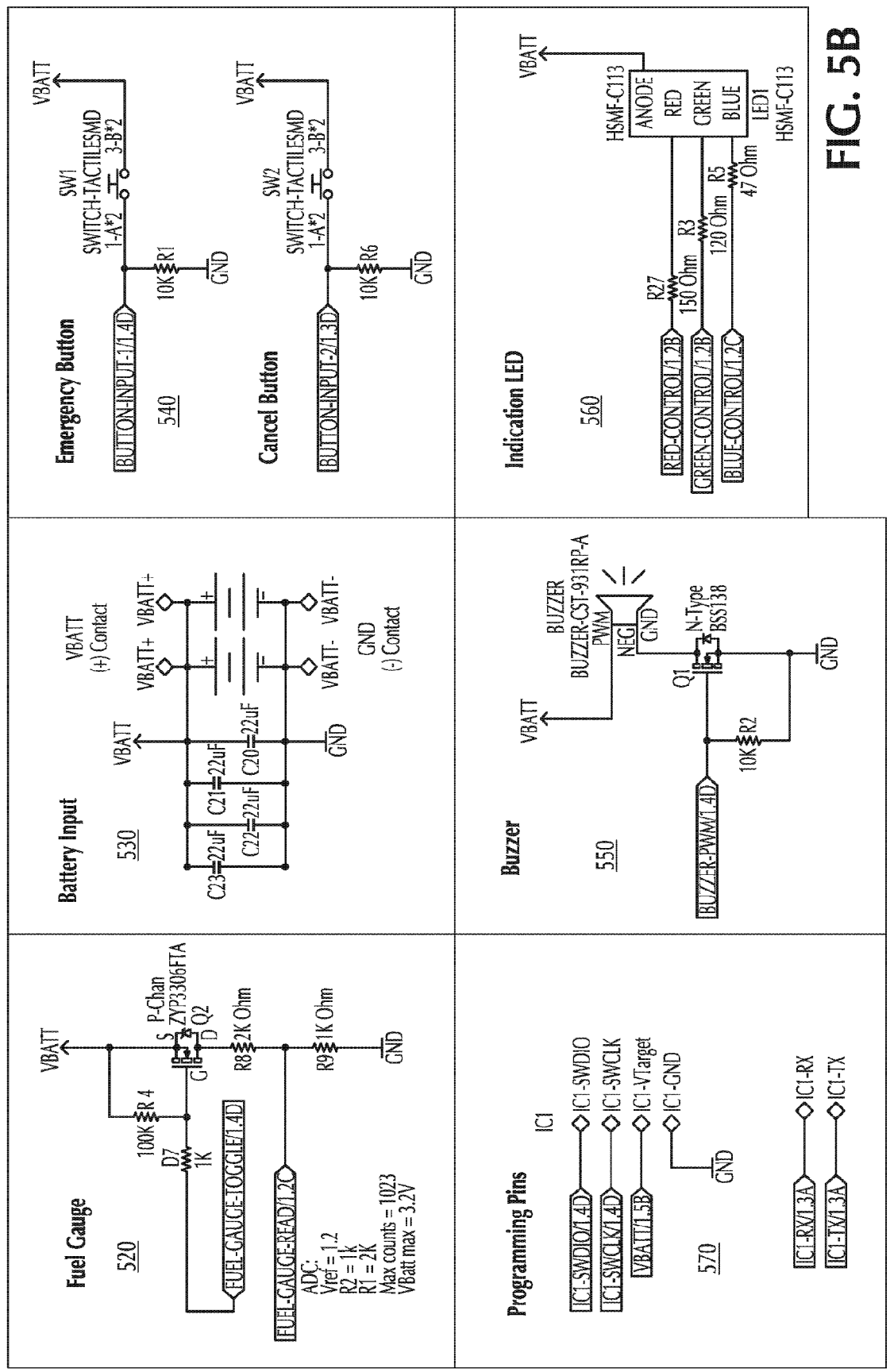

As FIG. 4 depicts, various circuit components are visible on the underside 450 of the circuit board 400. FIGS. 5A-B depict, as circuit schematics, an implementation of a sticker 120 according to an exemplary embodiment of the invention.

In an embodiment such as FIGS. 5A-B depict, core logic and wireless systems 500 may be implemented, e.g., as in FIG. 5A, by a Bluetooth® system-on-chip ("SoC") 510 such as the nRF51422 or nRF51822, both of which are SoCs made commercially available by Nordic Semiconductor.

FIG. 5B depicts circuit schematics for additional systems implemented on a circuit board 400 in a sticker 120 in an embodiment of the invention. As depicted, The batteries provide power in connection with battery input circuitry 530, and a fuel gauge 520 circuit measures the voltage provided by the batteries 410 and provides this measurement to an analog input of the SoC 510. FIG. 6 also depicts circuits for the buttons 540, the buzzer 550, the indicator LED 560, and programming pins 570, according to an embodiment of the invention. Although not depicted, ambient temperature may be measured by any appropriate means; in an embodiment of the invention, it may be measured, e.g., with reference to an on-die temperature sensor incorporated in the SoC 510.

It will be appreciated that in embodiments of the invention, the functions of a sticker 120 may be performed by a device that differs in shape and/or implementation from that described above. For example, as disclosed, a sticker 120 according to embodiments of the invention may be powered, e.g., by non-rechargeable lithium coin cells 410, and these cells 410 may, e.g., be sealed within the case of the sticker 120 such that they cannot reasonably be replaced by an end user. In other embodiments of the invention (not pictured), the sticker 120 may, for example, provide means for the user to replace the batteries 410.

In still other embodiments of the invention, a sticker 120 may be powered by one or more rechargeable batteries (not pictured). In such embodiments, the circuits may include, e.g., one or more ports (such as, for example, a micro-USB port) that allow external power to be supplied, and one or more circuits that, e.g., apply this power to recharge the batteries.

In connection with an exemplary embodiment described above, the expected useful life of the cells 410 within a sticker 120 had been determined through experiment to be roughly the same as the expected useful life of an epinephrine autoinjector that the sticker 120 might be attached to, and therefore the remaining lifetime of the cells 410 may be used in such an embodiment as a proxy for the time until expiry of the medication in the autoinjector. It will be appreciated that in alternative embodiments in which the batteries may be replaced and/or recharged, the time to expiry may be calculated differently, e.g., by including a real-time clock and measuring the actual time since the autoinjector was acquired.

In embodiments of the invention, a sticker 120 may be associated with the medication container through a means other than adhesion. (Unless explicitly stated otherwise or required by context, "sticker" may refer herein to devices according to embodiments of the invention that perform the functions and/or roles of a sticker 120, even though, in an embodiment, a particular device may not be intended literally to stick to a tracked object.) For example, in an embodiment of the invention, for a suitably shaped medication container or other object, a sticker 120 may be attached to the object, e.g., with a cable tie or similar mechanism (not pictured) or, removably, e.g., with a carabiner or other clip (not pictured).

FIG. 6 depicts a container 700 in an embodiment of the invention with circuitry built into it that performs the functions of the sticker 120. The outside of the container 700 in such an embodiment may provide, e.g., an emergency button 710 and a cancel/pair button 714 that function as described above, and may be capable of emitting light and/or sound, also as described above.

The container 700 may be capable of containing, e.g., an epinephrine autoinjector or other tracked object 716, which may in an embodiment be kept in the container 700, e.g., by a removable cap 718. In such an embodiment, the container 700 may be configured so that removing the cap triggers an emergency, e.g., as previously described.

In some embodiments, a sticker 120 may also enable securely and anonymously retrieving lost medical devices or be supplied with other means for doing so. For example, in an embodiment, a label (not pictured) may be provided, e.g., printed on the sticker 120 or as a separate object to be applied to the container. The label may instruct a finder to put the medication container into a mailbox, upon which the medication container may be forwarded to a central dispatch. The label may also provide a bar code or other computer-readable identifier, that may, e.g., be scanned upon receipt at the central dispatch to identify the owner of the medication container, which may then be returned to the owner. Alternatively, the owner may be identified by comparing the information broadcast by the sticker 120 according to the iBeacon® protocol with information about registered devices.

According to embodiments of the invention, the location of the sticker may be monitored as a proxy for monitoring the location of the autoinjector or other object to which it is attached. A smartphone or similar mobile device may be a suitable observer of stickers' locations because it may be capable of interacting with stickers, e.g., via Bluetooth® and/or similar technologies and also capable of interacting with remote system components, e.g., via a wireless Internet connection.

But embodiments of the invention may serve, e.g., to help parents monitor children's possession of autoinjectors. It will be appreciated, however, that many children do not carry smartphones. Thus, in embodiments of the invention, a wearable device may observe the stickers' locations. Such a device may, for example, provide a reference for a child's location, enabling determination whether the child is with or without their medication/sticker. The observation of the wearable may thus be considered to be an observation of the child.

A wearable according to embodiments of the invention may act as a separate battery-powered observer that a child could carry, e.g., to school. Depending on the embodiment, a wearable may or may not have independent capabilities for connecting, e.g., to the Internet. But, once configured to be paired with one or more stickers, a wearable may implement "leash" functionality, according to which it may keep track of whether any such stickers are nearby and, e.g., alert the child who wears the wearable if no sticker is seen.

Figure 7:
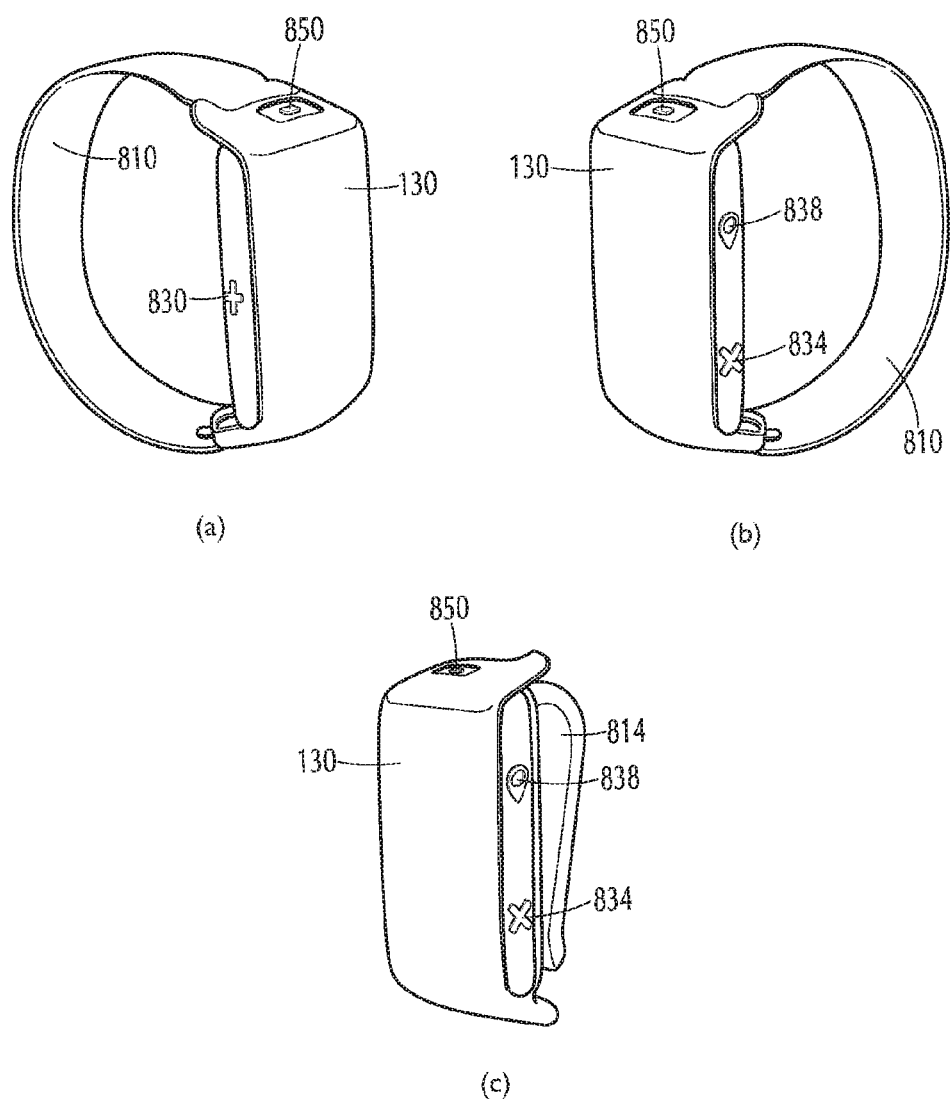
FIG. 7 depicts a wearable according to an embodiment of the invention.

FIG. 7 depicts a wearable 130 according to embodiments of the invention. In views (a) and (b), the depicted wearable 130 includes a strap 810, which may permit a subject to wear the wearable 130, e.g., around the wrist, in the manner of a wristwatch. In view (c), the wearable 130 includes a clip 814, which may allow the wearable 130 to be attached, e.g., to a garment the subject is wearing. It will be appreciated that a wearable 130 in an embodiment of the invention may be configured to be removably attachable, e.g., to a strap 810 and/or a clip 814, which may allow a subject to change how the wearable 130 may be worn.

A wearable 130 in an embodiment of the invention may have buttons. For example, in an embodiment, a wearable 130 may have an emergency button 830 and/or a cancel/pair button 834, which may, e.g., respond similarly to the corresponding buttons 330, 334 (FIG. 3) of a sticker 120. A wearable 130 (FIG. 7) in emergency status may behave similarly to a sticker 120 in emergency status, e.g., by emitting light and/or sound and/or sending an emergency signal to one or more other devices, as described below.

In an embodiment, a wearable 130 may further comprise a locate button 838, e.g., as FIG. 7 depicts. According to embodiments of the invention, pressing the locate button 838 may cause the wearable to transmit, e.g., one or more signals that may be received by any or all stickers 120 that are paired with the wearable 130 and near to it. The meaning of "near" in this context may depend, e.g., on the effective range transmission protocol and/or the environment (e.g., indoors vs. outdoors), but in an embodiment that uses BLE, the effective range may be just that range that, in a particular environment, allows a BLE connection between a wearable and a sticker.

A sticker 120 that receives the signal may respond, e.g., by entering findable mode as described above.

A wearable 130 in an embodiment of the invention may be powered by one or more rechargeable batteries. Accordingly, a wearable 130 may provide one or more ports, such as a USB-micro port 850, through which the wearable 130 may receive power.

According to embodiments of the invention, a wearable 130 may be capable of finding its location in one or more ways. For example, it may be able to determine its location relative to one or more other devices with known locations (such as, e.g., base stations and/or checkpoint devices such as are described below) using a protocol such as iBeacon®. In an embodiment, the wearable may similarly be able to find its location by detecting, e.g., nearby WiFi® networks with known locations. Other possible ways for a wearable 130 to determine its location according to embodiments of the invention may include, e.g., cell tower triangulation and/or built-in GPS.

In some embodiment, a smart wearable may further comprise a set of status lights to indicate the safe zone in which an individual is present. For example, a set of three lights may be provided to indicate three levels of safety of an individual: in safety zone, close to the border of a safety zone, and outside of safety zone. Alternatively, a set of three lights may be provided to indicate another three levels of safety of an individual: sticker device is connected with the smart wearable, sticker device is disconnected with the smart wearable the second smartphone but is within a defined safety zone, and sticker device is disconnected and outside of a defined safety zone. The foregoing is merely exemplary and it will be understood that the level of safe zones may be further divided to four, five, six, seven, eight, nine, ten or more levels. In another embodiment, safe zones may be defined by a specific geographical radius and a location. In certain embodiments, the geographical radius for a safe zone may be about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, or 2.0 miles. In some embodiments, the location may be pre-set into smart wearable through the cloud servers or manually set using a button of smart wearable as an individual arrives at a destination. In yet another embodiment, a safe time zone may be provided to smart wearable devices by synchronizing with an individual's calendar on a cloud server.

In some embodiments, upon losing connection with a sticker device, a simple wearable device may produce an audio alert, a vibration, or a flashing light to notify the subject of the separation from the medication container. In certain embodiments, a snooze button may be provided to allow a subject to stop the audio alert, vibration, or flashing light for a period of time, for example, 15 minutes. In another embodiment, a subject may program a period of quiet time into the simple wearable device via a smart mobile device to mute the alarm for an extended period of time. In yet another embodiment, a subject may program alarms to be triggered at certain times during the day via a smart mobile device, so that the subject would be reminded to check for a medication container in his or her possession.

In some embodiments, a snooze button (not pictured) may be provided to allow a subject to stop the smart wearable from vibrating for a period of time such as, for example, 15 minutes. In yet another embodiment, an inquiry button (not pictured) may be provided to allow a subject to listen to pre-recorded emergency instructions.

Figure 8A:
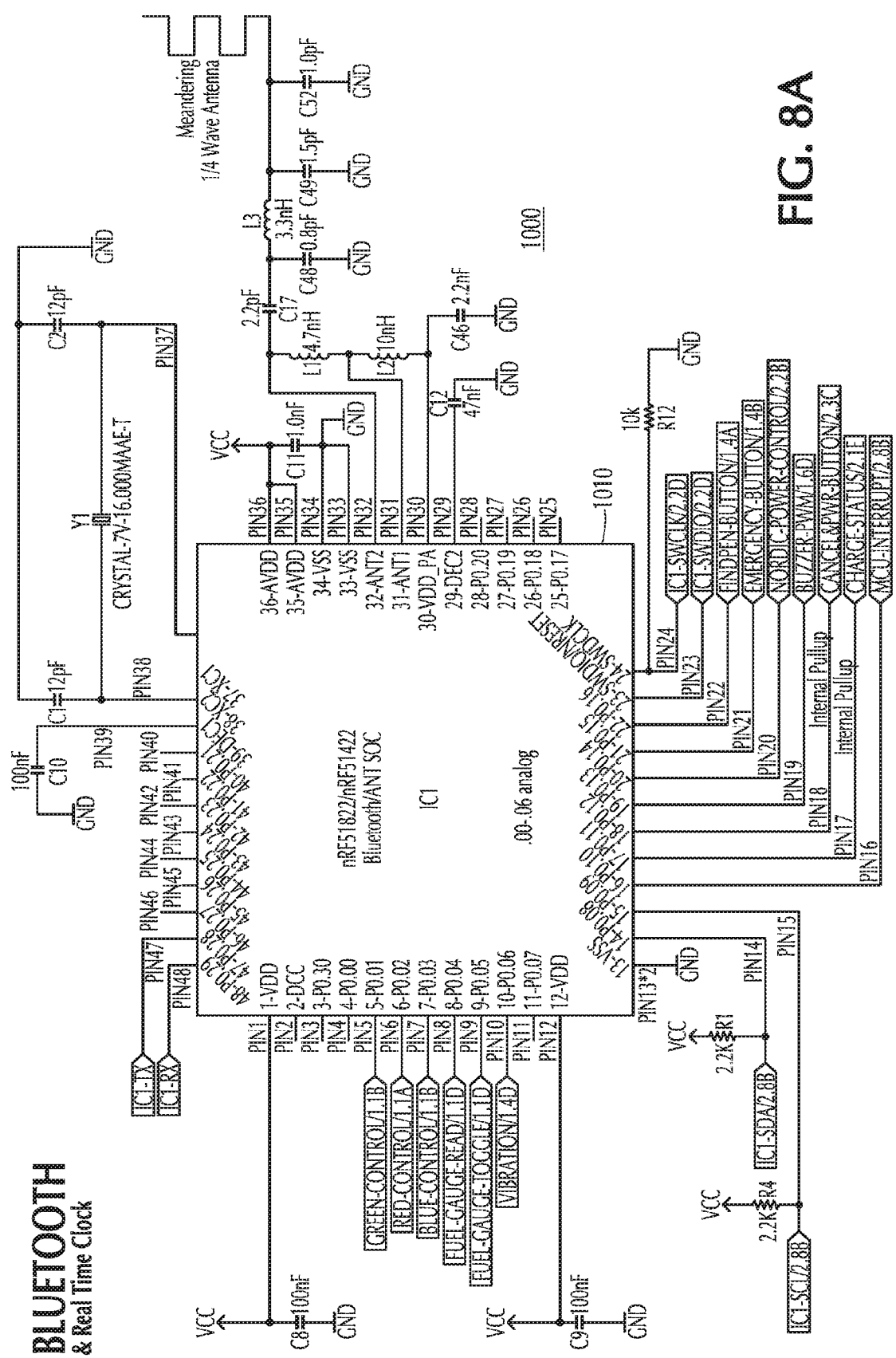
FIGS. 8A-C combine to depict, as a schematic diagram, circuitry implementing a wearable according to an embodiment of the invention.
Figure 8B:
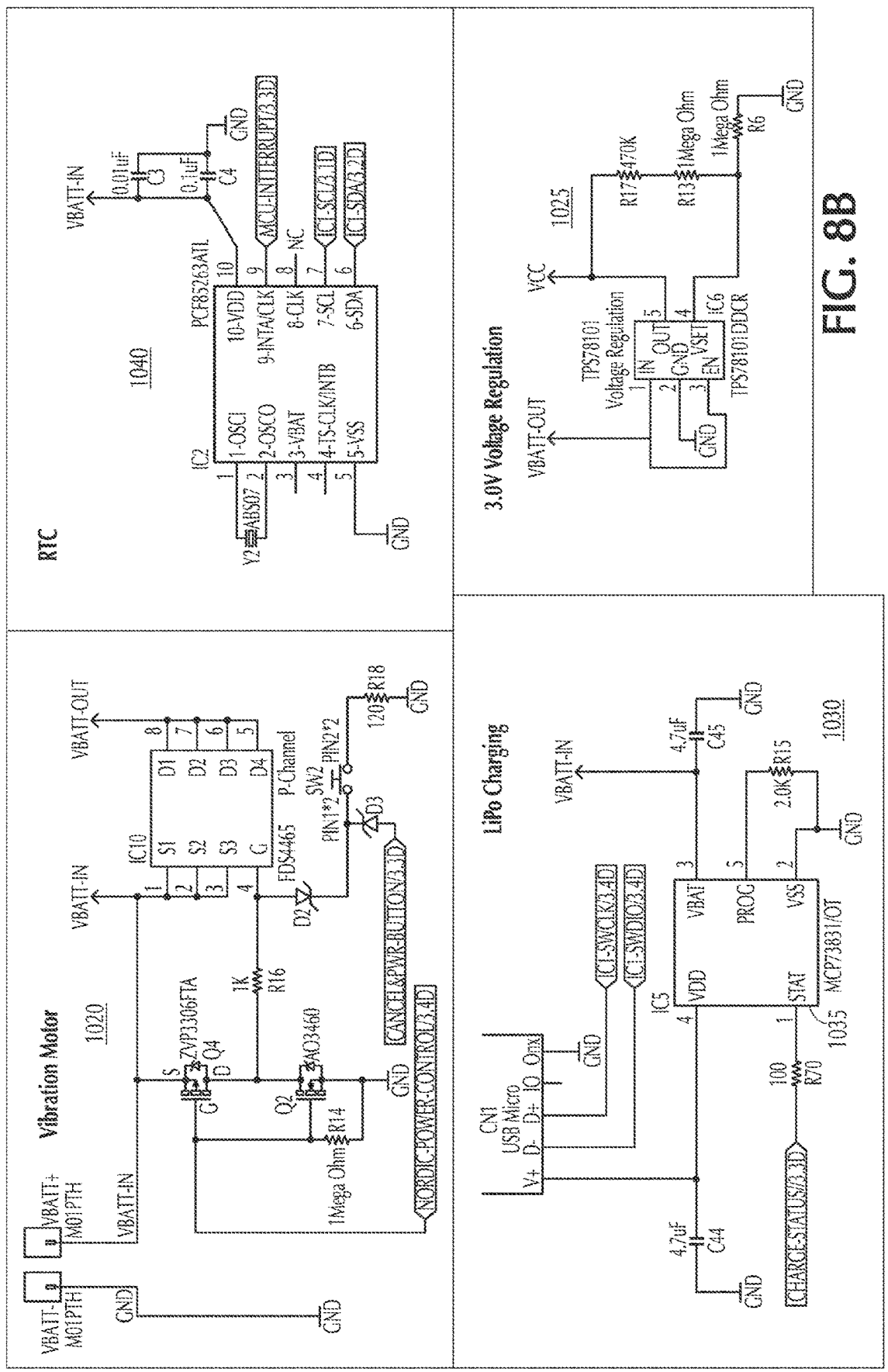
Figure 8C:
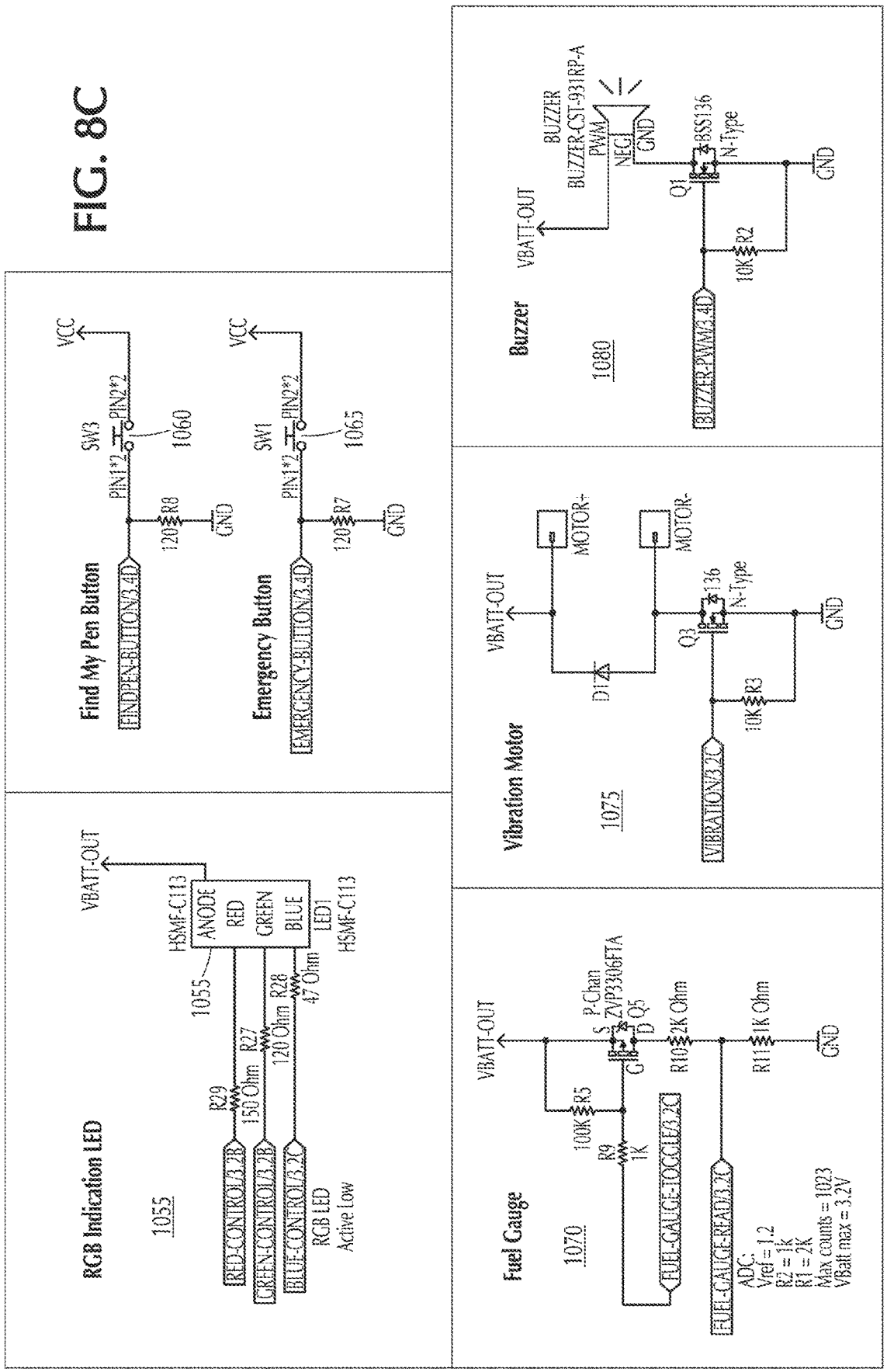

FIGS. 8A-C depict, in the form of circuit schematics, an implementation of a wearable according to an exemplary embodiment of the invention. In an embodiment such as FIGS. 8A-C depict, core logic and wireless systems 1000 may be implemented, e.g., as FIG. 8A depicts and as with the sticker 120, by a Bluetooth® SoC 1010 such as the nRF51422 or nRF51822.

FIG. 8B depicts circuit schematics for additional systems such as may be part of an implementation of a wearable 130 according to an embodiment of the invention. As depicted, the batteries provide input power in connection with battery input circuit 1020 and voltage regulation circuit 1025, and they may be recharged, e.g., through the USB-micro port 850 (FIG. 7), by a circuit 1030 (FIG. 8B) such as the depicted one, which includes a commercially available charge management controller 1035. As depicted, the USB-micro port 850 (FIG. 7) may also be used to program the SoC 1010 (FIGS. 8A-C).

FIG. 8B also depicts a real-time clock circuit 1040 such as may be used in connection with an embodiment of the invention.

FIG. 8C depicts further circuits and components such as may be used to implement a wearable 130 in connection with embodiments of the invention. As depicted, these may include, e.g., a circuit 1050 containing a three-color LED 1055; a button 1060 to activate "Find My Pen" functionality and another 1065 to activate emergency mode; a "fuel gauge" or power measurement circuit 1070; a circuit 1075 to drive a vibration motor; and a circuit 1080 to drive a buzzer.

Figure 9:
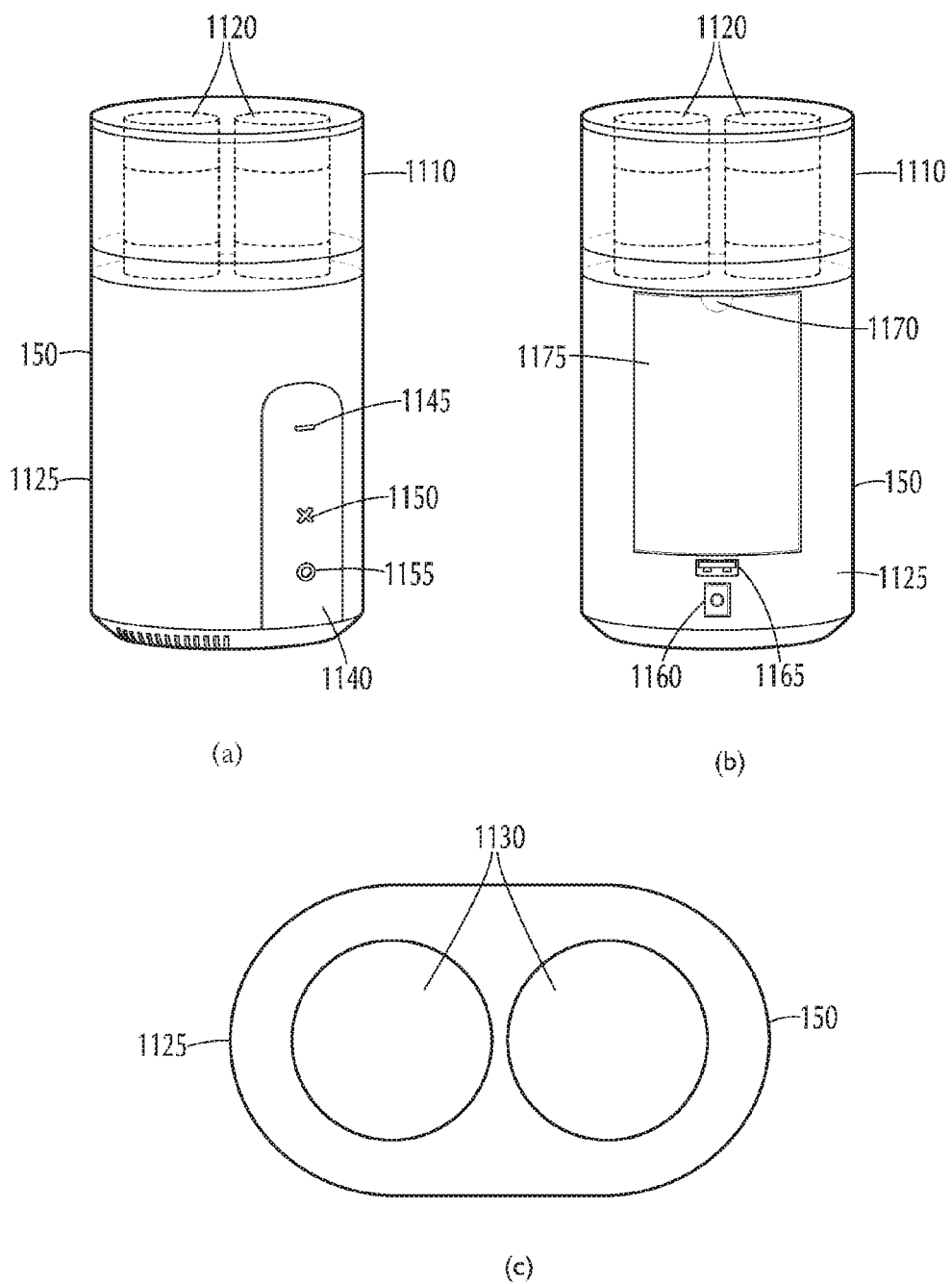
FIG. 9 depicts a home base station according to an embodiment of the invention.

FIG. 9 depicts a home base station 150 according to an embodiment of the invention, showing views (a) from the front, (b) from the rear, and (c) from above. (The view of the home base station from above does not depict a cover 1110, e.g., as described below.) The name "home base station" reflects how this base station 150 may be designed or configured, according to embodiments of the invention, to be suited for installation, e.g., in a subject's home. It will be appreciated, however, that this name does not reflect a necessary limitation; except as explicitly stated otherwise, or as would necessarily be inconsistent with the structure and functions described here, a home base station 150 may be installed and/or used in any desired location.

In an embodiment such as FIG. 9 depicts, a home base station 150 may be capable of receiving and storing two autoinjectors 1120, each with a sticker (not pictured) attached. To accommodate the autoinjectors 1120, the home base station 150 may have a body 1125, and the body may be shaped to include, e.g., two wells 1130, each capable of holding one autoinjector 1120 upright.

In embodiments of the invention the body 1125 may be made, e.g., of thermoplastic, and it may in whole or in part be opaque, translucent, or transparent. In an embodiment, one or more light sources (such as LEDs) (not pictured) may be placed inside the body 1125 so that they may emit light through one or more translucent or opaque regions, thereby making the light visible outside the home base station 150.

A cover 1110 may be provided, e.g., to enclose and/or protect the autoinjectors 1120. The cover 1110 may be wholly or partly transparent and/or translucent, as FIG. 9 depicts, thereby providing a way to determine whether either or both autoinjectors 1120 are in place without removing the cover 1110. In an embodiment of the invention, one or more switches (not pictured) may be placed and configured to detect whether the cover is in place and generate an electrical signal indicating this state.

In an embodiment such as FIG. 9 depicts, a home base station 150 may include, e.g., on the front, a button strip 1140, which may include, e.g., an emergency button 1145, a cancel button 1150, and a "find my pen" button 1155. On the back, a home base station 150 as depicted may include a jack 1160 through which power may be supplied, e.g., from a wall outlet adapter or other source. It may also in an embodiment include a USB jack 1165 that is configured to supply power for charging a device, such as, e.g., a wearable (not pictured).

A home base station 150 in an embodiment of the invention may be configured to be capable of displaying information, e.g., by providing a flat, recessed area 1170 with a clear plastic protective cover 1175 that leaves an opening at the top of the recessed area 1170. Information such as instructions for using the device and/or responding to apparent anaphylaxis may be printed, e.g., on a card (not pictured) and placed in the recessed area 1170, behind the protective cover 1175. The home base station 150 may be configured so that the contents of the recessed area 1170 may easily be removed and replaced, and in an embodiment, the card may carry information on both sides, or a booklet (not pictured) may be provided for storage in the recessed area 1170.

In an embodiment of the invention, a home base station 150 may be capable of detecting whether either or both wells 1130 contains, e.g., an autoinjector. For example, the presence or absence of an autoinjector or other object may be detected through a mechanical switch (not pictured), e.g., in the wall of the well 1130 or at the bottom of it. The presence or absence of an electrical signal in a circuit corresponding to a well 1130 may indicate to other components in an embodiment the presence or absence of an autoinjector (or the converse).

FIG. 9 depicts a home base station 150 designed to be used with autoinjectors 1125, e.g., for epinephrine. It will be appreciated that a home base station 150 in embodiments of the invention may be configured to receive and store other types of medication containers and/or other types of objects (not pictured); in such embodiments, the shape of either or both wells 1125 may vary, e.g., to correspond to the container or object (or part thereof) that the well 1125 is meant to hold. In other embodiments of the invention, one or more of the wells 1125 may be replaced by other means of holding an object, including (but not limited to) hooks, shelves, and or magnets, among many other possibilities.

Further, a home base station 150 according to embodiments of the invention need not be configured to hold up to two objects, but it may be configured, e.g., to receive and store any desired number of objects. It may further be configured to receive and store multiple types of objects, e.g., by including one or more wells 1125 and/or other means capable of holding more than one kind of object in a particular space and/or by having multiple spaces, each configured to receive and store one or more different kinds of objects.

Figure 10A:
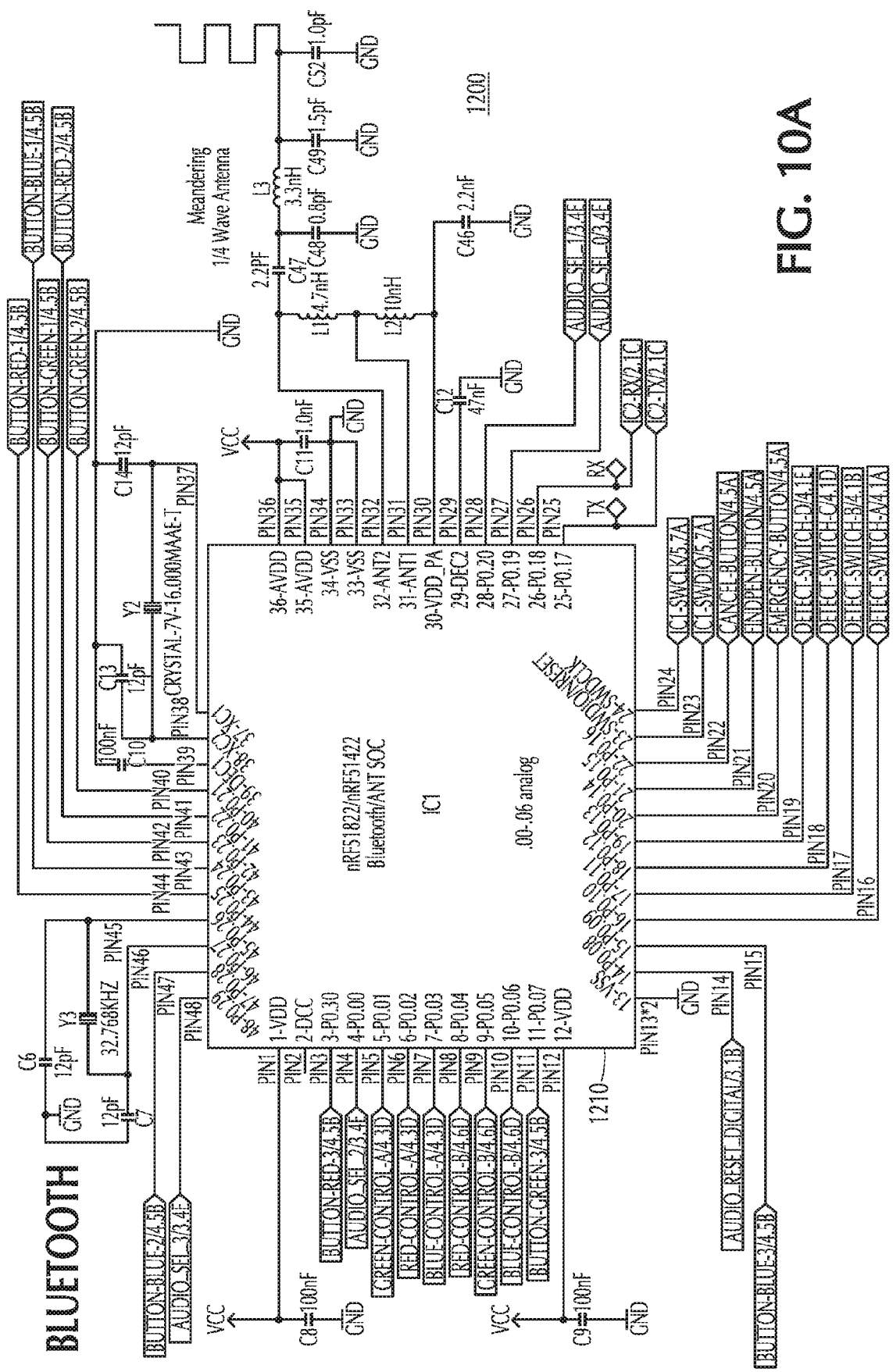
Figure 10B:
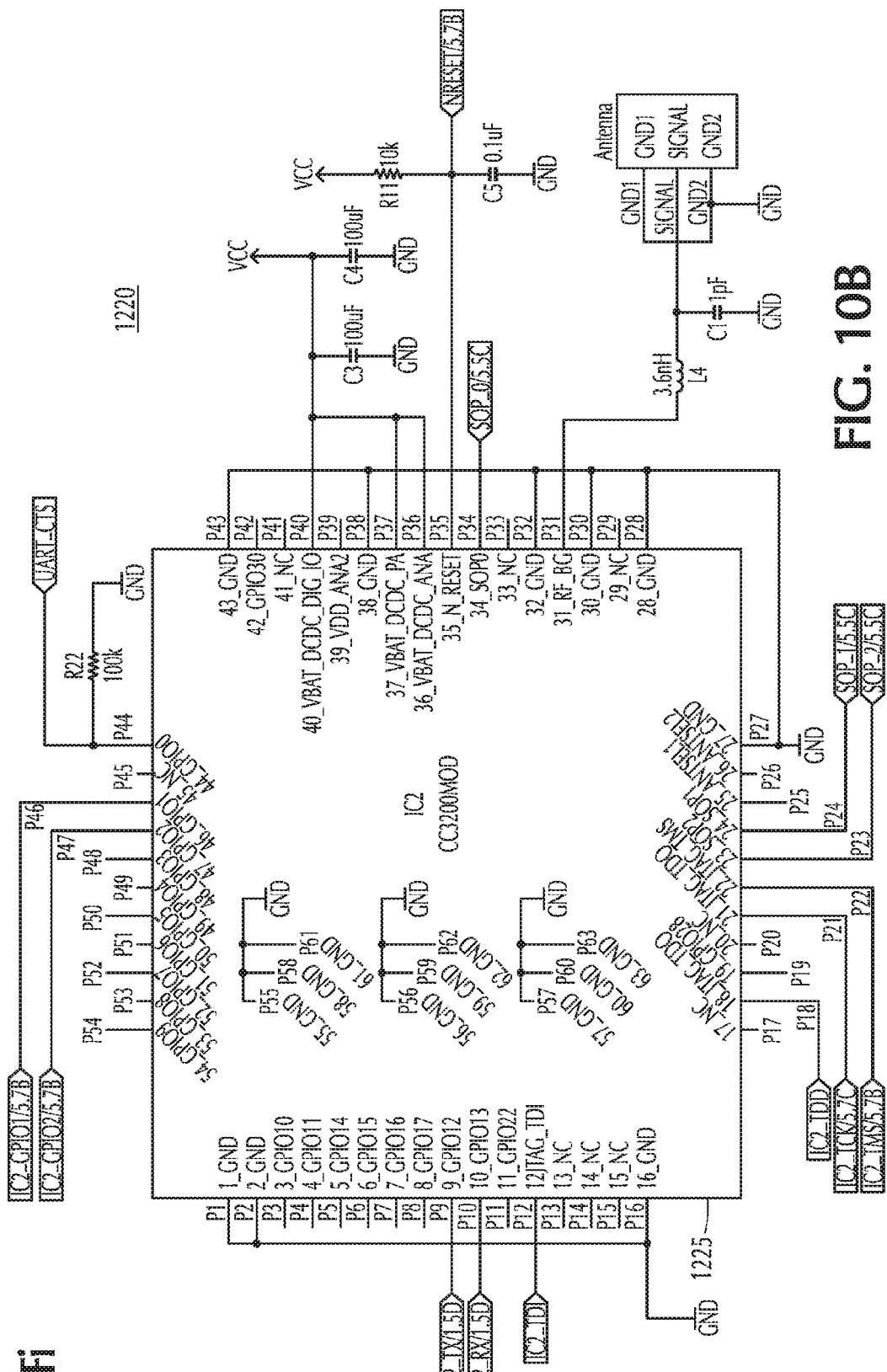

FIGS. 10A-F depict, in the form of circuit schematics, an implementation of a home base station 150 according to an embodiment of the invention. As FIG. 10A depicts, and as with the sticker 120 and wearable 130 discussed previously, core logic and Bluetooth®-related wireless systems 1200 may be implemented with a Bluetooth® SoC 1210 such as the nRF51422 or nRF51822. In an embodiment of the invention, a separate system 1220 may implement Wi-Fi®, e.g., as FIG. 10B depicts, using a separate microcontroller 1225 such as the CC3200MOD, commercially produced by Texas Instruments™.

Figure 10C:
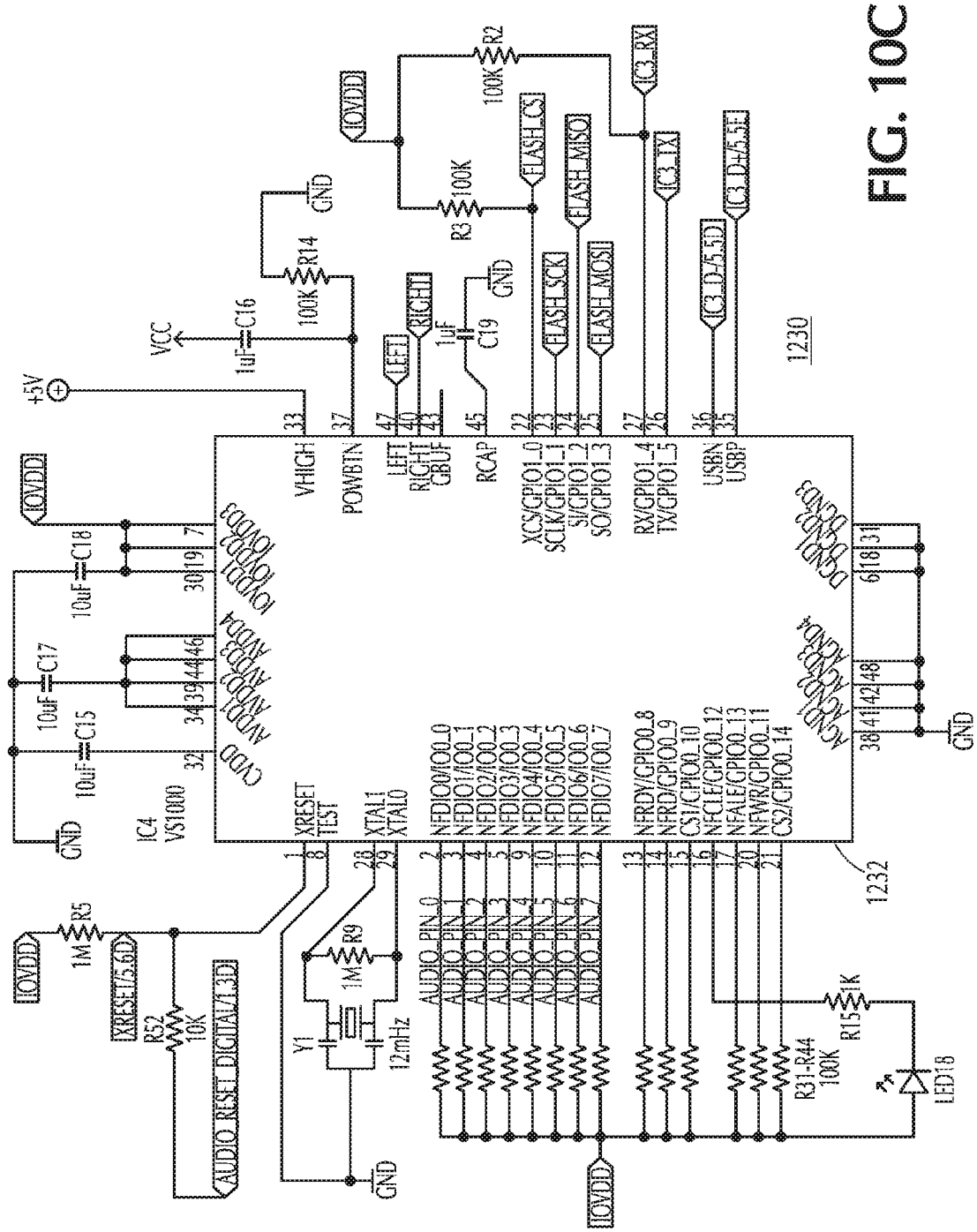
Figure 10D:
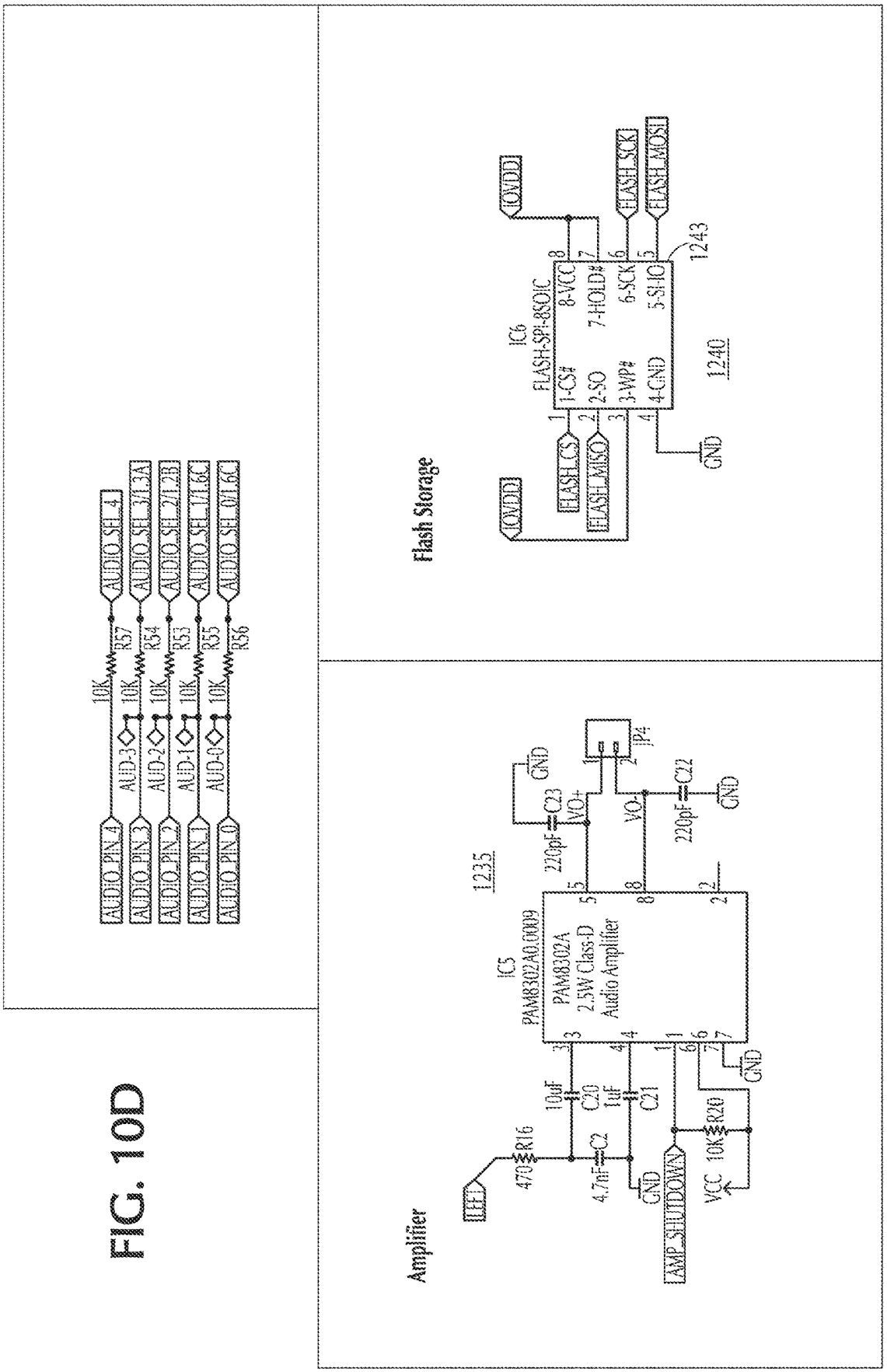

FIG. 10C and FIG. 10D depict systems for generating and outputting sound according to embodiments of the invention. In an embodiment such as FIGS. 10A-F depict, a system 1230 containing, e.g., a VS1000 Ogg Vorbis Player System circuit 1232, which may generate audio for playback, and the audio may be supplied, e.g., to an amplifier circuit 1235 to drive a component such as a speaker (not pictured), for example, for playback. A storage circuit 1240, e.g., as depicted, may include a serial flash circuit 1243 that stores digitized audio for playback.

Figure 10E:
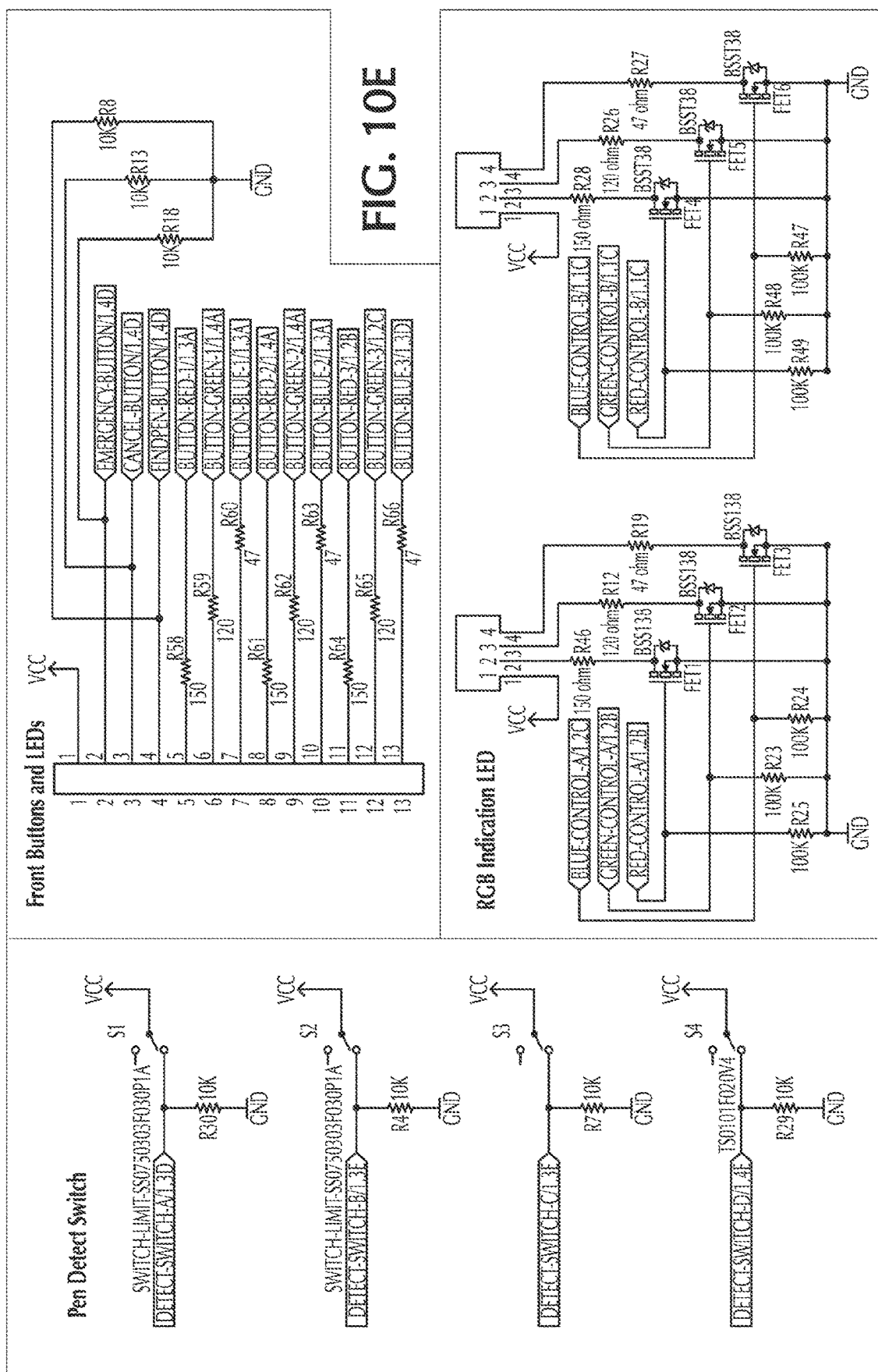

FIG. 10E depicts circuits for accepting input, e.g., from switches and/or buttons, and for driving RGB LEDs for visual output, according to embodiments of the invention. FIG. 10F depicts further support circuits, according to an embodiment of the invention, for receiving and supplying power 1260, 1265, for programming and debugging 1270, 1275 the Bluetooth® 1210 and/or Wi-Fi® 1225 microcontrollers, and for loading audio files 1280 to the decoder 1232.

As discussed in this disclosure, a home base station 150 according to embodiments of this invention may, e.g., determine a location of one or more other devices, including, e.g., one or more stickers and/or wearables. It may in some cases be desirable to have a device in a location that may perform these functions without necessarily being able to store any autoinjectors. Thus, in an embodiment of the invention, a virtual checkpoint device may be provided. In embodiments, the virtual checkpoint device may be simply a home base station that has been modified to remove its storage capacity.

Alternatively, in embodiments of the invention, a virtual checkpoint device may comprise, e.g., a communication module and an alarm configured to be triggered upon a determination that a wearable is present without a sticker device. The alarm may be an audible alert, a tactile alert, or a visual alert. As with a home base station, a virtual checkpoint device may determine its location, e.g., via GPS or other direct means and/or via IP-based geolocation. In some embodiments, a virtual check point device may be installed near a door of a subject's house, near a school bus door, near the gate of a school, a daycare facility, or a camp. In embodiments, a virtual checkpoint device may be powered, e.g., by AC mains, directly or via a separate power adapter, and in embodiments, a virtual checkpoint device may be powered by one or more rechargeable and/or non-rechargeable batteries.

Figure 11:
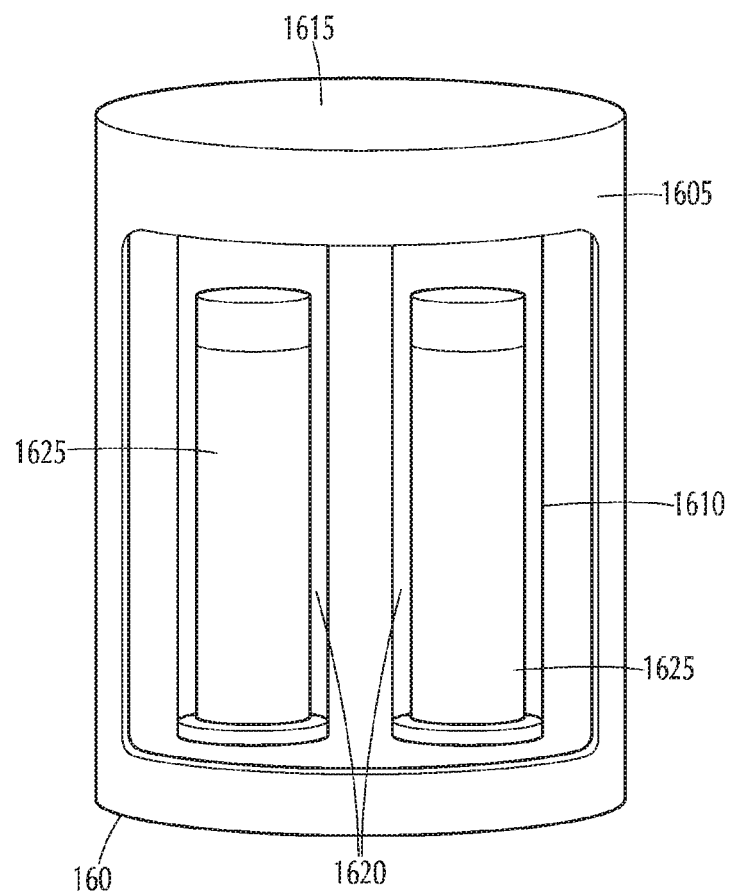
FIG. 11 depicts a public base station according to an embodiment of the invention.

FIG. 11 depicts a public base station 160 according to embodiments of the invention. As depicted, the public base station 160 includes a body 1605 and a cover 1610, which may be connected to the body 1605, e.g., by one or more hinges (not pictured), such that the cover may be opened by lifting it. The cover 1610 may be made, e.g., of transparent plastic to display the public base station's contents while protecting them. In an embodiment of the invention, one or more switches (not pictured) may be placed and configured to detect whether the cover is in place and generate an electrical signal indicating this state.

In embodiments of the invention, the body 1605 may be made, e.g., of opaque or translucent thermoplastic or other material. In an embodiment of the invention, some or all of the upper surface 1615 of the body may be translucent, e.g., to allow indicator lights contained within the public base station 160 to be seen on the outside.

In several ways, a public base station 160 according to embodiments of the invention may resemble, e.g., a home base station 150 as described above. For example, as depicted, the public base station 160 includes two wells 1620 or other receptacles, each configured to hold a single autoinjector 1625 with a sticker (not pictured) attached. It will be appreciated that a public base station 160 in embodiments of the invention may be configured to receive and store other types of medication containers and/or other types of objects (not pictured); in such embodiments, the shape of either or both wells 1620 may vary, e.g., to correspond to the container or object (or part thereof) that the well 1620 is meant to hold. In other embodiments of the invention, one or more of the wells 1620 may be replaced by other means of holding an object, including (but not limited to) hooks, shelves, and or magnets, among many other possibilities.

Further, a public base station 160 according to embodiments of the invention need not be configured to hold up to two objects, but it may be configured, e.g., to receive and store any desired number of objects. It may further be configured to receive and store multiple types of objects, e.g., by including one or more wells 1620 and/or other means capable of holding more than one kind of object in a particular space and/or by having multiple spaces, each configured to receive and store one or more different kinds of objects.

In an embodiment of the invention, a public base station 160 may be capable of detecting whether either or both wells 1620 contains, e.g., an autoinjector. For example, the presence or absence of an autoinjector or other object may be detected through a mechanical switch (not pictured), e.g., in the wall of the well 1620 or at the bottom of it. The presence or absence of an electrical signal in a circuit corresponding to a well 1620 may indicate to other components in an embodiment the presence or absence of an autoinjector (or the converse).

Despite the differences in shape and/or function between a public base station 160 and a home base station 150, the electronics within a public base station 160 according to embodiments of the invention may substantially resemble those of the embodiments of the home base station 150 described above. The differences in operating environments and function between the two kinds of base stations in embodiments of the invention, e.g., such as are described below may lead to some adaptations of the circuits to the different environments, but such adaptations will be apparent to a person skilled in the art who is familiar with those functions and environments. For example, a public base station 160 may in an embodiment of the invention be permanently wired to AC mains, in which case the circuitry may incorporate an AC-to-DC adapter, e.g., as is known in the art.

As FIG. 1 depicts, according to embodiments of the invention, functions and services may be provided using, e.g., one or more interacting stickers 120, wearables 130, home base stations 150, and/or public base stations 160, which may function, e.g., as described above. Some or all functions, services, or both, may also be provided according to embodiments of the invention in connection with one or more user devices, such as, e.g., smartphones with a mobile app 140. In embodiments of the invention, one or more such devices may, e.g., coordinate and/or administer these functions and services, which may further, in embodiments of the invention, be provided in connection with a support infrastructure 170.

In some embodiments, a mobile app (not pictured) may comprise a user interface, which is in communication with a session manager, a communication manager, a content manager, and a Bluetooth® device manager. The communication manager may further be in communication with a REST application programming interface (API), and a state manager. The Bluetooth® device manager may be in communication with an iOS™ Bluetooth® Low Energy (BLE) application programming interface (API) and a state manager. The state manager may be in communication with a data abstraction layer and the user interface. The mobile app may further comprise a Core Data database that stores user profile data, device data, a local event log, and allergen data. The Core Data database may be in communication with the data abstraction layer, which is in turn in communication with the session manager.

Functions and services according to embodiments of the invention may be further illustrated, e.g., in connection with description of the operation of an exemplary mobile app 140 according to an embodiment of the invention. Further, the description of a mobile app 140 according to an embodiment may assume or refer to certain conventions of certain operating environments; for example, a description may assume or refer to a user interface component and/or convention associated with iOS™. The description is not in any way meant to be limited by this, however, and it will be appreciated that an application in an embodiment of the invention may exhibit the disclosed characteristics, e.g., in other operating environments and/or other devices and/or types of devices. Where appropriate, a user may interact with (or according to) an embodiment of the invention using a device other than a mobile device, e.g., with a person computer using a Web browser and/or other software.

The discussion of a mobile app 140 according to embodiments of the invention may refer extensively to screens that such an app 140 may cause a mobile device to display. It will be appreciated, however, that many applications are intended to display more information in a single page or other display than conveniently may fit within the display device incorporated into a mobile device, so many mobile operating environments support scrolling. With this in mind, content that may be too large to be entirely displayed on a screen at once may nonetheless be referred to as part of a single screen if conventional scrolling may suffice to bring different parts of that same content into view. Some descriptions of particular screens may refer explicitly to scrolling, but the lack of such explicit reference should not be taken to mean that scrolling does not occur, if the context reasonably requires it to.

Figure 12:
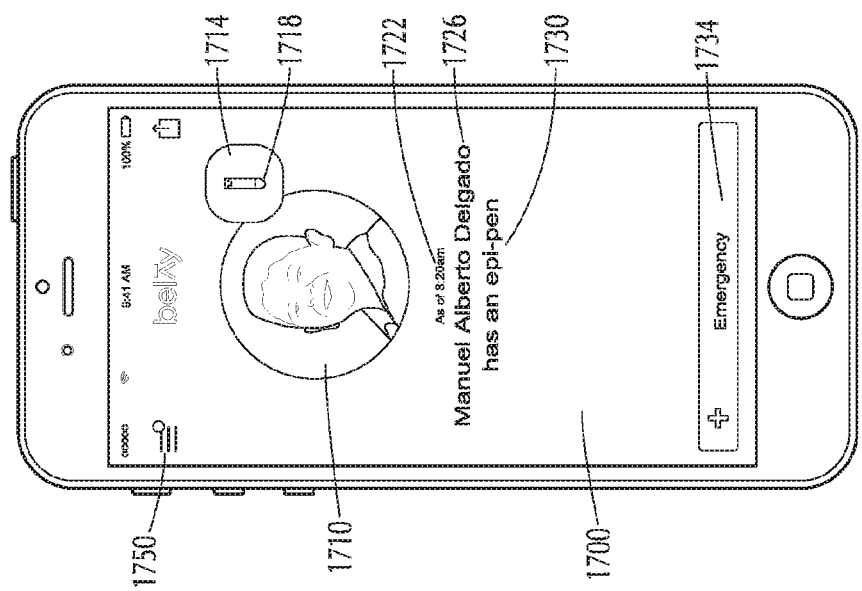

FIG. 12 depicts examples of a home screen 1700 of a mobile app 140 according to an embodiment of the invention. As depicted, the home screen 1700 includes an image 1710 (here, a photo) representing the subject and, superimposed on that image 1710, another image 1714 representing a tracked object, here, an EpiPen® autoinjector. As depicted, the image 1714 is an icon that includes a symbolic representation 1718 of an autoinjector, but a photo may also serve. Similarly, the image 1710 representing the subject need not be a photo of the subject and may in an embodiment be a photo of something other than the subject, or it may be some other image.

A home screen 1700 according to an embodiment of the invention may include status information. For example, as depicted, the home screen 1700 indicates a time 1722, the name of the subject 1726, and text 1730 representing that, at the indicated time 1722, the subject had an EpiPen®. In an embodiment of the invention, if the mobile app 140 is installed on a device that belongs to the subject or is otherwise personally associated with subject, the subject's name 1726 may be replaced by the word "you" (not pictured).

The depicted home screen 1700 also includes a slider 1734, labeled "Emergency". By activating this slider 1734, the user can enter emergency mode, signifying that the subject may be having a severe allergic reaction, which may be anaphylaxis.

The home screen 1700 indicates that the subject "has" an EpiPen®. In embodiments of the invention, this may mean that an autoinjector is known to be reasonably accessible to the subject by some standard, as discussed elsewhere.

If the system cannot determine that the subject has a reasonably accessible autoinjector, however, the mobile app 140 may indicate this.

Figure 13:
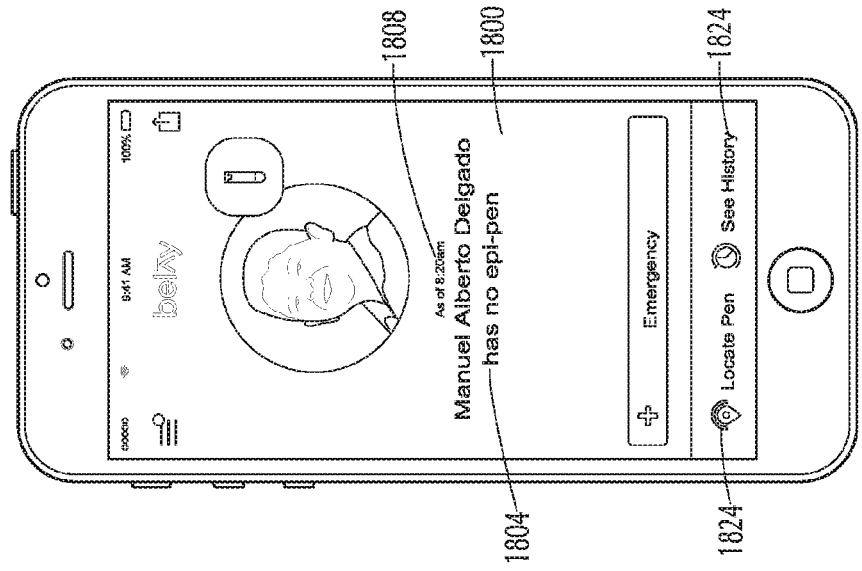
FIGS. 12-21 depict user interface screens for a mobile app according to an embodiment of the invention.

FIG. 13 depicts a modified home screen 1800 that includes text 1804 indicating that, at the indicated time 1808, the subject does not have an autoinjector. In this circumstance, the modified home screen 1800 may display additional user interface elements. For example, a button 1820 labeled "Locate Pen" may be presented, which may cause the mobile app 140 to attempt in various ways to locate a nearby autoinjector. Another button 1824, labeled "See History" may cause display of information about the subject, including, e.g., information about the subject's location, access to autoinjectors, and/or entry into and/or exit from emergency mode.

Figure 14:
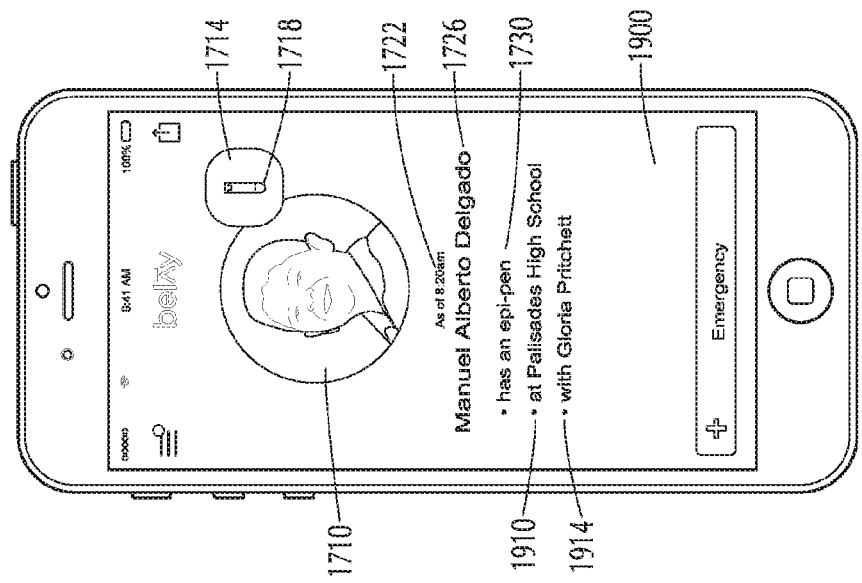

According to embodiments of the invention, a home screen of a mobile app 140 may present additional information that may be useful or desirable in some way. For example, FIG. 14 depicts a home screen 1900 according to an embodiment of the invention that, in addition to the information depicted in FIG. 12, also indicates 1910 the subject's location and identifies 1914 a member of the subject's team who is at the indicated location with the subject.

Figure 15:
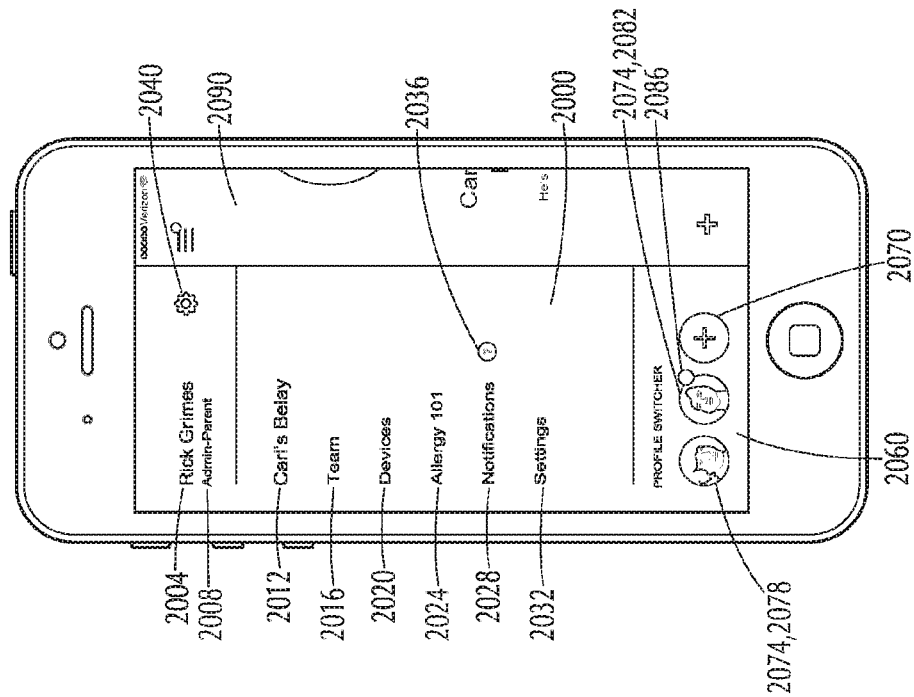

To enhance navigation with the mobile app 140, according an embodiment of the invention, screens—including, e.g., the home screen 1700 (FIG. 12)—may include a menu button 1750. When this button 1750 is selected, the mobile app 140 may present a navigation menu 2000, e.g., as FIG. 15 depicts.

As depicted, a navigation menu 2000 may identify the user, e.g., by name 2004, and indicate one or more of the user's roles 2008 within the subject's team. The navigation menu 2000 may also present, e.g., a label 2012 that identifies the subject and/or team; this label 2012 may be the subject's name, or it may include part or all of the name, but it may in an embodiment of the invention be configured to be any text that a user believes to be useful.

Navigation options according to an embodiment of the invention may include, e.g., "Team" 2016; "Devices" 2020; "Allergy 101" 2024; "Notifications" 2028; and "Settings" 2032. In an embodiment of the invention, the "Notifications" option 2028 may include, e.g., an alert 2036, which may indicate, e.g., the number of notifications received and/or the number of received notifications that remain unread. As described below, each menu item may lead, e.g., to a screen presenting information and/or functions associated with the respective menu item.

A settings icon 2040 may also be provided. In an embodiment of the invention, this icon may be provided, e.g., only for users who have some or all administrative privileges with regard to a team, and may enable navigation, e.g., to a screen that presents administrative information and/or functions to those users. Alternatively, a settings icon 2040 may enable navigation, e.g., to a screen such as the "Settings" 2032 menu item enables navigation to.

According to embodiments of the invention, a user may be a member of two or more teams. Information associated with the user's membership in a particular team may be referred to as a "profile", and, in an embodiment of the invention, a navigation menu may include a profile switcher 2060. As depicted, a profile switcher 2060 may include an "add profile" button 2070 for use, e.g., when the user wishes to join another team.

For each of the user's existing profiles, the profile switcher 2060 may include a user interface element allowing the user to select one of the profiles to activate. For example, in an embodiment such as FIG. 15 depicts, the profile switcher 2060 includes an image 2074 for each profile; in an embodiment, this may be, e.g., the same image 1710 (FIG. 12) that represents the relevant subject, although possibly reduced for size. The currently active profile may be indicated, e.g., by highlighting the image 2078 associated with it and/or by dimming the other images 2082. A visual alert (as depicted, a red circle) 2086 may indicate in an embodiment that a profile has one or more unread notifications associated with it.

According to an embodiment, the navigation menu 2000 may be dismissed, e.g., by means conventional in the operating environment. For example, using a mobile app 140 on an iPhone®, a user may dismiss the navigation menu, e.g., by tapping on the screen in the area 2090 outside of the navigation area.

Figure 16:
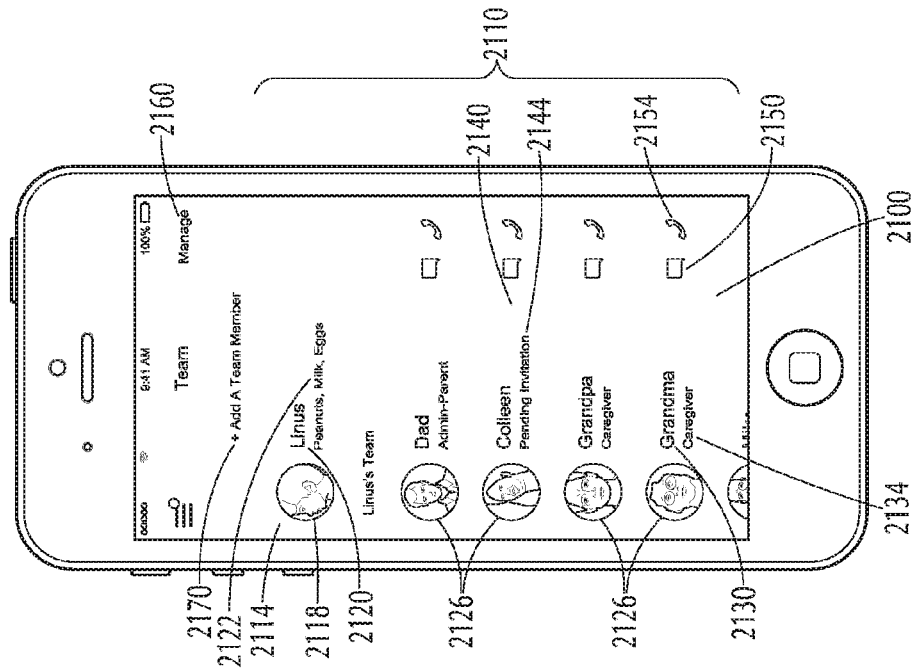

FIG. 16 depicts a team list screen 2100 according to an embodiment of the invention, such as a mobile app 140 might display following selection of "Team" 2016 (FIG. 15) from the navigation menu 2000. The depicted screen includes a list 2110 of members of the subject's team, and begins with a list item 2114 corresponding to the subject. The list item 2114 comprises the subject's icon 2118 and name 2120 and a list 2122 of the subject's allergies.

Below the subject's list item 2114, the list 2110 includes additional list items 2126 for each member of the subject's team. In an embodiment such as FIG. 16 depicts, each additional list item 2126 includes a name 2130 and a list 2134 of the member's roles. The roles may include, e.g., one or more of "Admin", "Parent", and "Caregiver", and/or others, depending on the embodiment.

A person who has been invited to join a subject's team, but has not yet done so, may have a list item 2140. In an embodiment such as FIG. 16 depicts, such a person's list item 2140 may have the words, e.g., "Pending invitation" 2144, in place of the person's roles.

Embodiments of the invention may support messaging, e.g., as described elsewhere. In such embodiments, a list item 2126 may include, e.g., an icon 2150 that, when selected, initiates a text messaging session between the user and the selected team member. In an embodiment, text messaging may proceed, e.g., via a user interface and/or facilities such as may be familiar in the art. A list item 2154 may allow initiation of a voice conversation with the selected team member, e.g., as a cellular telephone call or otherwise.

Similar icons for text and/or voice communication (not pictured) may appear in the list item 2114 for the subject in embodiments of the invention. It will be appreciated, however, that a team list screen 2100 such as FIG. 16 depicts may be presented specifically to the subject, and therefore the communication icons may be included in only list items 2126 corresponding to other users. Conversely, in a team list screen 2100 presented to a user other than the subject, the icons 2150, 2154 may be absent from that's users own list item 2126 but present in the subject's list item 2114.

In an embodiment of the invention, a team list screen 2100 presented to an administrative user may include one or more elements allowing performance of administrative tasks. For example, as FIG. 16 depicts, the team list screen 2100 includes a button 2160 labeled "Manage". When selected, this button may modify the list to include controls (not pictured) that allow the user, e.g., to delete team members and/or to modify their roles and/or privileges.

Figure 17:
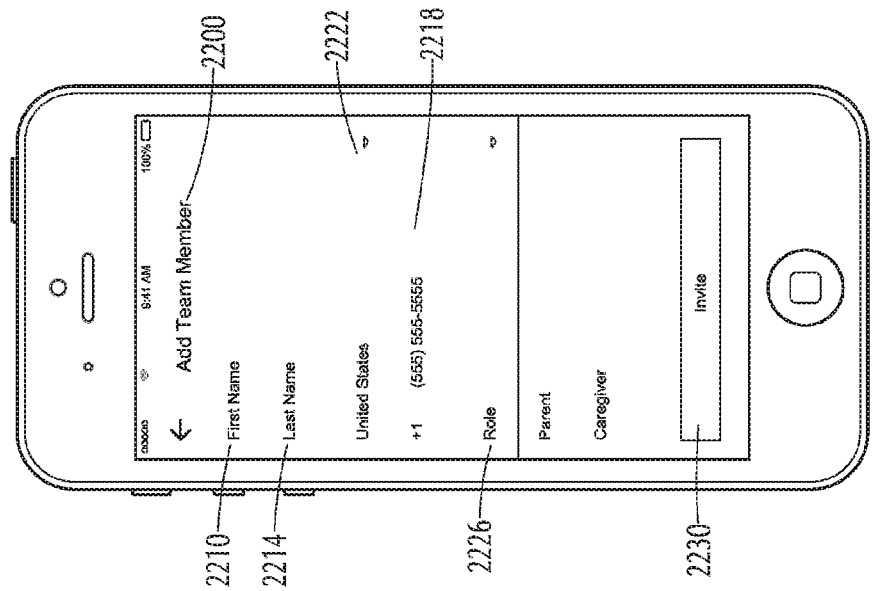

An administrative user may in an embodiment of the invention also be presented with a control 2170 that allows the user to add a team member. When selected, the mobile app 140 may present, e.g., an add team member screen 2200, as FIG. 17 depicts. As depicted, an add team member screen 2200 according to an embodiment of the invention may include a form that includes, e.g., fields for the invitee's first name 2210, last name 2214, and telephone number 2218. The form may comprise a drop-down 2222 for selecting the invitee's country and another 2226 for assigning the invitee one or more roles, which may or may not, depending on the embodiment, include the administrative role.

The form may be submitted by selecting, e.g., a button 2230 labeled "Invite", as depicted. In an embodiment of the invention, submitting this form may cause, e.g., a text message including a hyperlink (not pictured) to be sent to the invitee. When selecting the hyperlink, a browser may open on the invitee's device, and the invitee may then have the opportunity to accept the invitation and join the subject's team.

Figure 18:
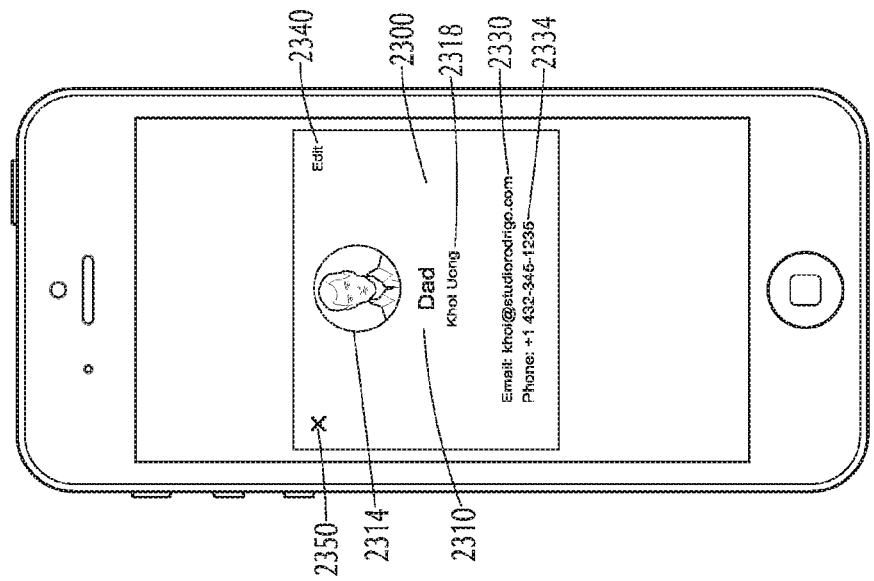

Returning to FIG. 16, a list item 2126 may enable navigation to a profile for the team member associated with the list item 2126. For example, FIG. 18 depicts a profile screen 2300 according to an embodiment of the invention. As depicted, the profile screen 2300 includes the team member's name 2310 and user picture 2314. The depicted profile screen 2300 also includes the team member's full name 2318. Also as depicted, the profile screen 2300 may include the team member's contact information; for example, it may include the team member's email address 2330 and telephone number 2334.

Team members may be able to edit their own profiles. For example, as FIG. 18 depicts, a button labeled "Edit" 2340 may be provided, and selecting it may cause the mobile app to present one or more screens (not pictured) that allow the user to edit the profile. In embodiments, the Edit button 2340 may be absent when viewing other team members' profiles.

As depicted, the profile screen 2300 presents an icon 2350 that, when selected, may dismiss the profile screen 2300 and return the user, e.g., to the team member list screen 2100 or other screen.

Figure 19:
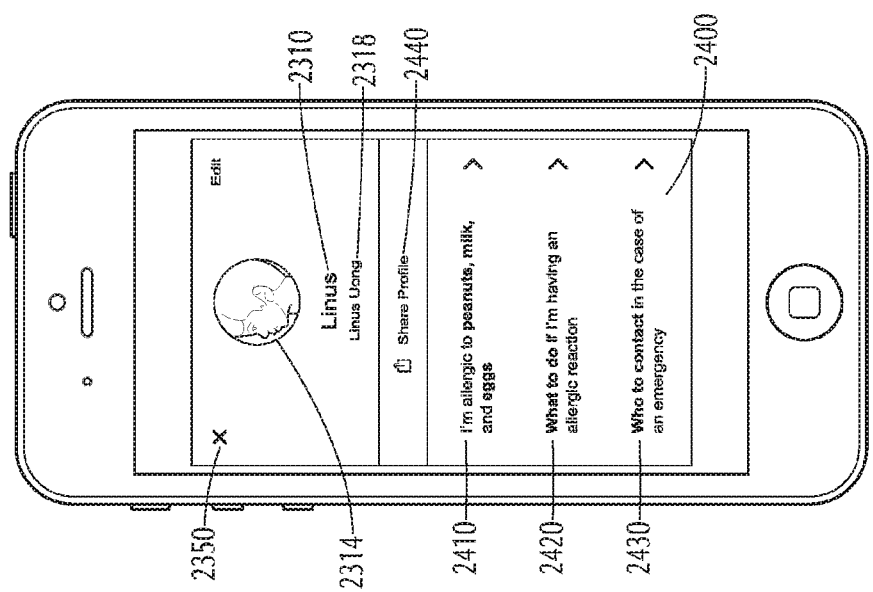

FIG. 19 depicts a subject's profile screen 2400 according to an embodiment of the invention. Much of the information is the same as that presented on a team member's profile screen 2300 (FIG. 18), although in the view that FIG. 19 depicts, some of the similar information has been scrolled out of view to make room for other items. The subject's profile screen 2400, in an embodiment of the invention such as FIG. 19 depicts, may also include information relevant to the subject's allergy (not pictured) and/or one or more tools for navigating to such information.

For example, as depicted, the subject's profile screen 2400 includes a summary list 2410 of the subject's allergies that, when selected, may lead to a display of additional information about those allergies (not pictured). The profile screen 2400 may also include a tool 2420 leading to instructions (not pictured) on what to do if the subject is having an allergic reaction and/or a tool 2430 leading to a display (not pictured) of team members and/or others to be contacted in case of an allergic emergency.

The subject's profile screen 2400, in an embodiment such as FIG. 19 depicts, may include a button or other control 2440 labeled "Share Profile". When selected, this may cause, e.g., the mobile app to share the user's profile, e.g., with one or more other users, either directly or via support infrastructure.

Figure 20:
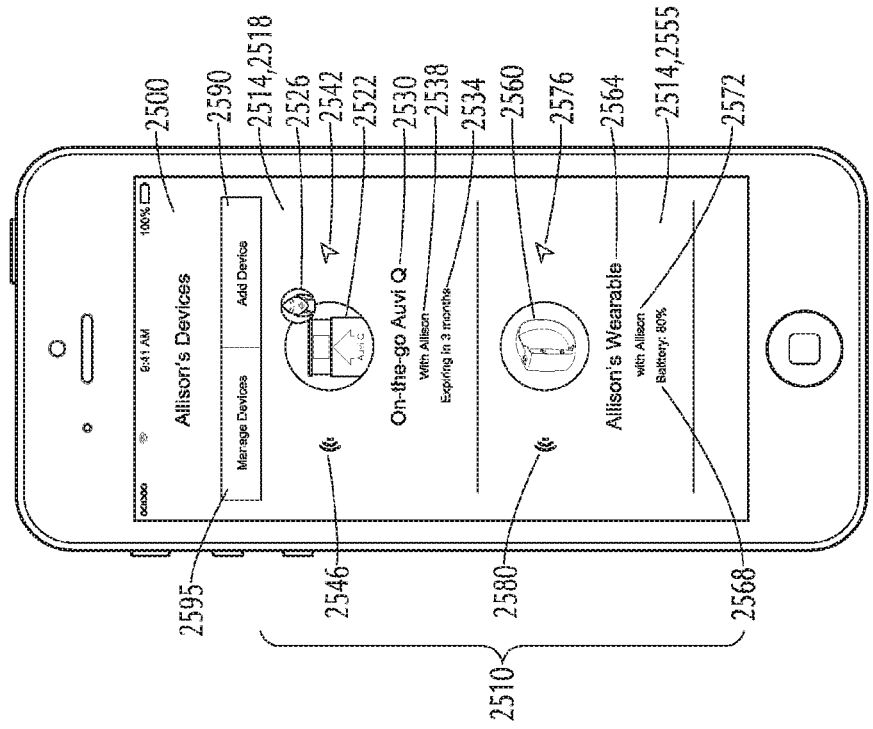

The navigation menu 2000 (FIG.) in an embodiment of the invention includes a "Devices" 2020 menu item. In an embodiment of the invention, selection of that item may cause a mobile app 140 to present, e.g., a devices list screen 2500 such as FIG. 20 depicts. As depicted, the devices list screen 2500 includes a list 2510 of entries 2514 for devices (e.g., stickers 120 and wearables 130) that have been associated with the subject (named "Alison"). (Note that in the following discussion, for brevity, reference may be made to an autoinjector that is associated with the subject; unless explicitly stated otherwise, the association may be in a strict sense between the subject and a sticker 120 that is affixed to the autoinjector.)

The list of devices 2510, as FIG. 20 depicts, includes two visible entries 2514 for devices, although more than two devices may commonly be associated with a single subject, and it may be assumed that entries for additional devices may be brought into view, e.g., by scrolling the displayed part of the list 2510 down.

As depicted, one entry 2518 corresponds to an Auvi-Q® epinephrine autoinjector. This entry 2518 includes an image 2522 that represents the autoinjector and, superimposed on it, a small version 2526 of the subject's user picture. The entry also includes a name 2530 associated with the autoinjector (here, "On-the-go Auvi Q") and the estimated or actual time remaining 2534 until the autoinjector will reach the manufacturer's expiration date. In an embodiment of the invention, selecting the entry 2518 (e.g., by tapping on the image 2522 that represents the autoinjector) will cause the mobile app 140 to present additional details about the autoinjector.

As FIG. 20 depicts, the autoinjector's location is known, at least in that the autoinjector is known to be sufficiently close to the subject to be considered "with" her, and the entry 2518 indicates that status 2538. In embodiments of the invention, if the location of the autoinjector were not known, or if it were known to be separated from the subject, the entry 2518 would indicate that status (not pictured) instead.

The depicted entry 2518 includes an arrow-shaped icon 2542 that when selected, in an embodiment of the invention, causes the mobile app 140 to display a map view that indicates the location of autoinjector, if known, and may additionally indicate locations of one or more other devices, including e.g., other autoinjectors, wearables, and/or base stations, among other possibilities. Another icon 2546, when selected, will attempt to put the autoinjector into "Find My Pen" mode, e.g., as described elsewhere.

The second visible entry 2555 in the list 2510 corresponds to a wearable that is associated with the subject, Allison. As with the autoinjector, the entry 2555 for the wearable includes an image 2560 that represents the wearable and a name 2564 associated with the wearable (here, "Allison's Wearable"). In an embodiment of the invention, selecting the entry 2555 (e.g., by tapping on the image 2560 that represents the wearable) will cause the mobile app 140 to present additional details about the wearable.

The depicted entry 2555 includes a battery strength indicator 2568: as depicted, the wearable's battery is reported to be at 80% of a full charge.

As FIG. 20 depicts, the wearable's location is known, at least in that the wearable is known to be sufficiently close to the subject to be considered "with" her, and the entry 2555 indicates that status 2572. In embodiments of the invention, if the location of the autoinjector were not known, or if it were known to be separated from the subject, the entry 2572 would indicate that status (not pictured) instead. Alternatively, in an embodiment of the invention, the location of the wearable could be used as a marker of the subject's location; in such an embodiment, the meaning of the status 2572 that the wearable is "with Allison" might be that Allison, the subject, is assumed to be with the wearable, and proximity to the wearable may be treated as an indication of proximity to Allison.

The depicted entry 2555 includes an arrow-shaped icon 2576 that when selected, in an embodiment of the invention, causes the mobile app 140 to display a map view that indicates the location of wearable, if known, and may additionally indicate locations of one or more other devices, including e.g., other autoinjectors, wearables, and/or base stations, among other possibilities. Another icon 2580, when selected, will attempt to put into "Find My Pen" mode all stickers, associated with the subject, that receive the local signal, e.g., as described elsewhere.

In an embodiment of the invention, another type of entry (not pictured) may correspond, e.g., to home base stations that may be associated with the subject. The information that such an entry presents and/or the functions provided by this type of entry may resemble, e.g., the entry 2518 for an autoinjector and/or the entry 2555 for a wearable, possibly modified, e.g., to include information specific to a base station, such as whether the base station includes one or more useable autoinjectors.

Figure 21:
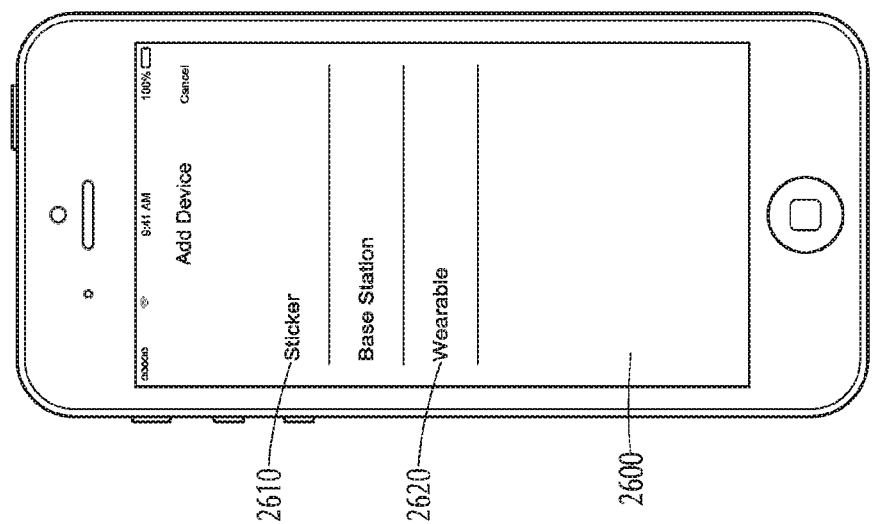

In an embodiment of the invention, the devices list screen 2500 may include an Add Device button 2590, e.g., as FIG. 20 depicts. When the user selects this button, the mobile app 140 may respond, e.g., with a new device selection screen 2600, e.g., as FIG. 21 depicts. In an embodiment, the user may select the kind of device to be added.

Figure 23:
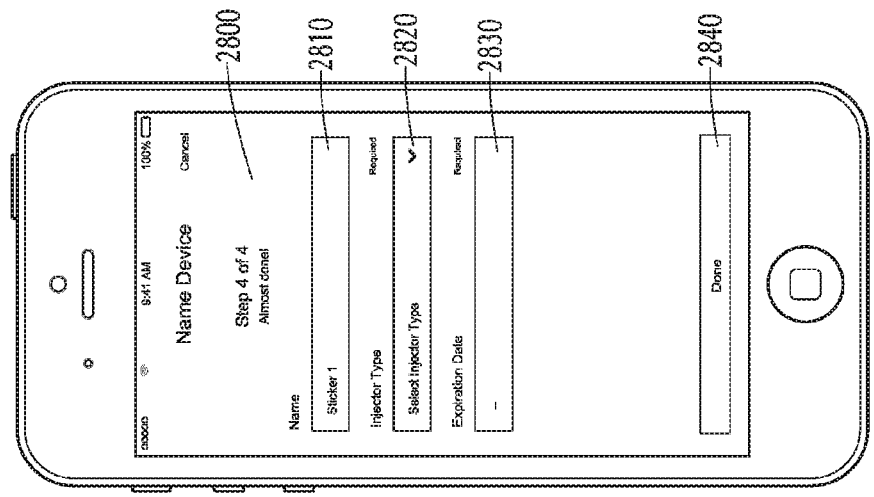
FIG. 23 depicts a flow of activating a sticker according to an embodiment of the invention.

If the user chooses to add a new sticker, e.g., by tapping "Sticker" 2610 on the new device selection screen 2600, the mobile app 140 in an embodiment of the invention may begin a flow 2700 such as FIG. 23 depicts.

The flow, according to an embodiment such as FIG. 23 depicts, may begin at block 2710, in which a user holds down the pair/cancel button on a sticker for a predetermined time, typically 3-5 seconds. After this, the sticker may enter 2720 pairing mode and may so indicate, e.g., by causing a blue LED to flash and/or by emitting one or more sounds.

The mobile app 140 may direct the user to place the sticker next to the mobile device on which the app 140 is running and may activate the sticker in block 2730. Activating the sticker 2730 may vary depending on the embodiment and the technological environment, but it may include, e.g., pairing the mobile device with the sticker, setting one or more values in persistent memory within the sticker, and/or transmitting information, e.g., associating the sticker with the subject, to support infrastructure. If activation is successful, the mobile app may indicate this fact, e.g., in block 2740.

Figure 22:
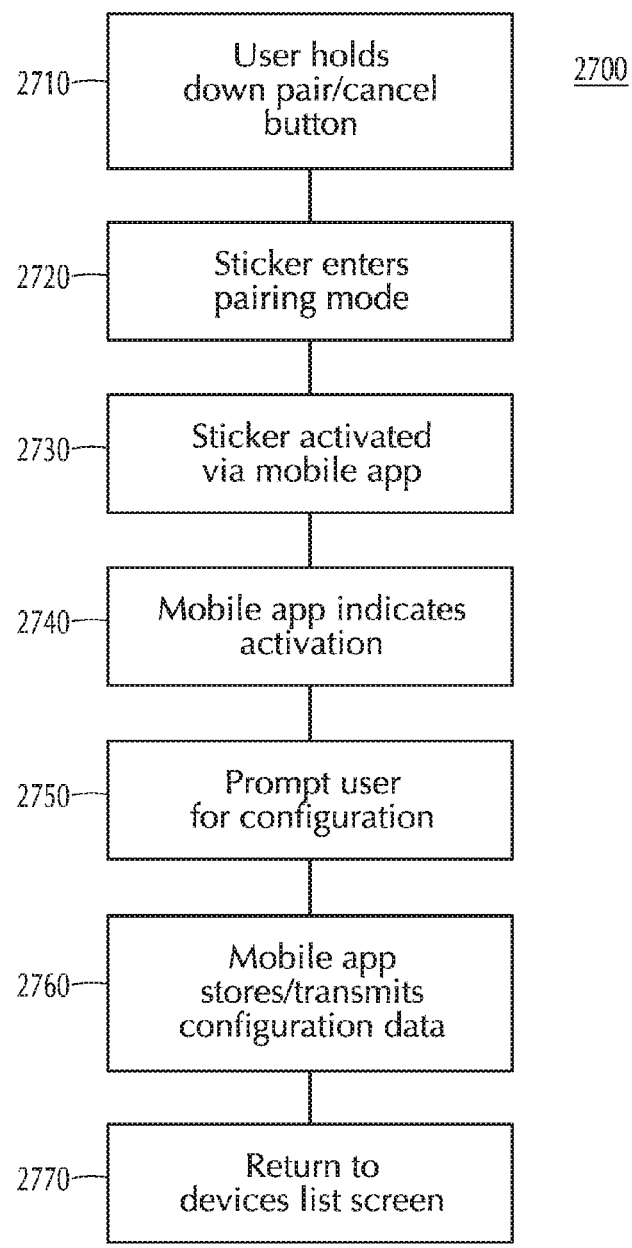
FIG. 22 depicts a user interface screen for a mobile app according to an embodiment of the invention.

Once the sticker has been activated, the mobile app 140 may prompt the user to configure the device in block 2750, e.g., by displaying a sticker configuration screen 2800 such as FIG. 22 depicts. The requested information may vary depending on the embodiment, but as FIG. 22 depicts, the user may be asked to give the sticker a name 2810, which may describe the object that the sticker is affixed to (e.g., "Allison's Home Pen"). The user may also select the type of object, e.g., from a drop-down 2820 and enter an expiration date for the medication or its container 2830. When the user is satisfied with the configuration data, the user may select the "Done" button 2840.

In response, the mobile app 140 may in block 2760 (FIG. 23) store some or all of the configuration data locally and/or send some or all of the configuration data to the support infrastructure and/or the configured sticker. In an embodiment, this configuration can also include, e.g., setting the BLE UUID, although this may in an alternative embodiment occur instead at the time of pairing, e.g., in block 2730. The mobile app 140 may then in an embodiment return to displaying, e.g., a devices list screen 2500 (FIG. 20), which may now include the newly-added sticker.

From the new device selection screen 2600 (FIG. 21), the user may in an embodiment of the invention select "Wearable" 2620. This selection may lead to a flow (not pictured) for adding a wearable, which may in embodiments of the invention resemble the flow 2700 (FIG. 23) for adding a sticker, possibly with modification reflecting differences between stickers and wearables.

Adding a wearable in this way may in embodiments cause the wearable to be considered part of the subject's network, which may in turn lead to synchronization of information, e.g., among the wearable, the smartphone, and the support infrastructure. For example, in an embodiment of the invention, data may be shared such that: 1) the wearable is made aware of what stickers it should be observing; 2) the wearable is made aware of quiet times, viz., periods in which it ought not signal a failure to detect stickers; and 3) a log of observations of stickers and loss of stickers over time is sent to the smartphone and server. In embodiments of the invention, changes to any or all of the shared data may propagate from device to device, e.g., when a smartphone or base station communicates with a wearable.

Figure 24:
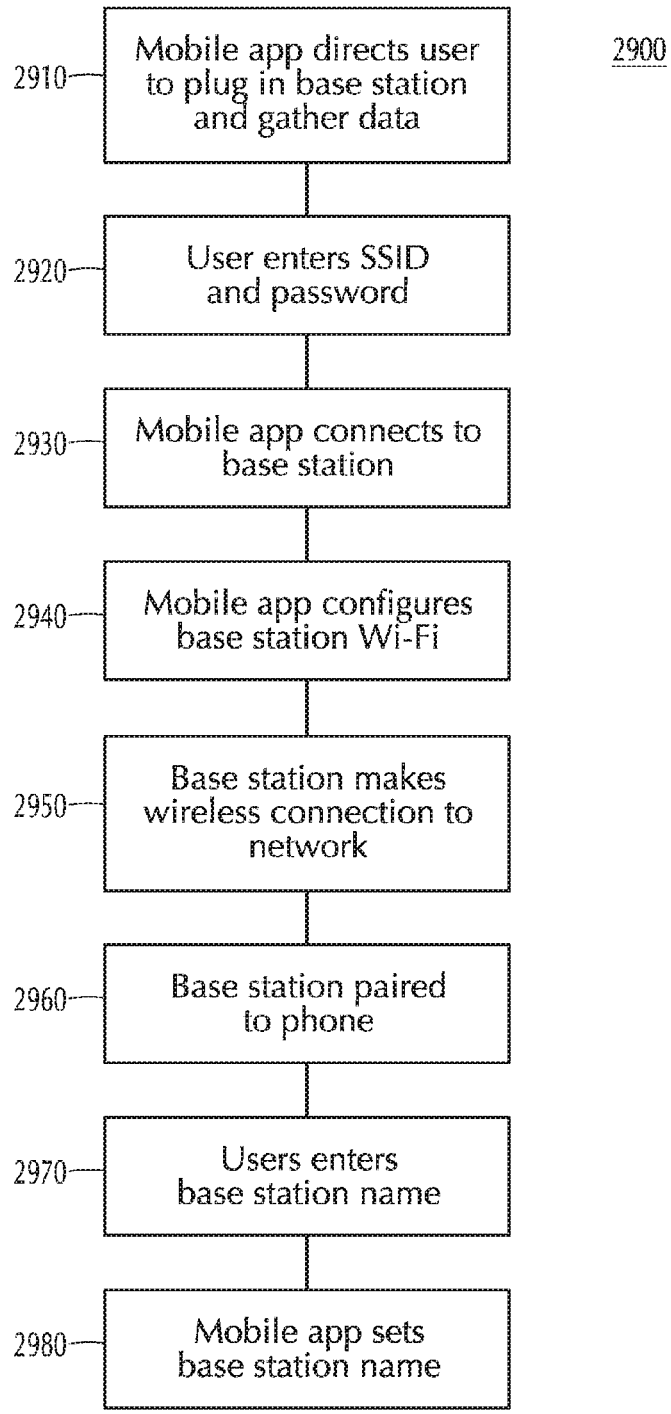
FIG. 24 depicts a flow of activating a base station according to an embodiment of the invention.

From the new device selection screen 2600 (FIG. 21), the user may in an embodiment of the invention choose to add a new home base station, e.g., by tapping "Base Station" 2630. In response, the mobile app 140 in an embodiment of the invention may begin a flow 2900 such as FIG. 24 depicts.

As depicted, the flow 2900 begins in block 2910 with the mobile app directing the user to supply power to the base station, e.g., by plugging it in, and to gather certain information that may be needed during setup, such as, e.g., the SSID and password for a Wi-Fi® network that the base station will join during setup. In block 2920, the mobile app may prompt the user for the SSID and password, which the user may then enter.

In block 2930, the mobile app connects to the base station, e.g., via an ad hoc wireless network, and then in block 2940, the mobile app transmits the SSID and wireless password to the base station. In block 2950, the base station uses this information to connect to the designated network.

According to an embodiment of the invention, once the base station has connected to the Wi-Fi® network, the base station may then be paired to the phone and/or mobile app, e.g., as block 2960 represents. The user may pair the devices, e.g., by holding down a cancel/pair button on the base station (e.g., as discussed above) for a predetermined time, e.g., 3-5 seconds. One or more LEDs within the base station may glow, e.g., blue, to indicate that the base station is in pairing mode, and then pairing may be completed, e.g., from the mobile app or a facility provided by the mobile device's operating environment.

One consequence of pairing the mobile app with the base station, according to an embodiment of the invention, may be to associate the base station with the subject, and information indicating this association may be sent to the support infrastructure, e.g., at the time of pairing or, later, when other information about the base station's configuration is sent to the support infrastructure.

Once the mobile app has been paired with the base station, the user may then in an embodiment further configure the base station. For example, the mobile app may prompt the user for a name for the base station. In an embodiment of the invention, the user may be prompted for information that specifies the location of the base station, e.g., when the location is not determined via GPS, IP-based geolocation, or other automatic means. Block 2970 represents the user's entry of this information.

In block 2980, the mobile app transmits the configuration information to the base station with which it has just been paired. The base station may store this information, e.g., in persistent memory. Further, in an embodiment of the invention, information identifying the base station and describing its configuration may be sent, e.g., to the support infrastructure for future reference.

In certain embodiments, a smart base station device 50 may connect with a cloud server to obtain identification of all the devices registered within a medication system management system, e.g., as here described. Upon receipt of the identification of the registered devices, smart base station device 50 may establish a connection with those devices once they are present within a region of detection.

As FIG. 20 depicts, a devices list screen 2500 may in an embodiment of the invention include a button or other control 2595, e.g., labeled "Manage Devices". Selecting this button may, e.g., cause display of one or more controls (not pictured) allowing the user to remove one or more devices, e.g., individually, and/or change configuration information for any one or more devices.

Returning to FIG. 15, the navigation menu 2000 may include an item 2024 labeled, e.g., "Allergy 101". Selection of this item may in an embodiment of the invention cause the mobile app to present educational information (not pictured) related, e.g., to severe food allergies. The educational information may cover any one or more of a wide variety of topics, including (among many possibilities) food allergies generally, the particular food allergies that affect the subject, techniques for avoiding allergens, ways to detect anaphylaxis, and how to respond to anaphylaxis if it should be suspected or actually in progress. The educational information may be in any one or more of multiple forms, which may include, e.g., text, still and moving pictures, and audio. Educational information may be stored locally, e.g., within the mobile app, and/or accessed remotely, e.g., via the Internet and accessed via one or more hyperlinks presented by the mobile app.

The navigation menu 2000 in an embodiment of the invention may include an item 2028 allowing the user to see any notifications provided by the system. The presentation of the notifications may vary, e.g., with the operating environment and/or the embodiment of the invention, but may take the form, e.g., of a list (not pictured) of entries, one for each notification. The user may in such an embodiment select a notification's entry, and the mobile app may respond, e.g., with the details of the notification (not pictured).

In embodiments of the invention, support infrastructure may exist that supports and coordinates the functioning of other components, both individually and in combination with each other. In an embodiment, the support infrastructure may be one or more computer servers, and the support infrastructure may thus be referred to as the "server".

For example, in an embodiment of the invention, a server acting as the support infrastructure may be a computer system including, e.g., one or more computers operating the Ubuntu® platform based on the Linux® operating system. A Ubuntu® host server may comprise, e.g., an Nginx® server and rails server application. A Ubuntu® host server may further comprise a PostgresDB that acts as the data tier for the from rails server application. A rails server application may further communicate, e.g., with an Amazon® Simple Notification Service (SNS) server and/or a Twilio® call gateway. The Amazon® SNS server may in turn communicate with Apple® Push Notification Service (APNS), which may provide push notifications to a mobile device. The Twilio® call gateway may provide voice or short messaging service (SMS) transmission a mobile device.

In some embodiments, the sticker 120, wearable 130, and home base station 150 may provide BLE transmission to a mobile app 140 on a mobile device. In further embodiments, a mobile device may provide cellular or other data transmission to the server via a REST application programming interface (API). Similarly, in an embodiment, home base station 150 may use Wi-Fi® to connect to the Internet and interact with the server via a REST API. In some embodiments, the REST API serves as a front end on the server, through which other devices and applications communicate with the rails server application.

In embodiments of the invention, the support infrastructure may receive and correlate information from many devices, e.g., as disclosed above, to determine whether a subject has sufficient access to an autoinjector and to generate alerts if a subject appears not to have such access. Individual devices may similarly generate and/or transmit alerts, e.g., if they cannot receive a signal from an appropriate device.

It will be appreciated that the architecture of a support infrastructure described above is only one possible implementation. According to embodiments of the invention, other architectures are possible, including, e.g., architectures within which multiple machines perform tasks described as being performed by a single machine and/or vice versa. It will further be appreciated that such a support infrastructure may be implemented on a cloud-based computer platform, e.g., as may be known in the art and commercially available.

In embodiments of the invention, a support infrastructure may record data including configuration data, profiles, history, and any other information related to the operating of the system that it may be thought desirable to store. It will be appreciated, however, that this may, in embodiments of the invention, allow any device or devices to be replaced as necessary, with any relevant information being restored to the replacement device, e.g., from the support infrastructure.

In an embodiment, alert (or, equivalently in this context, notification) technology may use a passive system to look for devices; the system is "passive" in the sense that an observer—e.g., a smartphone or wearable—wakes from a lower power state as a result of a trigger event and tries as a result to observe nearby stickers. Table 2 describes possible trigger events in an exemplary embodiment of the invention.

TABLE 2

Notification Trigger Events

| Trigger Event | Description |
| --- | --- |
| Initial state | An observer will scan for devices when it is activated. |
| Significant location change | The observer's location (e.g., latitude and longitude) has changed to an extent that causes the observer to be notified of the change. For example, an app on an iOS ™ device may request that the operating environment notify the app when a system-defined (defined by the system, not the app) has been detected. |
| Enter region | The observer has entered iBeacon™ range of a sticker or wearable. |
| Exit region | The observer is no longer within iBeacon™ range of a sticker or wearable. |

In an embodiment of the invention, each trigger event results in a scan. After an observer scans for a sticker, in an embodiment, the observer may automatically send a report of the scan and its results to the support infrastructure, e.g., immediately or when the opportunity arises, as described further in connection with logging.

The report may result in an immediate update to the state of the system. Table 3 lists states according to an exemplary embodiment of the invention.

TABLE 3

System States

| State | Meaning |
| --- | --- |
| Subject is not with sticker | The subject's smartphone, as an observer, did not detect a signal from the subject's sticker. |
| Subject is with wearable but not sticker | The subject's smartphone, as an observer, detected a signal from the subject's wearable but did not detect a signal from the subject's sticker. |
| Subject is with sticker | The subject's smartphone, as an observer, detected a signal from the subject's sticker. |
| Wearable is with sticker | The subject's smartphone, as an observer, detected a signal from the subject's wearable and the subject's sticker. |

It will be appreciated that wireless networking technology may make connections that, e.g., may frequently be broken and then reconnected. Simply generating an alert every time a connection experiences a break may result in many false alerts, which may be inconvenient and annoying. Other possible shortcomings of a naïve scheme for notification may include, e.g., generating multiple alerts when a subject repeatedly in a short time leaves and enters a device's iBeacon™ region, or when after an Exit region event, a device can still be detected by a scan even though it remains outside the iBeacon™ region.

Thus, it may be desirable in an embodiment of the invention to reduce the sensitivity of (or "dampen") some or all alerting mechanisms to reduce false or otherwise unnecessary alerts. According to embodiments of the inventions, one or more algorithmic forms of alert dampening may be provided, which may rely, e.g., on one or more heuristics. For example, in an embodiment of the invention, four distinct types of dampening may apply: system dampening, wearable and base station dampening, safe zone dampening, and quiet time dampening.

System dampening may refer, e.g., to dampening applied by the support infrastructure. In an exemplary embodiment of the invention, all trigger events cause the triggered device to scan. (For this purpose, in this embodiment, a "scan" may mean that a device, such as a smartphone or wearable, acts in a Bluetooth® master mode, looking for devices such as stickers.) In such an embodiment, the system state, maintained, e.g., by the support infrastructure, may be updated immediately to reflect the result of the scan. But the system may then wait for a timeout period (typically 1-5 minutes, depending, e.g., on the embodiment and possibly the type of change to the system state) before broadcasting a notification from the support infrastructure (a "system notification"). In an embodiment of the invention, this timeout may be set to 5 minutes, but, in other embodiments, any value may be used, including, e.g., 30 seconds, 1 minute, 2 minutes, 3 minutes, 4 minutes, 6 minutes, or any other value that is determined to be suitable.

It will be appreciated that using the support infrastructure to measure timeout periods in an embodiment of the invention may reduce the amount of time that battery-powered devices spend in an active mode, which may reduce the drains on their batteries. It will further be appreciated that the devices making up the support infrastructure may draw power, e.g., from AC mains, which would mean that battery drain may not be a consideration for those devices.

Wearable and base station dampening may apply, e.g., to local notifications generated from these devices. Wearables and/or base stations may in an embodiment of the invention use—and possibly remain in—a higher power mode in which they often (or effectively continuously) scan for stickers (and wearables in the case of the base station) in their immediate area. But such a configuration may generate "noise", though, such as may result, e.g., when a sticker is observed, then not observed, then observed again in short order. This may happen when the observer does not reliably receive the sticker's signal because of, e.g., RF noise, distance, or a weak signal or battery.

In embodiments of the invention, wearables may issue a local notification when no sticker is detected, but they, too, may apply a timeout before doing so. In an embodiment of the invention, this timeout may be set to 3 minutes, but, in other embodiments, any value may be used, including, e.g., 30 seconds, 1 minute, 2 minutes, 3 minutes, 4 minutes, 6 minutes, or any other value that is determined to be suitable.

In embodiments of the invention, a base station may similarly issue local notifications and similarly apply a timeout before doing so.

Alternatively, in embodiments of the invention, a base station may merely report the observation of stickers and wearables nearby. In such an embodiment, the base station may maintain an simple inventory of detected devices and immediately report any change to that inventory to the support infrastructure. In such an embodiment, the support infrastructure may immediately change the system state, and system notification (with system dampening) may be used.

Safe zone dampening, in embodiments of the invention, refers to definition of, e.g., geographic safe zones. If a subject is deemed to be in a safe zone, the system state may be updated continuously, e.g., as above, but some or all notifications may be suppressed.

Safe zone dampening according to an embodiment may apply, e.g., in locations such as a home, office, or school, in which an observer and stickers may enter and/or exit frequently, due to the movement of these devices in relatively close proximity to a device but nonetheless far enough away to cause frequent scanning from Enter region and Exit region signals.

In such an embodiment, all events sent to the support infrastructure, including, e.g., observation events of stickers or an observer no longer seeing a sticker, may cause an immediate system state update. All event notifications may also have location information appended, e.g., in the form of latitude/longitude or otherwise. Where an event is generated by a device with GPS capabilities, the location information may be provided, e.g., by that device; otherwise, the location may be retrieved, e.g., from a database after having previously been determined, or may be determined, e.g., from IP-based geolocation or otherwise. If an event such as an observer's not finding a sticker occurs in a safe zone, in an embodiment of the invention, the system notification may be suppressed.

It will be appreciated, however, that information about the subject's location may not always be complete. For example, a child may carry only a wearable and an autoinjector with an attached sticker, neither of which may in an embodiment include GPS or non-local communication capability. Moreover, the relevance of a safe zone is that, in an embodiment, it may represent a region in which the child is considered safe, so that the system need not rely on reports, e.g., by a base station, that the wearable and a sticker have been observed together; by hypothesis, this may mean that no base station or other device is placed to transmit location information related to the subject.

One way to address such circumstances, according to an embodiment of the invention, may be to consider the last known location of the wearable as its location for this purpose. For example, after a child is dropped off at school, the location may be considered to be the school, based, e.g., on location information provided by a smartphone belonging to the subject's parent or by a base station or other device at the school. The system may consider this to be the subject's location until it receives location information to the contrary, e.g., from a smartphone or base station detecting the wearable at another location. Then, if the school has been designated a safe zone, the system may suppress notifications based, e.g., on a failure to detect the wearable and a sticker together.

In an embodiment of the invention, the system may not suppress all alerts merely because the subject is deemed to be in a safe zone. For example, if required, the student may in an embodiment be alerted on a wearable if no sticker is nearby, even in a safe zone.

Safe zones may be designated, e.g., using an appropriate interface (not pictured) on a mobile app and/or web application. For example, a safe zone may be defined on a map view in terms of a marker (e.g., a "pin") and a radius around that pin. The radius may in embodiments of the invention be any value considered to be appropriate, which may typically be in a range of 50-500 meters, and, in an embodiment, the radius may be specified by the user when the safe zone is define and may subsequently be modified. In addition to or instead of the foregoing, it may be possible in an embodiment to define a safe zone in terms of one or more devices, e.g., base stations.

Quiet time dampening may in an embodiment of the invention involve setup by a user of one or more time periods when system notifications may be suppressed. For example, a user may define weekdays between 8 A.M. and 3 P.M as quiet times on the assumption that a child subject will be in school during those hours and therefore supervised by caregivers, including, e.g., a school nurse. Or a user may define 10 P.M. to 6 A.M. every day as a quiet time, assuming the subject to be home in bed between those hours.

As discussed elsewhere, it may in an embodiment be possible to define a team of persons to receive notifications under various circumstances Quiet times may in an embodiment be defined with regard to particular team members.

In embodiments of the invention, one or more protocols that may be useful to implementing one or more devices and/or systems may not precisely support an application such as an embodiment of the invention may include. For example, iBeacon™ and/or software associated with it may not supply convenient access to an iBeacon™ major and minor ID. For another example, interference and/or fluctuations in system processes may mean generation of spurious Enter region and Exit region events in the absence of any significant movement of any device.

In an embodiment of the invention, trigger events may be based, e.g., on a combination of iBeacon™, to determine a possible trigger of activity, then an actual scan by a BLE central device to determine exact devices in the proximity of the smartphone. The combination of the two approaches may realize much of the power saving attributable to BLE while making trigger events more reliably dependent on external circumstances.

In embodiments of the invention, it may be possible to configure some or any devices such that any events, or any desired subset of them, may be logged, e.g., by a support infrastructure. "Events" for this purpose can be considered broadly to include any detectable change of state of any device, although it more commonly may include only such changes as, e.g., acquisition of one device's signal by another, loss of such a signal, activation and/or cancellation of an emergency, addition and/or removal of any one or more devices, activation of "Find My Pen" status, configuration changes, powering devices off or on, and/or other changes of comparable import and/or diagnostic usefulness.

In embodiments of the invention, devices that may not enjoy continuous contact with a support infrastructure may store log data locally until an opportunity arises to transmit it, e.g., to a support infrastructure. For example, a wearable may maintain a record of events that involve it; when a communication channel becomes available, e.g., via a smartphone, the wearable may then transmit to a support infrastructure events that have been recorded since the last transmission opportunity. It will be appreciated that the transmission may be direct, in the sense that the smartphone may act essentially as a router enabling a connection between the wearable and the support infrastructure, or indirect, in the sense that the wearable may dump a record of events to the smartphone, which may store them and then separately transmit events from one or more devices to the support infrastructure. It will further be appreciated that a device such as a smartphone may maintain its own log of events and may, even when functioning essentially as a router, as above, make its own copies of the events that are passing through it on their way to being recorded by the support infrastructure.

It will be appreciated, however, that the result may be generation and storage of a great deal of data about the devices and/or the actions of those who carry and/or use them. In embodiments of the invention, one or more tools may exist, e.g., to analyze and/or present logged data. For example, within the system: 1) family and parents may be given a general graph of adherence during the day, possibly highlighting opportunities to improve adherence; 2) adherence may be scored over a general population to determine risk factors of a specific child, especially in accordance with other medical information; general times of data and patterns of adherence may be scored; and 3) identification, e.g., via application of machine learning techniques, of events and/or cycles (e.g., weekends vs. weekdays) that may cause or exhibit varying patterns of adherence, possibly with an eye to adjustment of notification goals.

As discussed previously, devices such as stickers, wearables, and base stations may in embodiments have an emergency mode (which may also be referred to as an emergency state). In this state, the device may act, e.g., to attract attention, possibly alerting others who may help the subject. For example, a device may, e.g., flash lights in one or more colors and/or make one or more sounds such as buzzing or tones.

In an embodiment, some or all devices may be configured to playback, e.g., voice instructions for how to handle the emergency. Further, in an embodiment, the instructions may prompt the user to provide input, e.g., through one or more of a device's buttons, to control the flow of the instructions. In an embodiment, instructions may be available in multiple languages; a default language may be chosen, e.g., when the device is activated, but a user may be able to change the language in response to one or more prompts.

A device in emergency mode may also broadcast its status locally, e.g., using BLE. In an embodiment, one or more devices that detect another device signaling an emergency state may themselves enter emergency mode. Alternatively, in an embodiment, a sticker detecting a nearby device in emergency mode may enter, e.g., "Find My Pen" mode, to make the pen (or other object) easier to find. Similarly, when a device receives input (e.g., from one of its buttons) to cancel an alert, in an embodiment of the invention, the device may broadcast this change of state locally, and other devices that detect this change of state may respond by leaving emergency mode.

An emergency may also be activated, e.g., from a mobile app on a smartphone. For example, FIG. 12 depicts a screen 1700 that includes a slide control 1734, which may be used to enter emergency state. It will be appreciated that that a mobile app may provide one or more other ways to signal an emergency in addition to or instead of the slide control 1734.

When a mobile app enters emergency state, it may broadcast this change of state locally, e.g., with BLE. Other devices nearby, detecting this change of state, may respond, e.g., as described above, entering emergency mode and/or "Find My Pen" mode.

Figure 25:
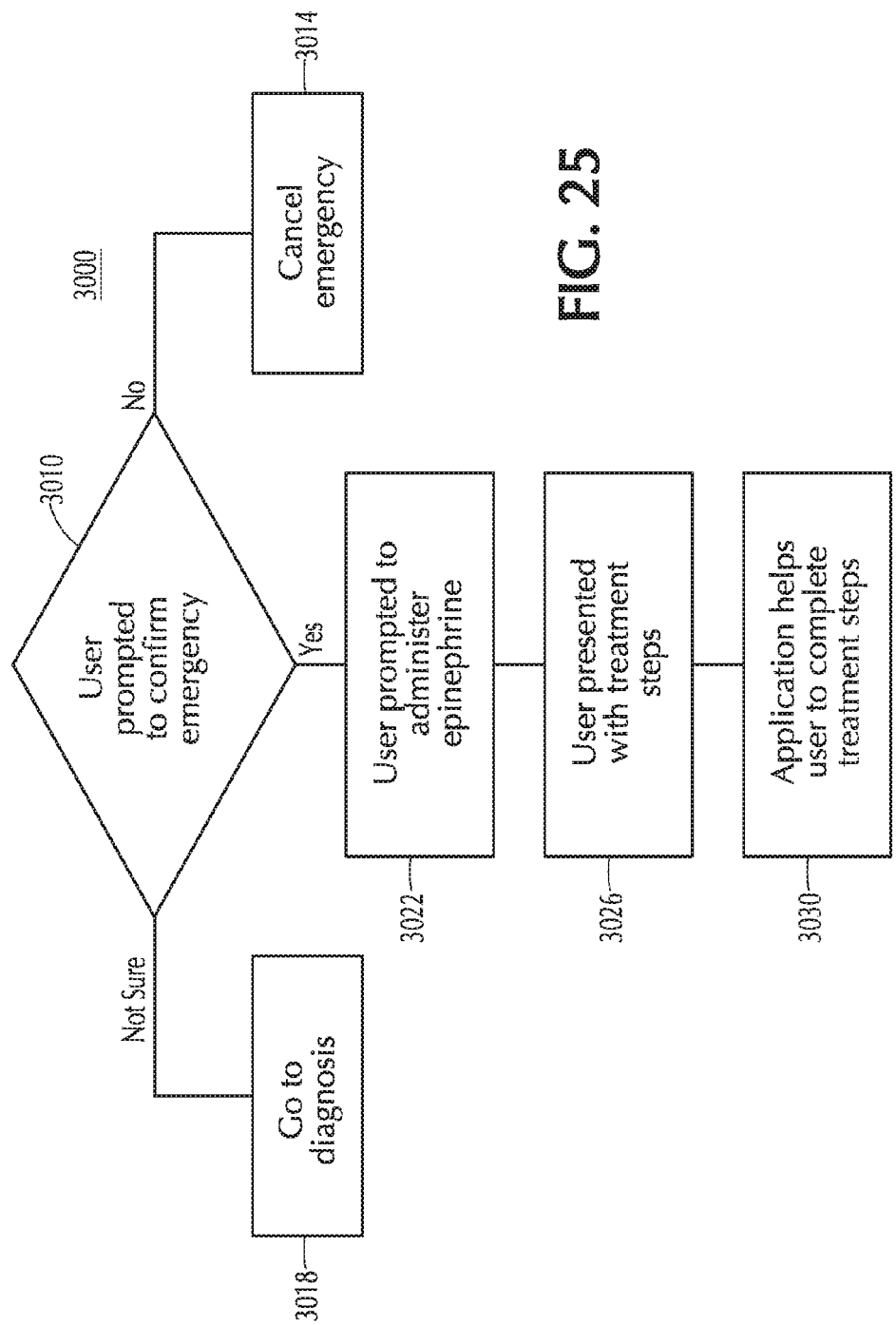
FIG. 25 depicts a flow of activating an emergency on a mobile app according to an embodiment of the invention.

In an embodiment, the mobile app, on entering emergency mode, may walk the user (who may not be the subject, but, e.g., a member of the subject's team) through responding to the emergency, e.g., by taking the user through a flow such as FIG. 25 depicts.

As depicted, the flow 3000 may begin at block 3010, with the mobile app prompting the user to confirm activation of the emergency. In an embodiment, the user may have three options. First, the user may cancel the emergency (block 3014). Second, the user may not be sure that an emergency applies, and the app may proceed to block 3018 to help the user determine whether anaphylaxis may be occurring.

Third, the user may confirm that, yes, the subject appears to be having an allergic reaction. In response, the mobile app in an embodiment may, e.g., prompt the user in block 3022 to administer epinephrine using an autoinjector. The prompt screen (not pictured) may ask the user to indicate whether the epinephrine has been administered, and the user may answer yes, once it has in fact been administered, or may indicate that the user cannot administer it, possibly because no autoinjector is available.

In either case, the mobile app may then, in an embodiment, present the user with further actions to be taken in treatment of the episode (block 3026) and provide various facilities to help the user with those actions (block 3030).

Figure 26:
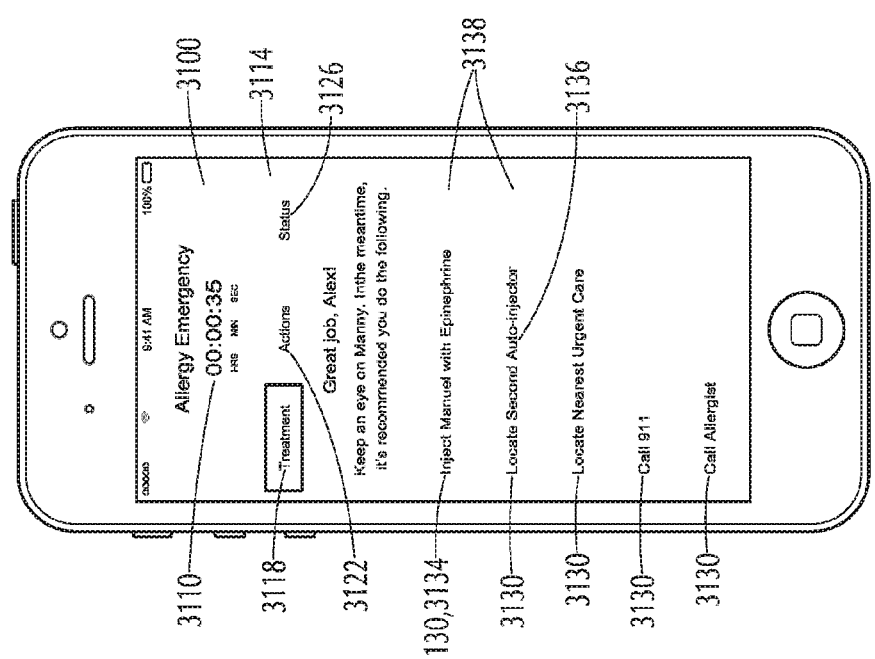

FIG. 26 depicts a treatment steps screen 3100 such as may be presented in block 3026 (FIG. 25) according to embodiments of the invention. The depicted screen 3100 includes a timer 3110 that indicates the elapsed time since the emergency was activated; in embodiments, the timer 3110 may be present on all screens presented by a mobile app during an emergency.

The treatment steps screen 3100 may also include, e.g., a tab bar or button bar 3114, which may enable the user to switch between screens and/or views during the emergency. The depicted bar 3114 shows three options: "Treatment" 3118, "Actions" 3122, and "Status" 3126. As depicted, the "Treatment" 3118 option is highlighted, indicated that the treatment steps screen 3100 is current selected and displayed.

The treatment steps screen 3100 displays a list of steps 3130 that may be advised in responding to an allergic emergency. As depicted, the first step 3134, injecting the subject with epinephrine, has been taken, but the others have not. Each step 3130 includes a textual description 3136 of the action to be taken, and a checkbox 3138 indicating whether taking that action has been recorded. Because FIG. 26 depicts a treatment steps screen 3100 immediately after administration of epinephrine, the checkbox 3138 in this step 3134 is checked, but the others are not.

It will be appreciated that the displayed steps are part of an exemplary treatment protocol selected in connection with an embodiment of the invention, and that other treatment protocols are possible in connection with embodiments of the invention. It will also be appreciated that one or more other steps may be presented in addition to, or instead of, some or all of the steps 3130 that FIG. 26 depicts if the user indicates, e.g., in block 3022 (FIG. 25), that epinephrine has not been administered; for example, the mobile app may instruct the user, e.g., to stay with the subject and call 911 immediately.

Figure 27:
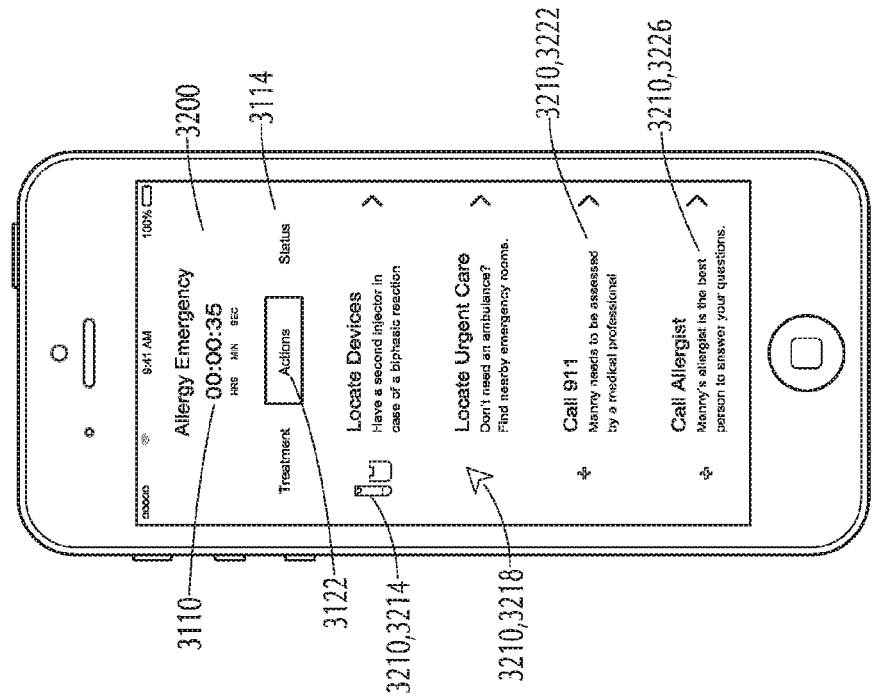
FIGS. 26-29 depict user interface screens for a mobile app according to an embodiment of the invention.

FIG. 27 depicts a treatment actions screen 3200 such as may be displayed, e.g., during step 3030 (FIG. 15), in an embodiment of the invention. As depicted, the "Actions" 3122 item is highlighted to indicate selection of this screen. The treatment actions screen 3200, as depicted, includes a list of actions 3210 that the user may select.

In an embodiment of the invention, if the user selects the "Locate Devices" action 3214, the mobile app may display, e.g., a map (not pictured) of the area near the user, and the map may indicate autoinjectors (with stickers) that are near the user, or, alternatively, near the subject. The display may include, e.g., stickers that are associated with the subject, home base stations that are associated with subject and/or currently hold an autoinjector that is associated with the subject, and/or public base stations that contain useable autoinjectors. In an embodiment, any nearby stickers that are not yet in "Find My Pen" mode may receive a command to enter that mode.

In an embodiment of the invention, a subject may be able to indicate a willingness to allow others to use one of that subject's autoinjectors in an emergency. In that case, a user, associated with a second subject, who selects the "Locate Devices" action 3214 may also see on the map the location of the first subject and/or one or more home base stations associated with the first subject.

Similarly, in an embodiment of the invention, a user selecting the "Locate Urgent Care" action 3218 may be presented, e.g., with a map (not pictured) showing one or more urgent care centers near the user and/or subject. The display with the map may further include information about one or more of the indicated urgent care centers.

The action taken in response to selection of the "Call 911" action 3222 may be expected to vary depending on the embodiment of the invention. For example, in an embodiment, it may cause the smartphone to make an emergency call. Alternatively, in an embodiment, it may connect the user with an operator in a dispatch center, who may summon emergency aid on behalf of the subject; this connection may, in embodiments of the invention, use voice and/or text messaging.

In an embodiment of the invention, the effect of choosing the "Call 911" action 3222 may be to automatically (i.e., without further human intervention) cause a message to be sent to emergency services to summon help to a subject. But it will be appreciated that applicable law and/or regulations may limit the use of such embodiments.

In an embodiment of the invention, the effect of the "Call Allergist" action 3226 may be to cause the device to attempt to contact the subject's allergist, e.g., by having the smartphone call a stored phone number that is associated with the allergist.

Figure 28:
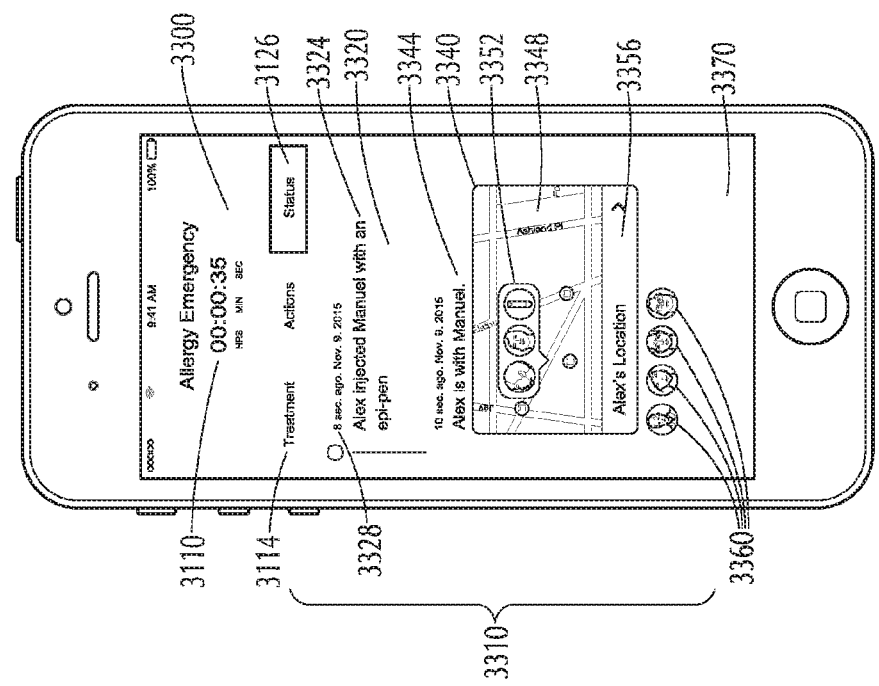

FIG. 28 depicts an emergency status screen 3300, e.g., as a mobile app may present to a user in an embodiment of the invention. The emergency status screen may present, e.g., a scrollable timeline 3310 of events since the emergency was activated. As depicted, one displayed event 3320 includes a text message 3324 that indicates that the subject was injected with epinephrine. This event includes a time/date stamp 3328; in embodiments of the invention, any or all events in the timeline 3310 may be displayed, e.g., with a similar time/date stamp.

In an embodiment of the invention, an event such as this 3320 may be generated automatically, e.g., in response to a user's indication that an injection has been administered to the subject. In embodiments of the invention, similar events may be automatically registered and broadcast, e.g., upon a user's taking any or all actions such as may be made available via a screen 3200 such as FIG. 27 depicts.

Returning to FIG. 28, the timeline 3310 includes an event 3340 indicating that a team member has been detected near the subject. The event 3340 includes a textual description 3344 of the event and a map 3348 that indicates the location of the team member. That location, in an embodiment such as FIG. 28 depicts, may be indicated, e.g., by an indicator that conveys additional information. For example, the indicator 3352 in FIG. 28 includes icons that mean that the subject, an identified team member, and an autoinjector are all at the indicated location. A location-related event 3340, e.g., as depicted, may include one or more elements—such as a drop-down list 3356 and/or a collection 3360 of user pictures—that may allow a user to see the location of any one or more members of the subject's team.

As depicted, the emergency status screen may include a text entry area 3370, which may in an embodiment allow a user to send other status updates, e.g., as the user might compose and send a text message.

Any or all actions and/or events that take place during an emergency, including (but not limited to) the actions and events described above, may be sent to support infrastructure and logged, e.g., as described elsewhere. Some or all of the logged information may be passed along to team members, e.g., as alerts, particularly the beginning and end of emergency status. Status updates from one team member may be available to other team members, e.g., through their own smartphones.

Figure 29:
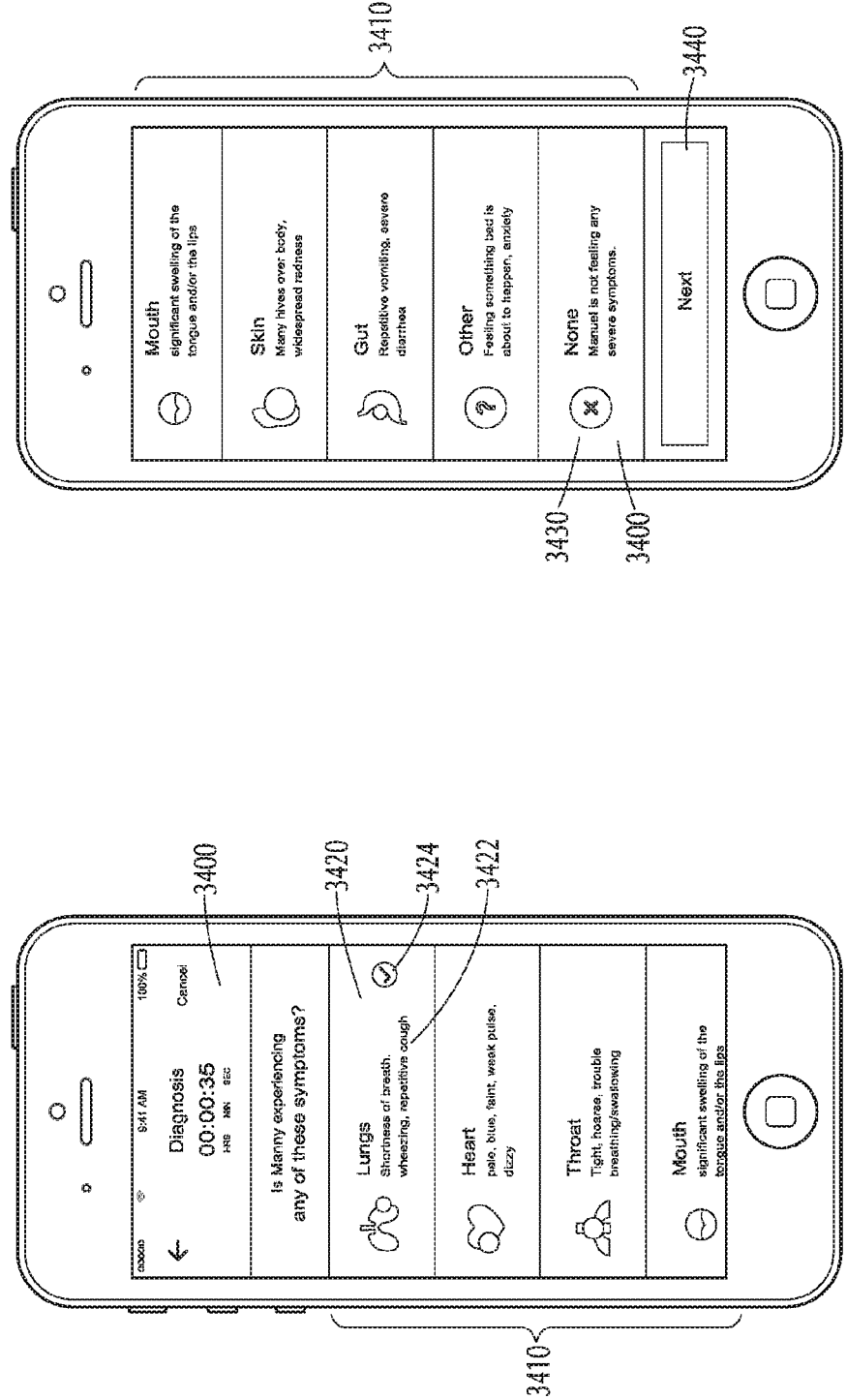

Returning to FIG. 25, a user who is not sure that an allergic reaction is taking place may in embodiments of the invention be guided through diagnosing the possible reaction. FIG. 29 depicts a scrollable screen 3400 according to an embodiment of the invention that includes a list 3410 of potential symptoms 3420 of anaphylaxis. Each potential symptom 3420 includes a description 3422 and a checkbox 3424. As depicted, the list 3410 also includes an item 3430 allowing the user to indicate that the subject is not experiencing any of the listed severe symptoms.

At the bottom of the screen 3400, in an embodiment such as FIG. 29 depicts, is a button 3440 labeled "Next" that may, e.g., submit the form for evaluation. The button 3440 may be disabled until any one or more entries in the list 3410 are selected.

In response to selection of the "Next" button 3440, the mobile app (or, alternatively, the support infrastructure) may evaluate the submission to determine whether the subject may be experiencing anaphylaxis. In an embodiment of the invention, the subject may be deemed to be in potential anaphylaxis if any of the symptoms (other than "None") has been selected. Alternatively, it will be appreciated by those skilled in the medical arts that some listed symptoms may be generally considered strong indicators of potential anaphylaxis and others may be generally considered to be weak indicators of it. Thus, in an embodiment, a subject may be deemed to be in anaphylaxis if any two weak indicators have been selected and/or if any one strong indicator has been selected.

In either case, if the user is deemed as a result of this inventory of symptoms to be in anaphylaxis, the mobile app in an embodiment of the invention may, e.g., proceed directly to block 3022 in FIG. 25, activating an emergency and directing the user to inject the subject with epinephrine.

In an embodiment, one or more sensors may be provided that may be capable of automatically detecting one or more symptoms, e.g., of anaphylaxis. Such sensors may be, e.g., included in a wearable device, separate devices that may interact with a smartphone or other device via a wired and/or wireless connection, and/or be common parts of smartphones or other electronic devices (e.g., a smartphone microphone and/or camera). In such an embodiment, e.g., a mobile app and/or support infrastructure may algorithmically analyze one or more inputs from one or more such sensors, determine that the input reflects one or more biological indicators of anaphylaxis, and report potential anaphylaxis based on one or more indicators that may include, without limitation, cardiac output, heart rate, blood pressure, blood oxygen saturation, respiration rate, sound, flushing on the skin, hives on the skin, skin temperature, and perspiration. In some embodiments, anaphylaxis detection wearable device 60 may comprise one or more sensors including, but not limited to, electrocardiogram (EKG) sensors, electroencephalogram (EEG) sensors, pulse oximetry sensors, photoplethysmography sensors, skin color sensors, and bioimpedance sensors.

For example, it is known to use a smartphone camera to obtain photoplethysmograms, breathing rate, and blood oxygen saturation, among other physical parameters. In an embodiment, anaphylaxis may be detected by an increase in heart rate, an initial increase in blood pressure followed by a rapid decrease, an oxygen saturation of less than 99%, an increase in breathing rate, a decrease in skin temperature, and an increase in perspiration. In some embodiments, anaphylaxis may further be identified by a decrease in cardiac output.

In some embodiments, an anaphylaxis detection wearable device may be in the form of a wearable chest patch or a necklace. In these embodiments, the anaphylaxis detection wearable device may comprise a stethoscope feature to monitor wheezing and stridor to detect an early onset of an anaphylactic reaction. The stethoscope feature may comprise a microphone with a sensitivity of at least. In an embodiment, acoustic signal may be collected and be processed by noise cancelling and filtering algorithms. Various features such as frequency and amplitude may be extracted from the processed acoustic signals. Based on the signature of the sound, anaphylaxis may be identified. In certain embodiments, the anaphylaxis detectable wearable device may further comprise an accelerometer to detect motion of the subject and eliminate false positives.

In an embodiment, an anaphylaxis detection wearable device may comprise skin sensors and bioimpedance sensors to monitor flushing, perspiration, and hives on the skin. The skin sensors may comprise a camera and a memory comprising color recognition algorithms. The bioimpedance sensors may be configured to detect electrodermal activity.

In certain embodiments, an anaphylaxis detection algorithm is provided. A probability scaling from 0% to 100% may be calculated based on a combination of a subject's history of asthma and prior anaphylactic reactions, in addition to the frequency of stridor, the extent of peripheral vasoconstriction, a slight decrease in skin temperature, a decrease in blood pressure, and a decrease in cardiac output.

It will be appreciated that managing a potentially life-threatening condition such as severe food allergies may be best done by a team, which may include a subject's family. This may be particularly true when the subject is a minor child. Thus, systems and methods according to embodiments of the invention may involve a defined group of people other than the subject, and these people, together with the subject, may constitute the subject's team.

More precisely, a subject's team in connection with an embodiment of the invention may be those people who have smartphones or other devices with a mobile app installed and who have registered, e.g., with support infrastructure, as members of a subject's team. Members of a team may have different roles and/or levels of access to shared data, and these roles and/or levels may be managed, e.g., by a team member with administrative privileges, through a suitable user interface (not pictured).

For example, in an embodiment, a subject may have full access to all the data in the mobile app through cloud servers. Progressively narrower levels of access may be granted, e.g., to immediate family, friends, level 1 caregivers, level 2 caregivers, and other team members. Immediate family may include a child, parents, and siblings of a subject, although, in an embodiment of the invention, the parents of a subject who is a minor child may have access that is identical to that of the subject. Friends may include invited friends of a subject. Level 1 caregivers may include, e.g., a school nurse, a babysitter, a teacher, a coach, a camp counsellor, grandparents, a parent of a friend, a doctor, or an allergist. Level 2 caregivers may include, e.g., a new baby sitter, a new teacher, a parent of a playmate, or a parent of a friend whom the subject is having, e.g., a sleep-over party with. Other team members may include a friend of a friend, a cook at the school of subject, a waiter at a restaurant, or an emergency responder.

Team members may receive notifications of events, e.g., as described. Notifications may be filtered based, e.g., on team members' respective levels, the type of notification, and/or other factors that may be configured, e.g., through an appropriate user interface (not pictured) of the mobile app and/or a web site.

In some embodiments, the software components in the system may be capable of determining statuses and intelligently routing notifications in accordance with the present disclosure based on the presence of a subject, a medical device, a caregiver, a preset time schedule, or a combination of the above. In certain embodiments, the software components may be capable of managing notifications based on a combination of a time-based schedule and a physical location of a medical device. In some embodiments, the software components may be capable to determine which connected devices need to receive a notification. In another embodiment, application stored on a smart mobile device may share with a caregiver a link to a secure website via SMS or email. In accordance with the examples of this disclosure, the system may monitor the presence or location of a device in combination with the presence or location of a subject or a caregiver. In some embodiments, the software components may be configured to customize an allergy action plan based on the subject and the team members' preferences.

This disclosure refers to particular embodiments and examples, but it will be understood by those skilled in the art that various changes may be made and equivalents may be substituted for elements thereof without departing from the scope of the present disclosure. In addition, many modifications may be made to adapt a particular situation or material to the teachings of the present disclosure without departing from the scope of the present disclosure.

Therefore, it is intended that the present disclosure not be limited to the particular embodiments disclosed as the best mode contemplated for carrying out the present disclosure, but that the present disclosure will include all embodiments falling within the scope and spirit of the appended claims.

EXAMPLES

Embodiments of the invention may include, e.g., components and/or activities such as described above. The following examples further describe embodiments of the invention and/or their components and/or uses.

Example I

The use of a system comprising a sticker attached to an epinephrine pen and a smartphone by a subject and an immediate family member is described. The smart device is possessed by an immediate family member. In this scenario, the subject leaves home to a destination.

Figure 30:
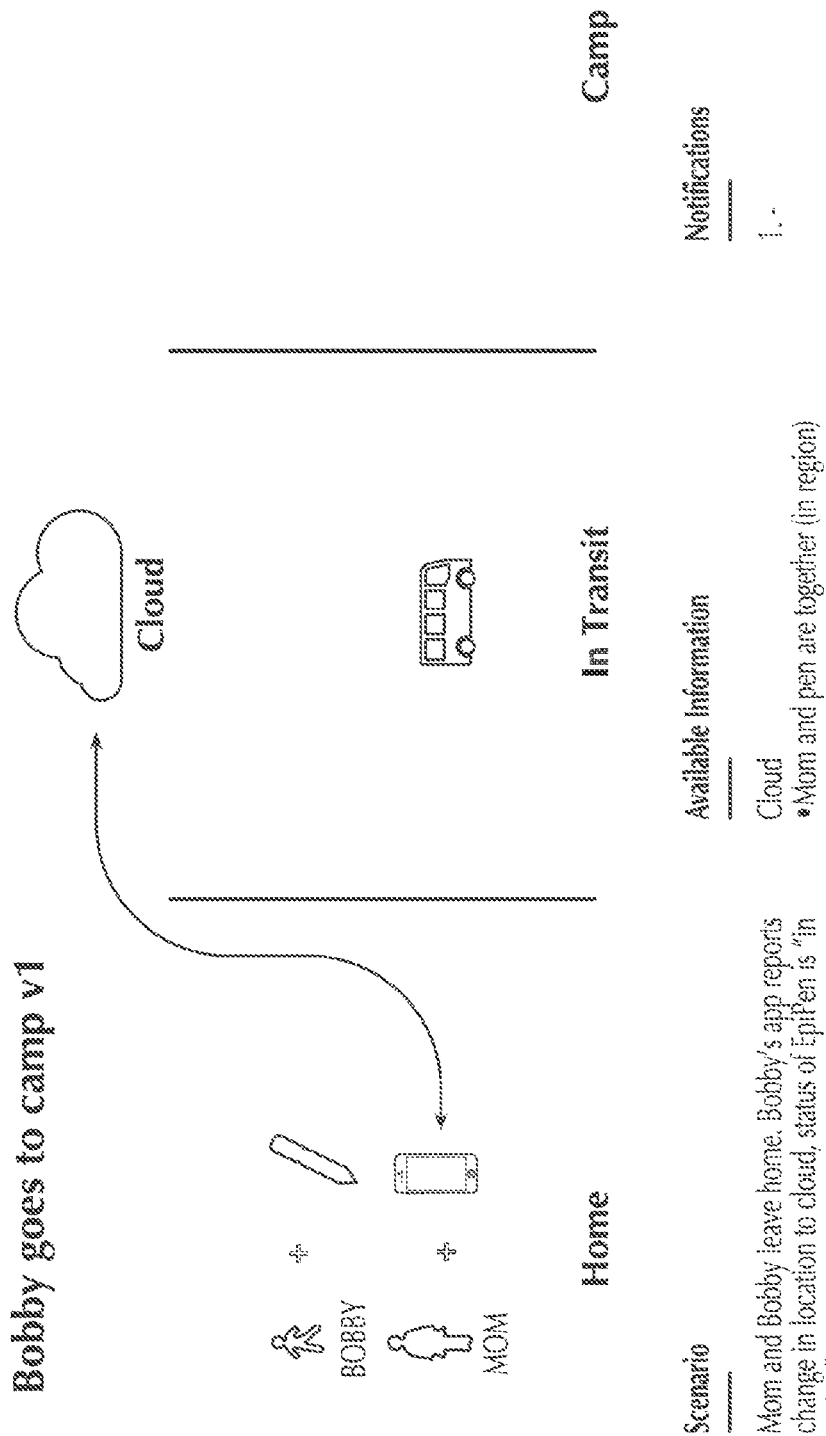
FIGS. 30-33 illustrate an exemplary system use scenario as described in Example 1.

Referring to FIG. 30, initially, the subject and immediate family member are at home. Accordingly, the sticker and smartphone are connected and are in the same region. The smart device reports the "in region" status to the cloud server, Based on this status, no notifications are made in the system.

Figure 31:
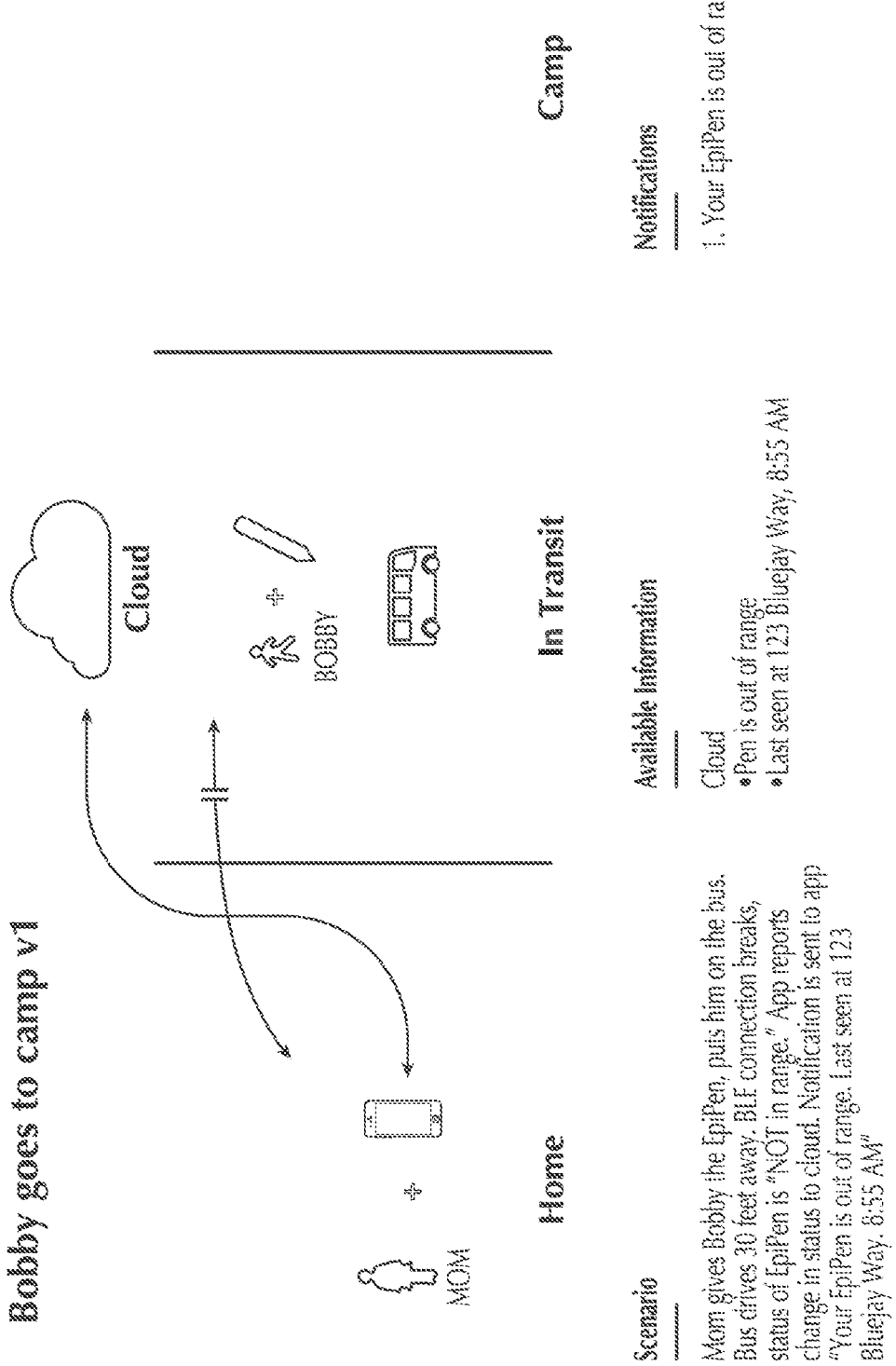

Next, in FIG. 31, the subject carries the sticker-attached epinephrine pen with him and moves in transit away from the immediate family member. The smart device eventually loses connection with the sticker, As a result, the smartphone determines that the epinephrine pen is out of the region. The smartphone then reports to cloud server the "out of region" status, e.g., via a base station, smartphone, or other connected device, and the location where it last co-localized with sticker, along with a timestamp. Based on this status, a status change notification is provided to subject on the smartphone.

Figure 32:
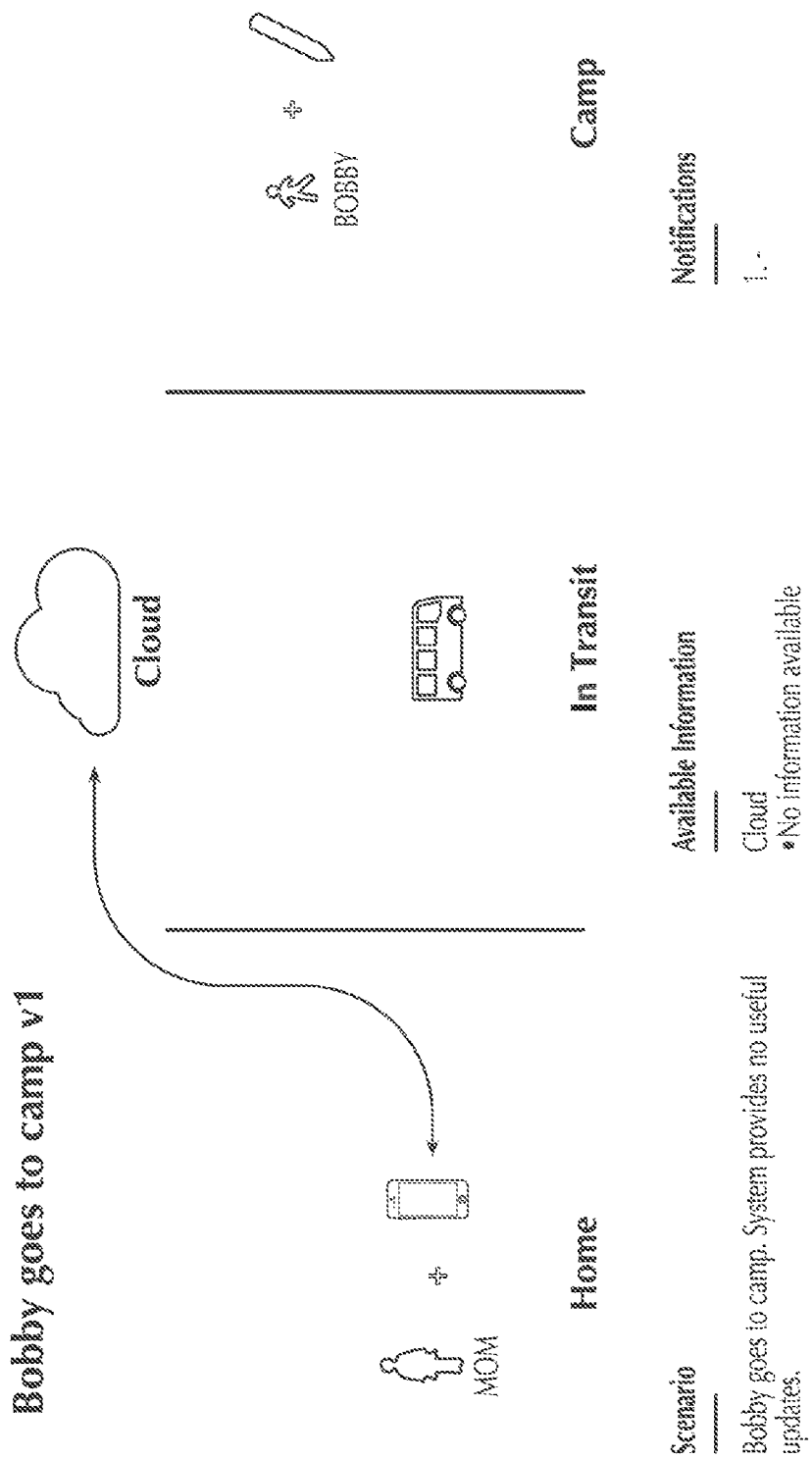

In FIG. 32, The subject arrives at the destination with the sticker-attached epinephrine pen. Because the sticker is neither connected to the smartphone nor cloud server, no new notifications are generated.

Figure 33:
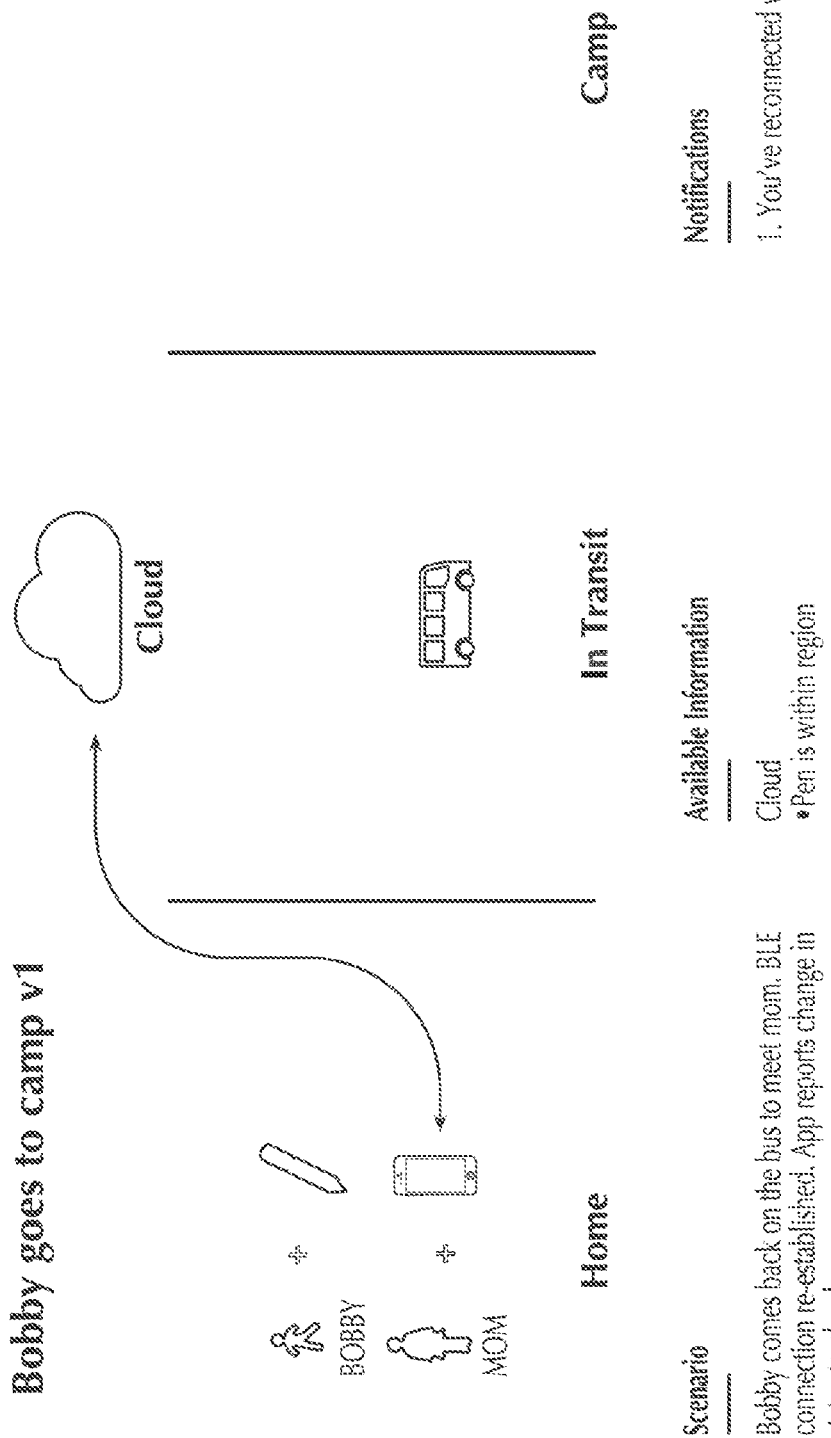

Finally, in FIG. 33, the subject returns to home carrying the sticker-attached epinephrine pen. The sticker and the smartphone are in the same region again and re-establishes connection with one another. Accordingly, the smartphone reports the "in region" status to the cloud server, Based on this status, a status change notification is provided to the subject on the smartphone.

Example 2

The use of a system comprising a sticker attached to an epinephrine pen, a first smartphone and a second smartphone by a subject and an immediate family member is described. Smart devices are possessed by the immediate family member and the subject, respectively. In this scenario, the subject leaves home to a destination.

Figure 34:
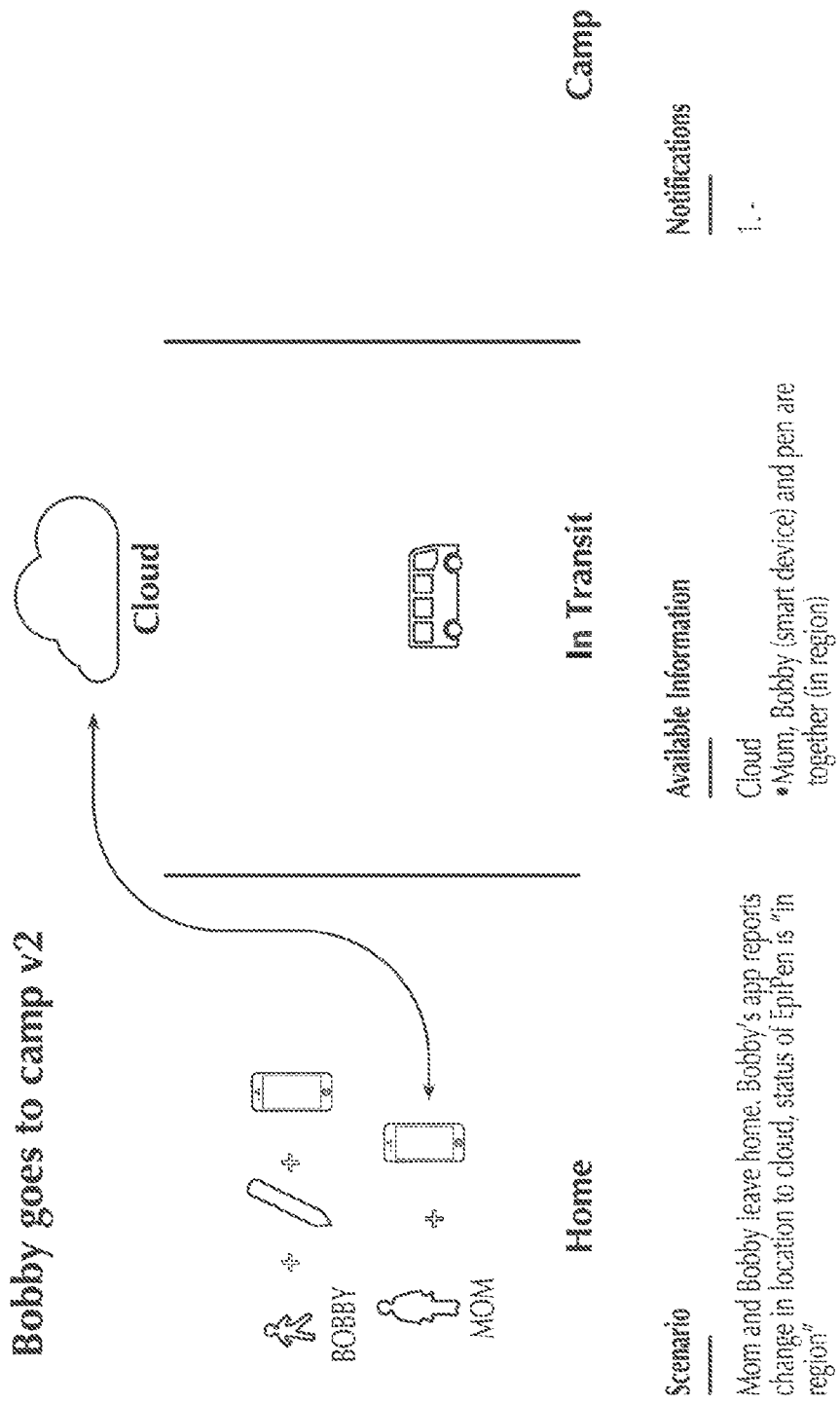
FIGS. 34-38 illustrate an exemplary system use scenario as described in Example 2.

Referring to FIG. 34, initially, the subject and immediate family member are at home, Accordingly, the sticker and smart devices are connected and are in the same region. Smartphone both report the "in region" status to the cloud server, Based on this status, no notifications are made in the system.

Figure 35:
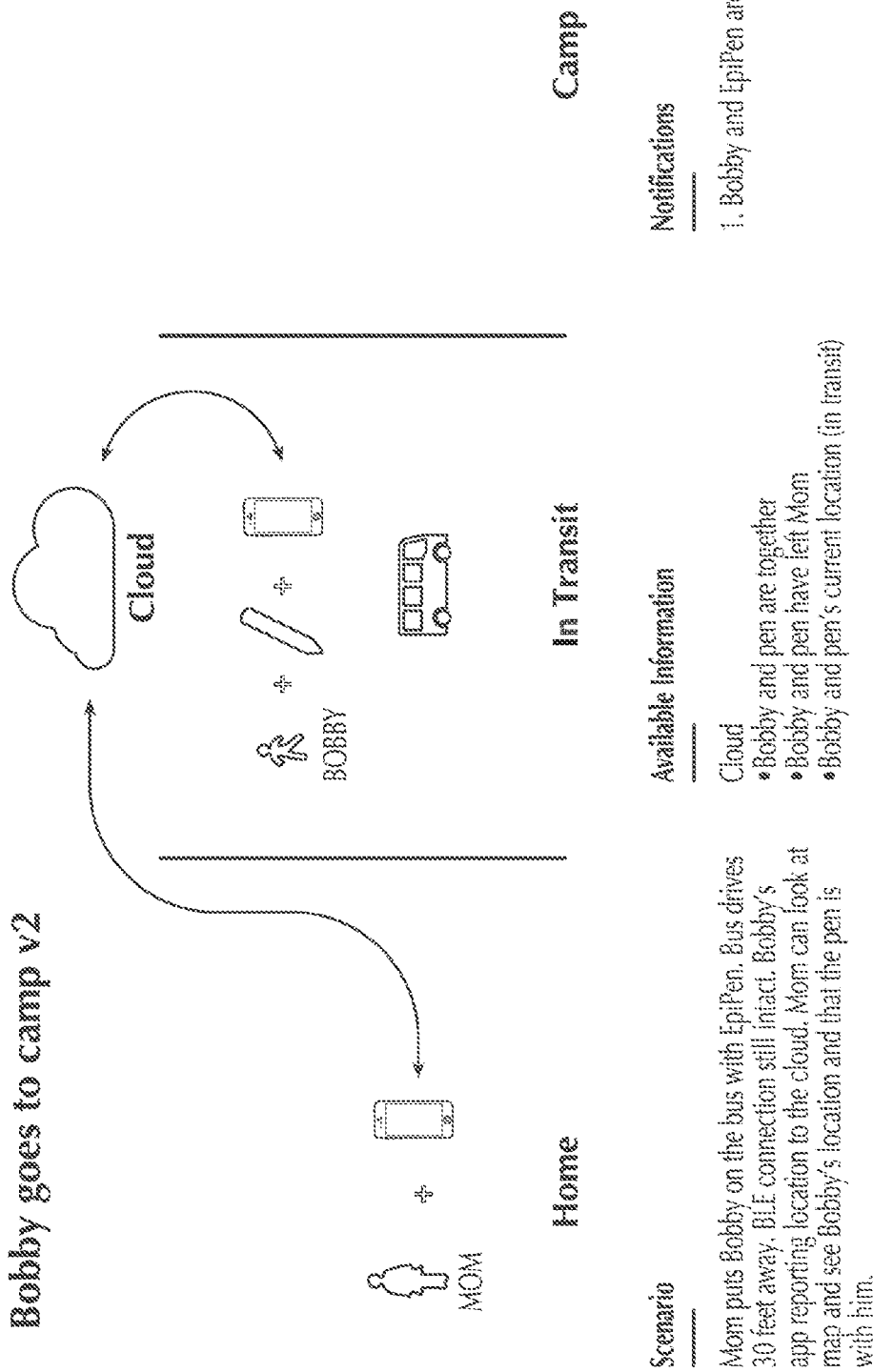

Next, referring to FIG. 35, the subject carries the sticker-attached epinephrine pen and a smartphone with him and moves in transit away from immediate family member, As the smartphone loses connection with the sticker after subject is more than about 30 feet away, the smartphone remains connected with the sticker. The smartphone determines that the epinephrine pen is out of the region and reports the "out of region" status to the cloud. However, because the smartphone remains in region with the sticker, the "out of region" status is overridden. As a result, the smartphone provides to the immediate family member a notification that both the subject and the epinephrine pen are out of region, The immediate family member has the option to review the location of smartphone as the subject is in transit to the destination.

Figure 36:
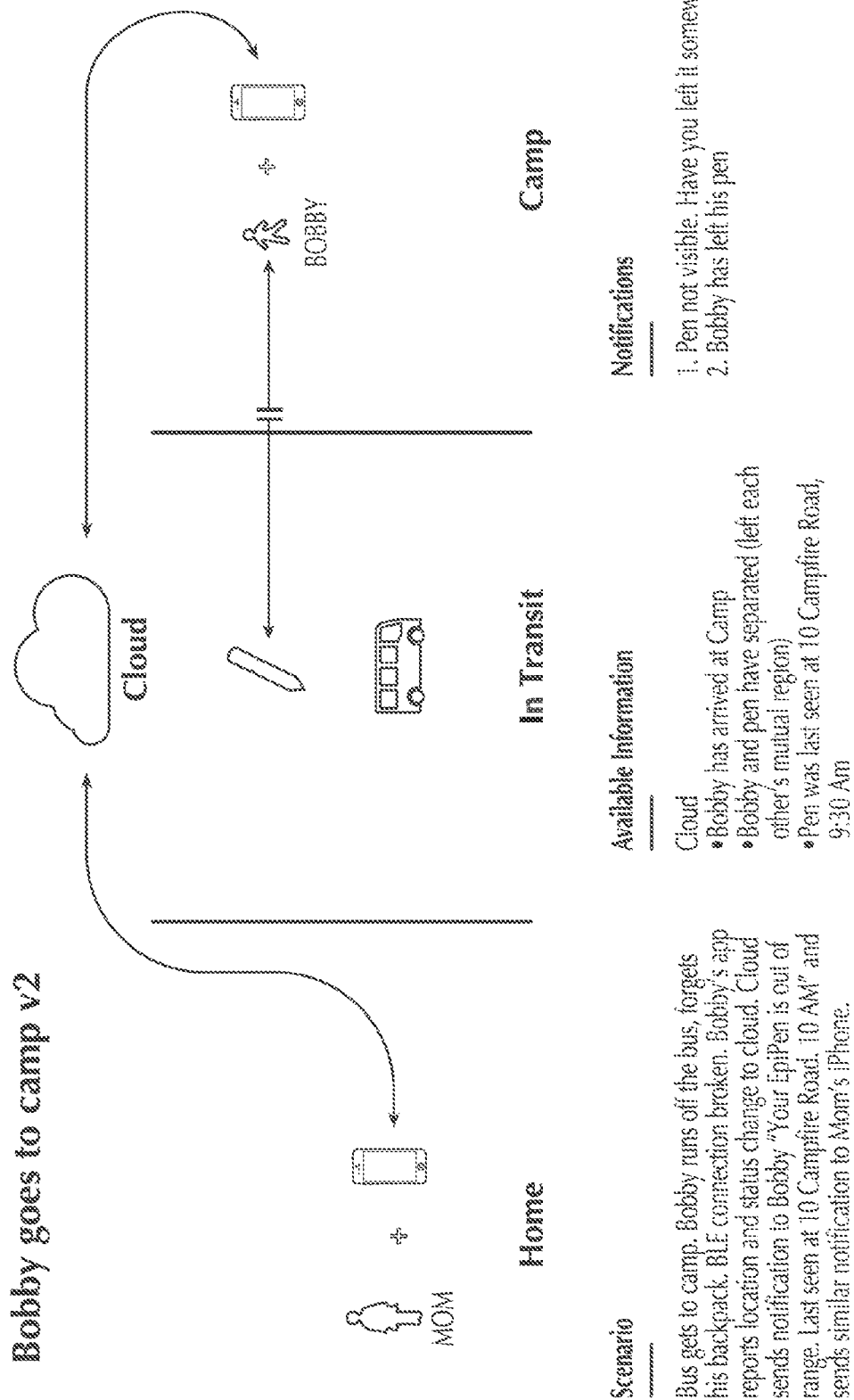

Referring to FIG. 36, the subject arrives at the destination having only the smartphone with him but not the sticker-attached epinephrine pen. Both smartphones lose connection with the sticker. Because the smartphone is the last smart device that lost connection with the sticker, the smartphone would report to the cloud the "out of region" status and the location where it last co-localized with the sticker, along with a timestamp. As a result, the smartphone provides to the subject a notification that the epinephrine pen is out of region. A notification that the subject has separated from his epinephrine pen is also provided to the smartphone to the attention of immediate family member.

Figure 37:
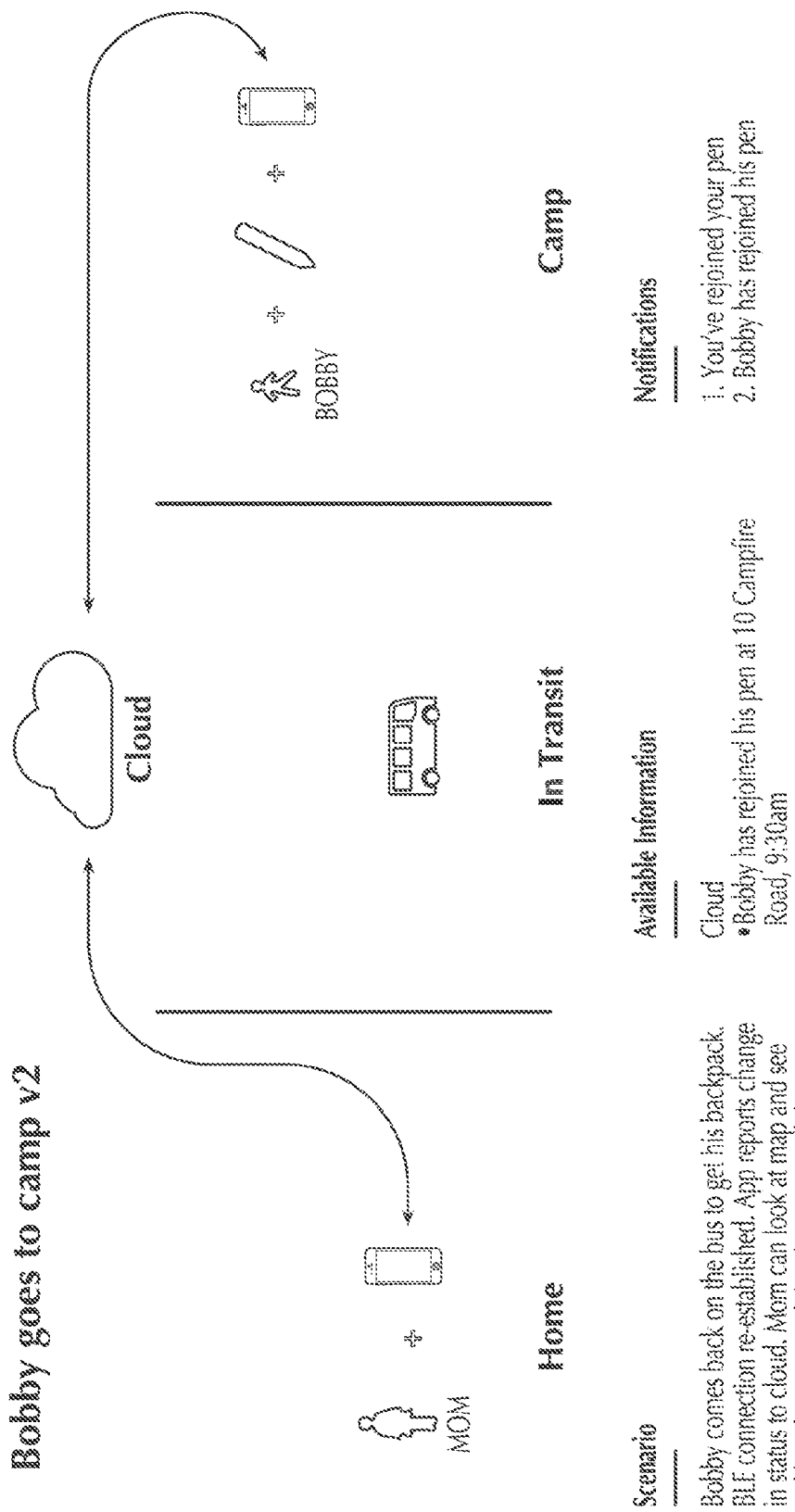

Referring to FIG. 37, the subject successfully recovers his epinephrine pen. Therefore, the sticker and smartphone are once again in the same region and re-establish connection with each other. Upon re-connection, the smartphone reports the "in region" status to the cloud server, As a result, the smartphone provides to the subject a notification confirming that the epinephrine pen is once again in region. A notification that the subject has recovered his epinephrine pen is also provided to the smartphone to the attention of immediate family member.

Figure 38:
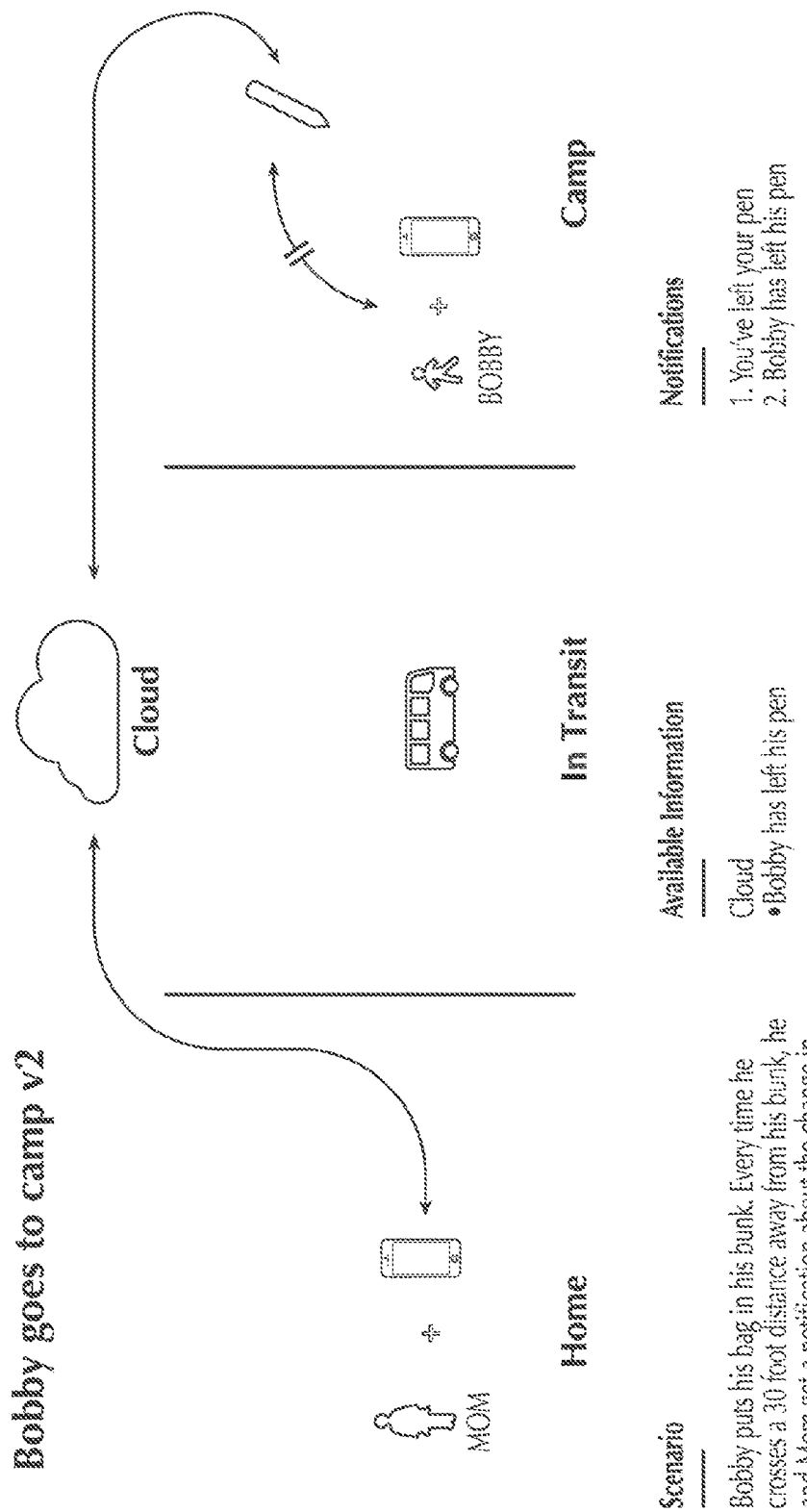

Referring to FIG. 38, the subject, carrying a smartphone, is separated from the epinephrine pen attached to a the sticker for more than 30 feet. Both smartphones lose connection with the sticker. Because the smartphone is the last smart device that lost connection with the sticker, the smartphone would report to the cloud the "out of region" status and the location where it last co-localized with the sticker, along with a timestamp. As a result, the smartphone provides to the subject a notification that the epinephrine pen is out of region. A notification that the subject has separated from his epinephrine pen is also provided to the smartphone to the attention of immediate family member.

Example 3

The use of a system comprising a the sticker attached to an epinephrine pen, a wearable, and a smartphone by a subject and an immediate family member is described. The subject possesses a wearable, A smartphone is possessed by an immediate family member, In this scenario, the subject leaves home to a destination.

Figure 39:
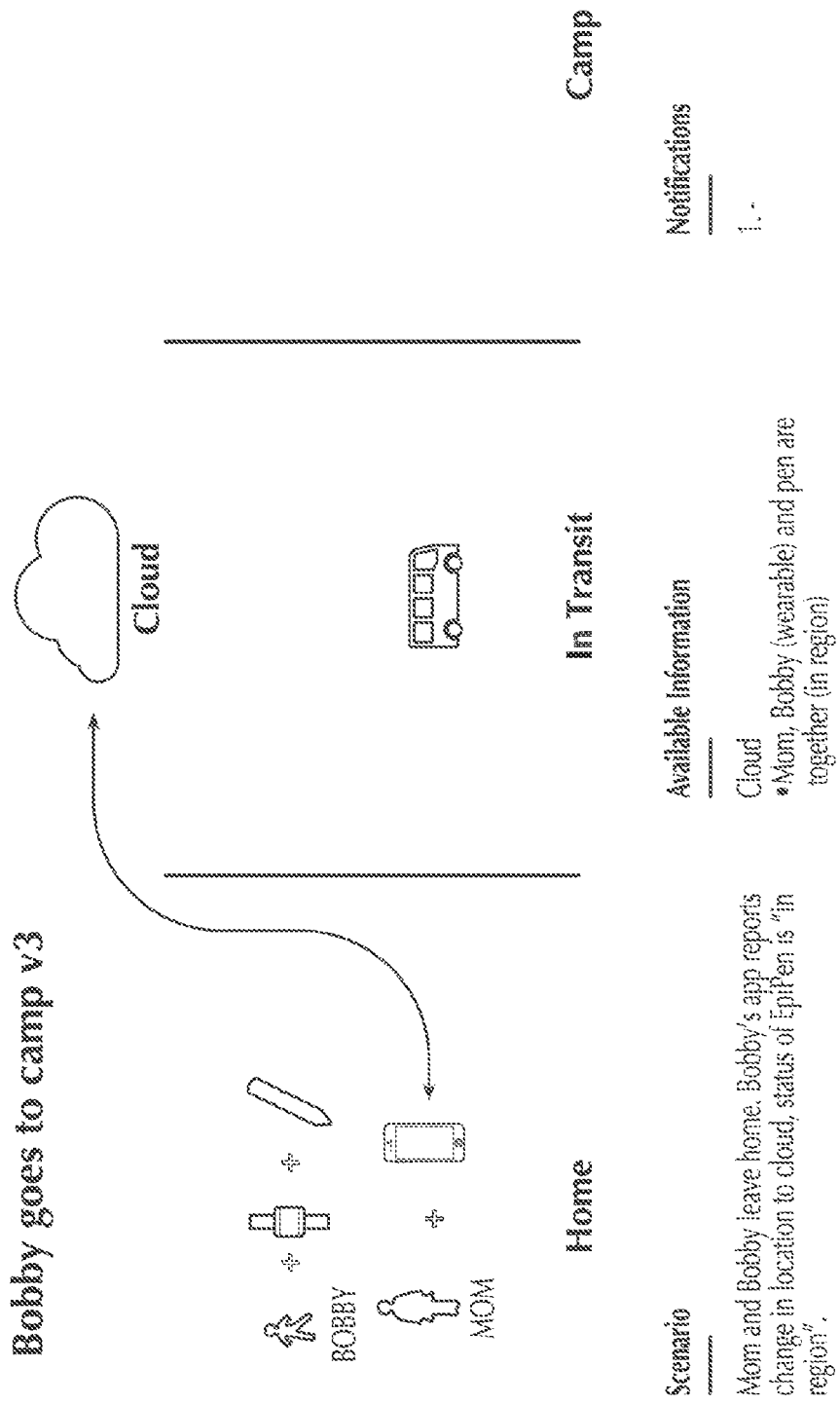
FIGS. 39-43 illustrate an exemplary system use scenario as described in Example 3.

Referring to FIG. 39, initially, the subject and the immediate family member are at home, Accordingly, the sticker, wearable, and smartphone are connected and are in the same region. The smartphone reports the "in region" status to the cloud server, Based on this status, no notifications are made in the system.

Figure 40:
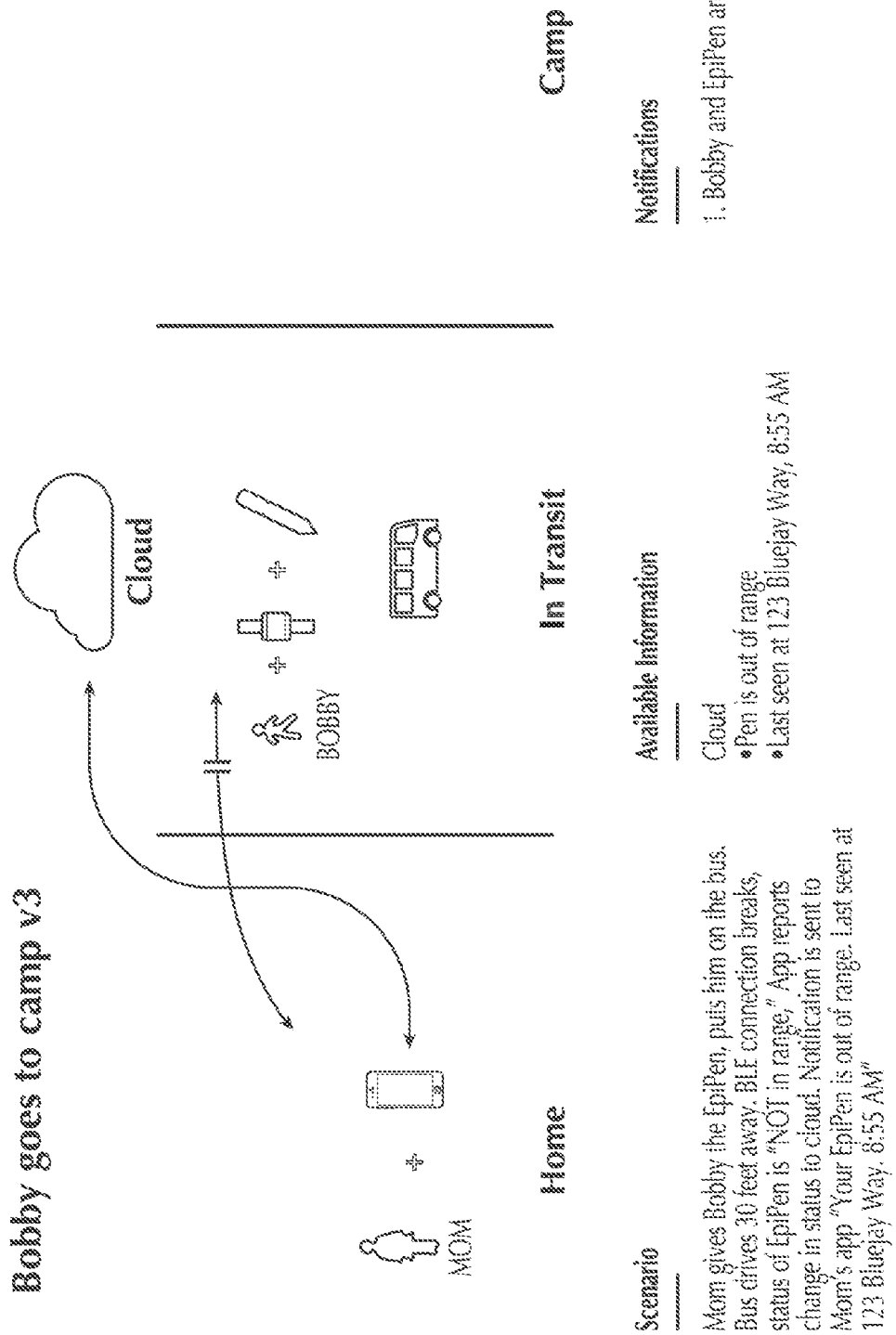

Next, referring to FIG. 40, the subject carries the sticker-attached epinephrine pen and wearable with him and moves in transit away from the immediate family member. As the smartphone loses connection with both the sticker and the wearable after the subject is more than about 30 feet away, the smartphone determines that the epinephrine pen is out of the region and reports the "out of region" status and the location where it last co-localized with the sticker to the cloud. As a result, the smartphone provides to immediate family member a notification that both the subject and the epinephrine pen are out of region.

Figure 41:
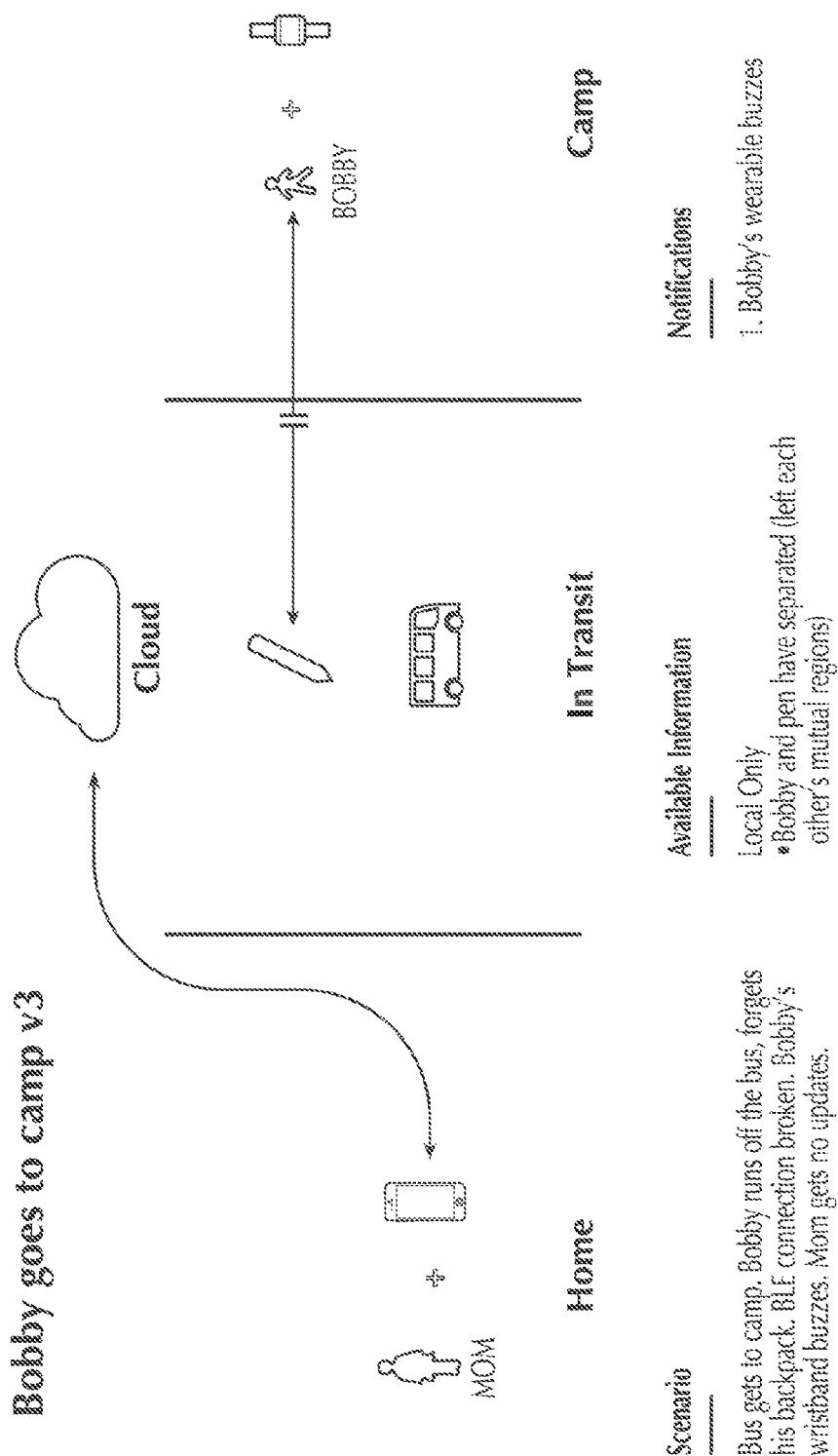

Referring to FIG. 41, the subject arrives at the destination having only the wearable with him but not the sticker-attached epinephrine pen. The wearable loses connection with the sticker, which would trigger the wearable to vibrate. Such vibrations would notify the subject that he has separated from the epinephrine pen. However, because the wearable is not connected to the cloud, no additional notification would be provided to the smartphone.

Figure 42:
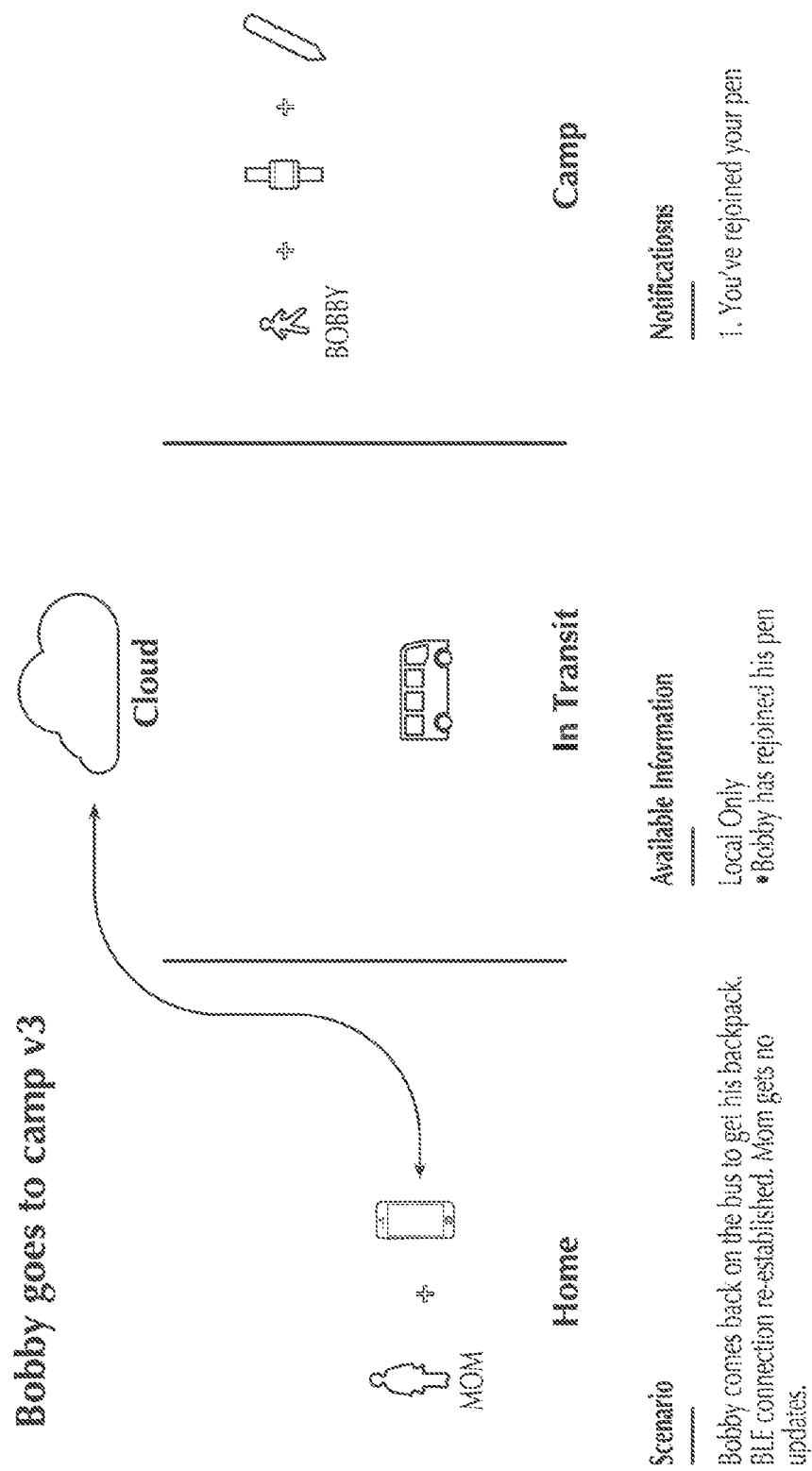

Referring to FIG. 42, the subject successfully recovers his epinephrine pen. Therefore, the sticker and wearable are once again in the same region and re-establish connection with one another. Upon re-connection, the wearable provides to the subject a notification confirming that the epinephrine pen is once again in region. Again, because the wearable is not connected to the cloud, no additional notification would be provided to the smartphone.

Figure 43:
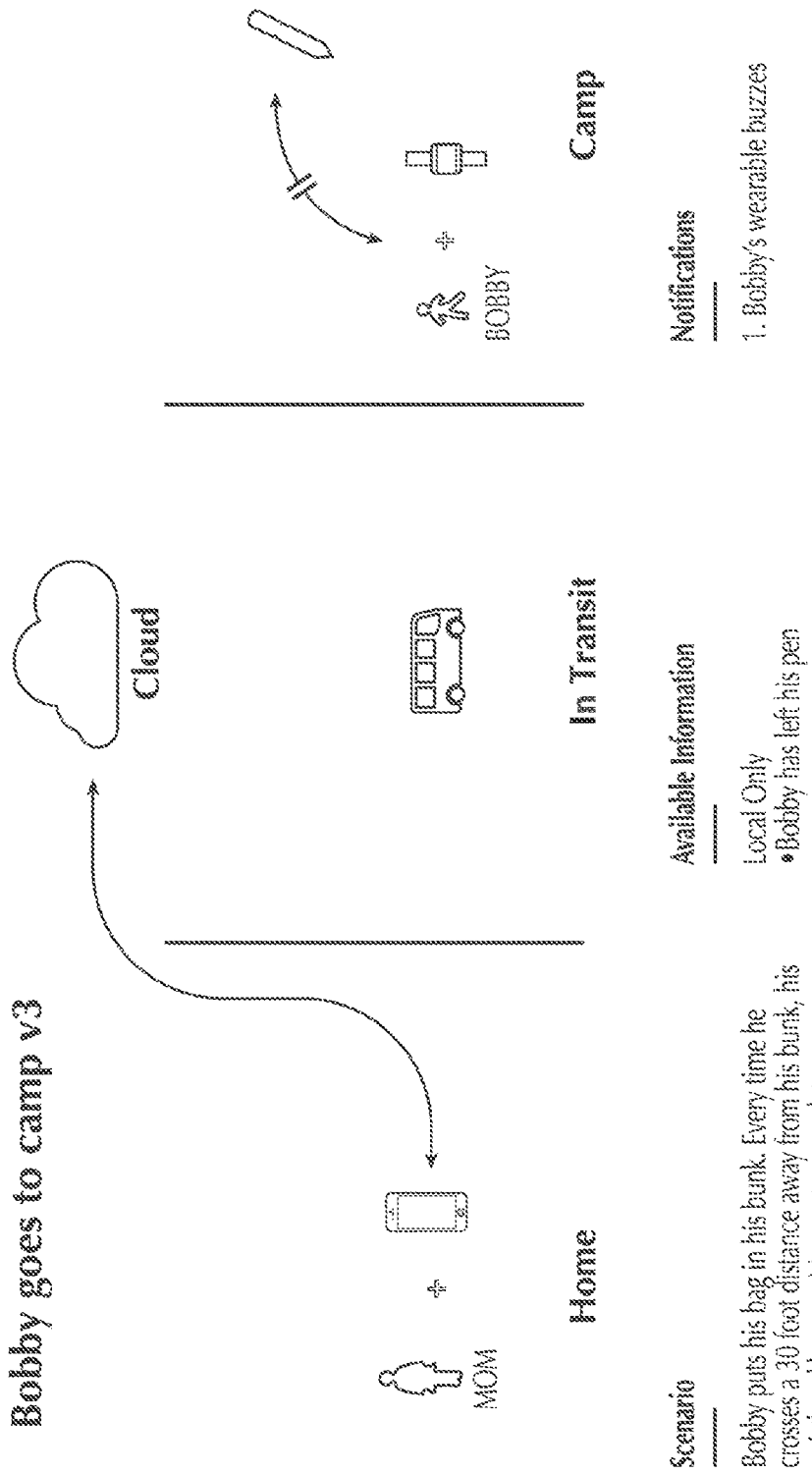

Referring to FIG. 43, the subject wearing the wearable is separated from the epinephrine pen attached to a the sticker for more than 30 feet. The wearable loses connection with the sticker, which would trigger the wearable to vibrate. Such vibrations would notify the subject that he has separated from the epinephrine pen. However, because the wearable is not connected to the cloud, no additional notification would be provided to smartphone.

Example 4

The use of a system comprising a sticker attached to an epinephrine pen, a first smartphone and a second, other smartphone by a subject, an immediate family member, and a level 1 caregiver is described. The smartphones are possessed by an immediate family member and a level 1 caregiver, respectively. In this scenario, the subject leaves home to a destination.

Figure 44:
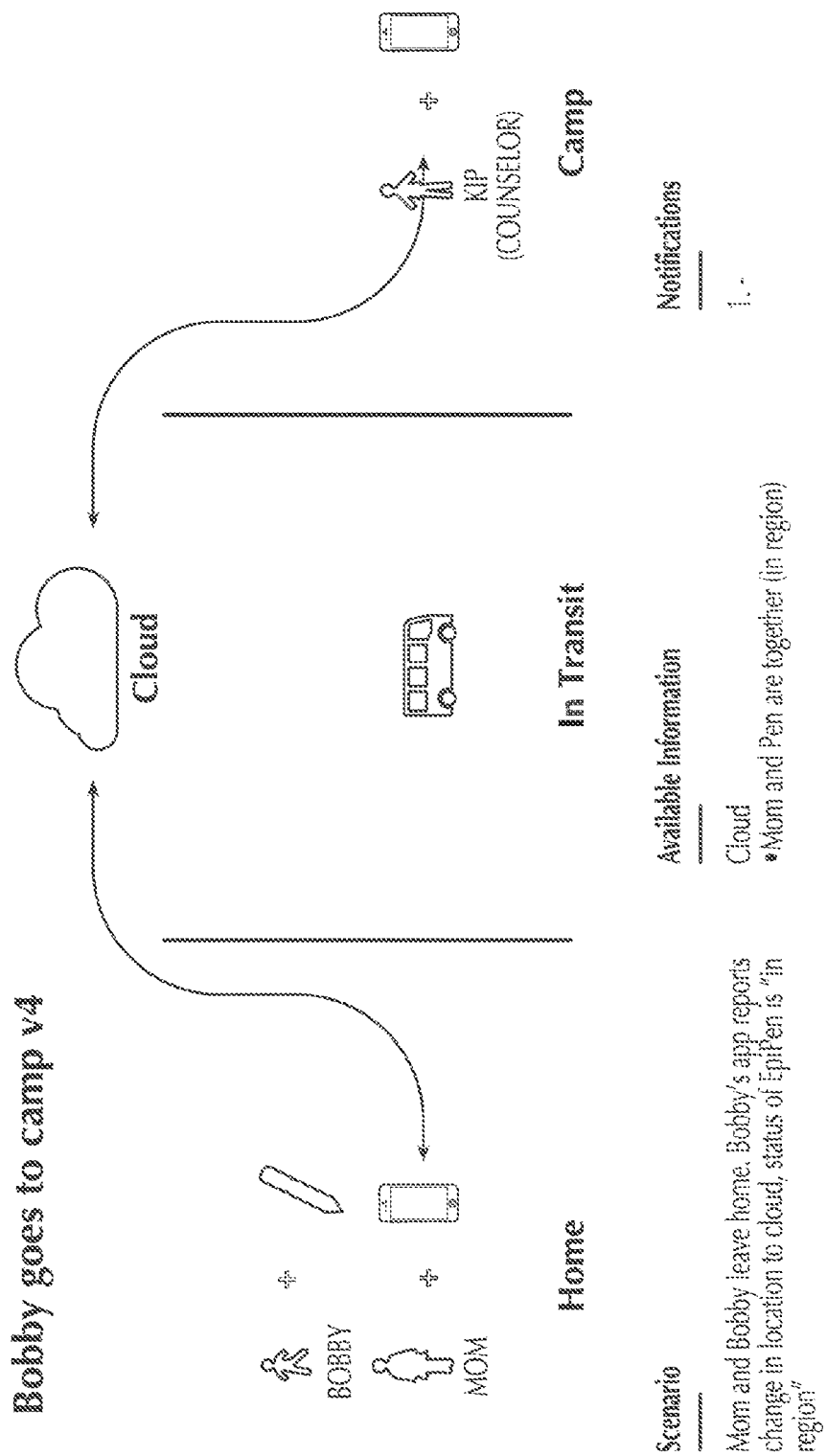
FIGS. 44-47 illustrate an exemplary system use scenario as described in Example 4.

Referring to FIG. 44, initially, the subject and immediate family member are at home, and the level 1 caregiver is present at destination. Accordingly, the sticker and smartphone are connected and are in the same region. The smartphone reports the "in region" status to the cloud server, Although the other smartphone is paired to the sticker but disconnected, the level 1 caregiver has not yet been granted responsibility of the subject. In this case, the cloud server would allow the status reported by the smartphone to override the status reported by the other smartphone. Based on the "in region" status, no notifications are made in the system.

Figure 45:
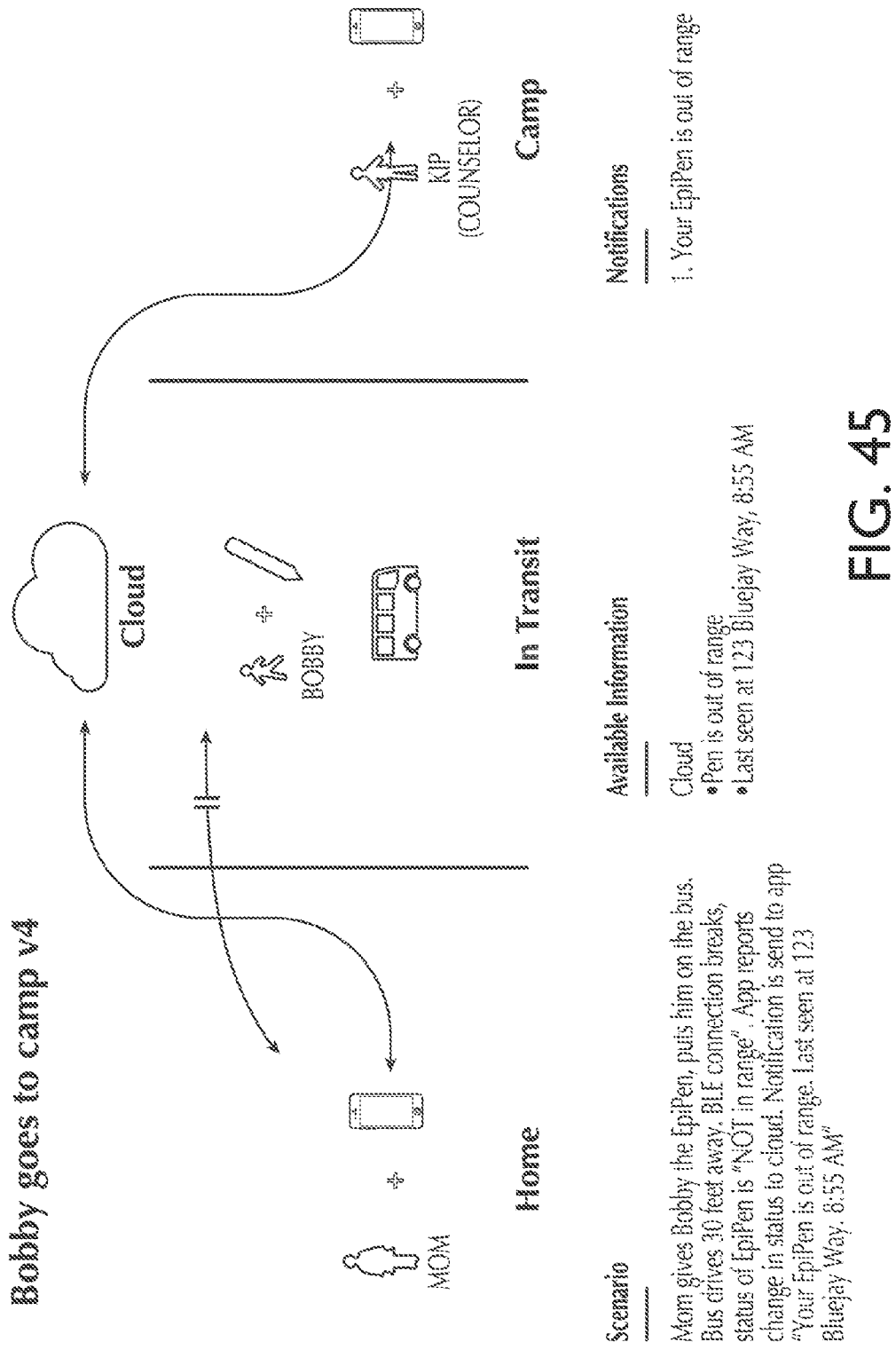

Next, referring to FIG. 45, the subject carries the sticker-attached epinephrine pen with him and moves in transit away from the immediate family member. As the smartphone loses connection with the sticker after the subject is more than about 30 feet away, both smartphones are disconnected with the sticker. The smartphone determines that the epinephrine pen is out of the region and reports the "out of region" status and the location where it last co-localized with the sticker to the cloud. As a result, the smartphone provides to the immediate family member a notification that both the subject and the epinephrine pen are out of region.

Figure 46:
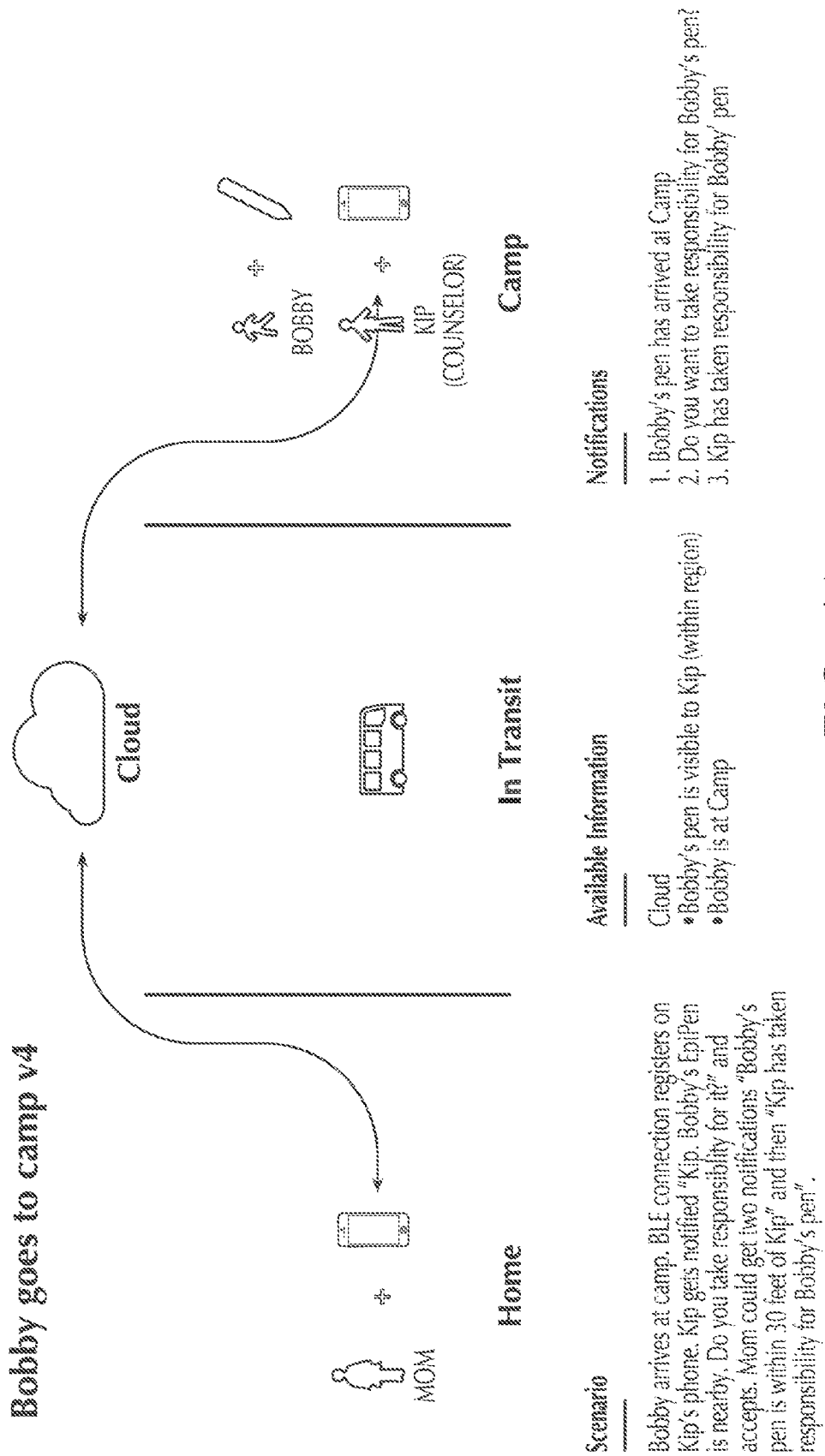

Referring to FIG. 46, the subject arrives at the destination carrying the sticker-attached epinephrine pen. Because the sticker is paired with the other smartphone, a connection between the sticker and the other smartphone would be established upon the arrival of the subject at destination, The level 1 caregiver would be given the option to accept the transferred responsibility to track the epinephrine pen. Upon acceptance of the responsibility, the other smartphone would report to the cloud that the epinephrine pen is "in region." Based on the "in region" status, the immediate family member would be notified through smartphone that the level 1 caregiver is in region with the epinephrine pen.

Figure 47:
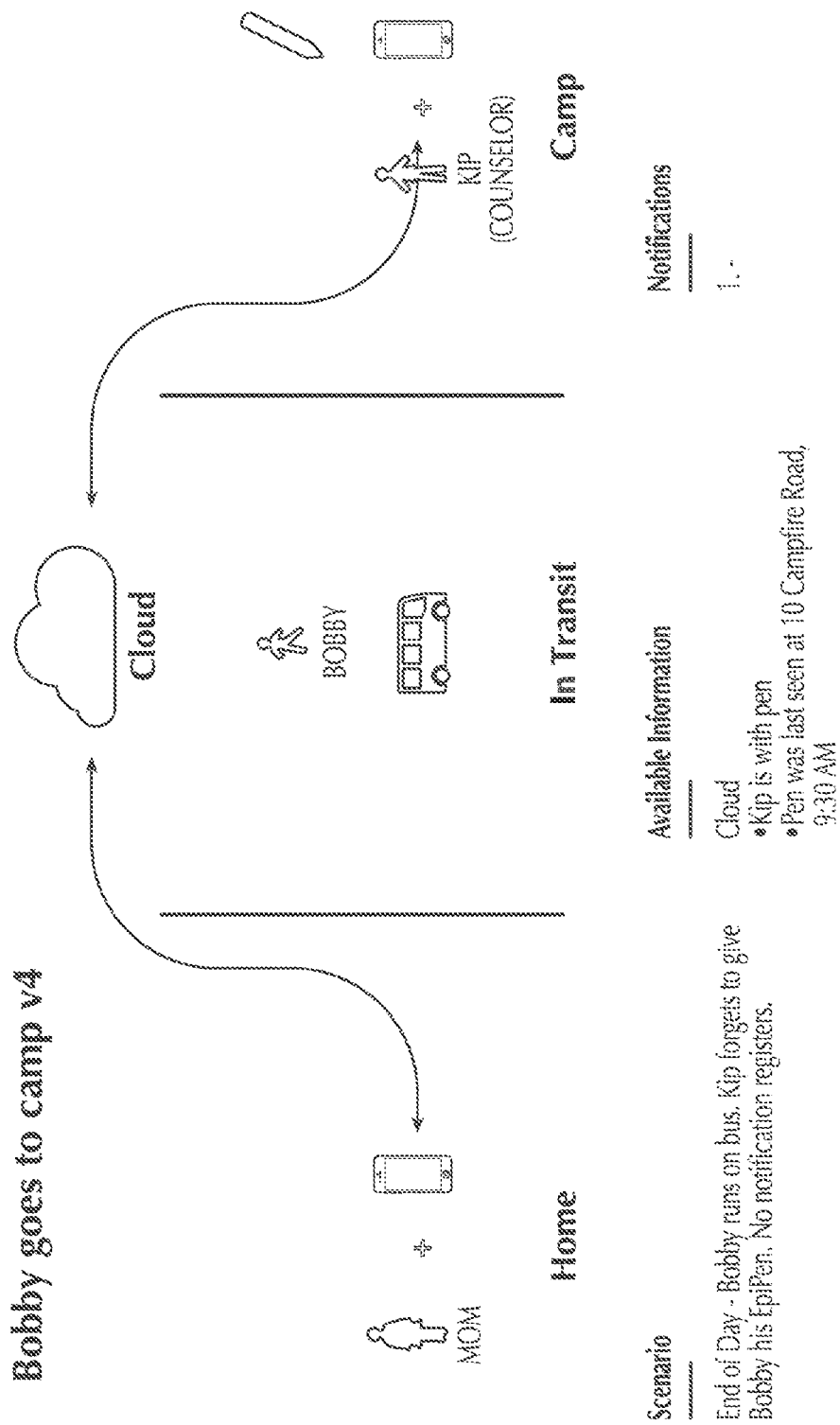

Referring to FIG. 47, the subject is in transit and is separated from the epinephrine pen attached to a the sticker for more than 30 feet. The other smartphone remains connected with the sticker. Accordingly, no additional notification would be provided to either smartphone.

Example 5

The use of a system comprising a sticker attached to an epinephrine pen, three smartphones by a subject, an immediate family member, and a level 1 caregiver is described. The smartphones are possessed by the immediate family member, the subject, and the level 1 caregiver, respectively. In this scenario, the subject leaves home to a destination.

Figure 48:
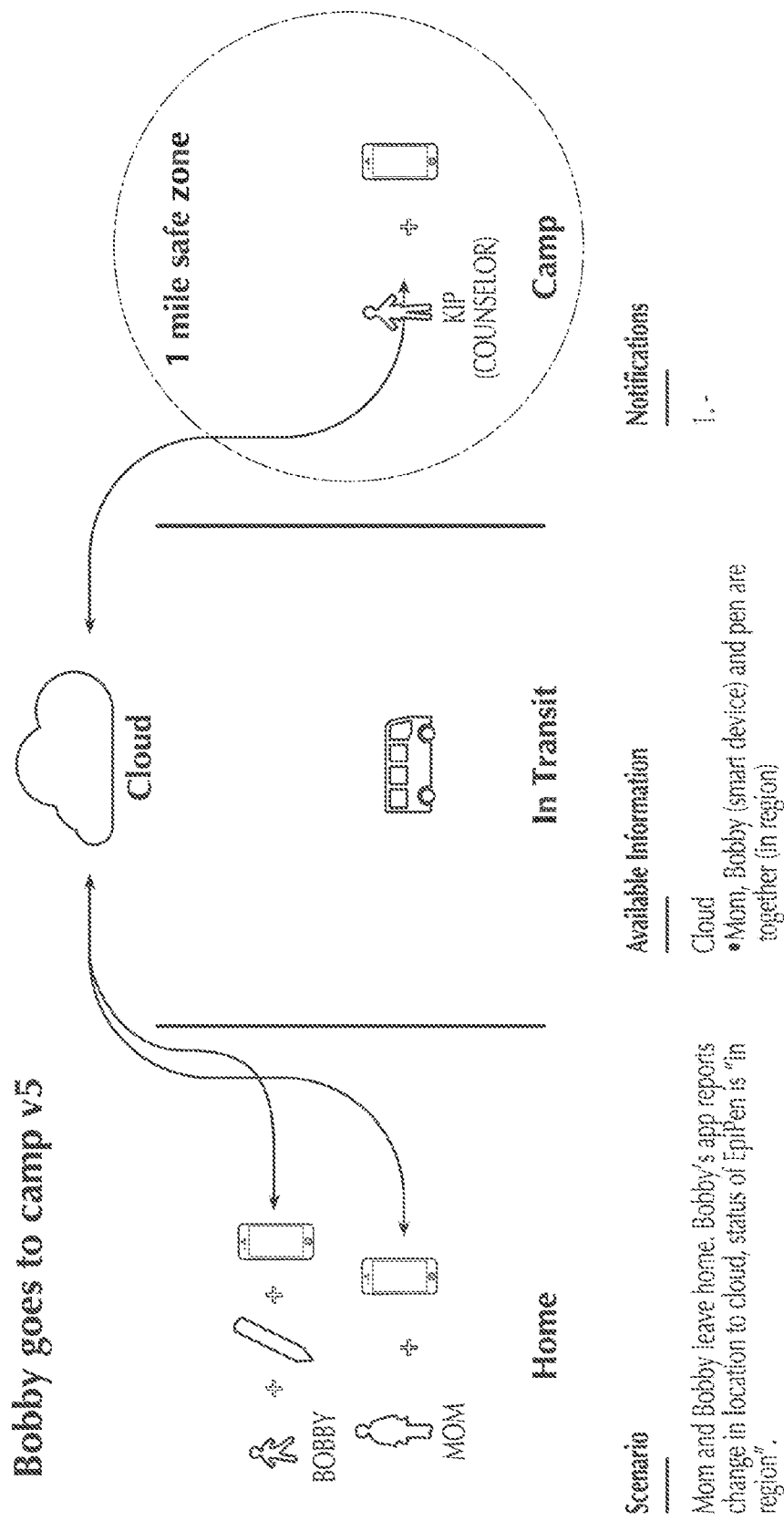
FIGS. 48-52 illustrate an exemplary system use scenario as described in Example 5.

Referring to FIG. 48, initially, the subject and the immediate family member are at home, and the level 1 caregiver is present at the destination, Accordingly, the sticker and the first and second smartphones are connected and are in the same region. The first and second smartphones report the "in region" status to the cloud server. Although the third smartphone is paired to the sticker but disconnected, the level 1 caregiver has not yet been granted responsibility of the subject. In this case, the cloud server would allow the statuses reported by the first and second smartphones to override the status reported by the third smartphone. Based on the "in region" status, no notifications are made in the system.

Figure 49:
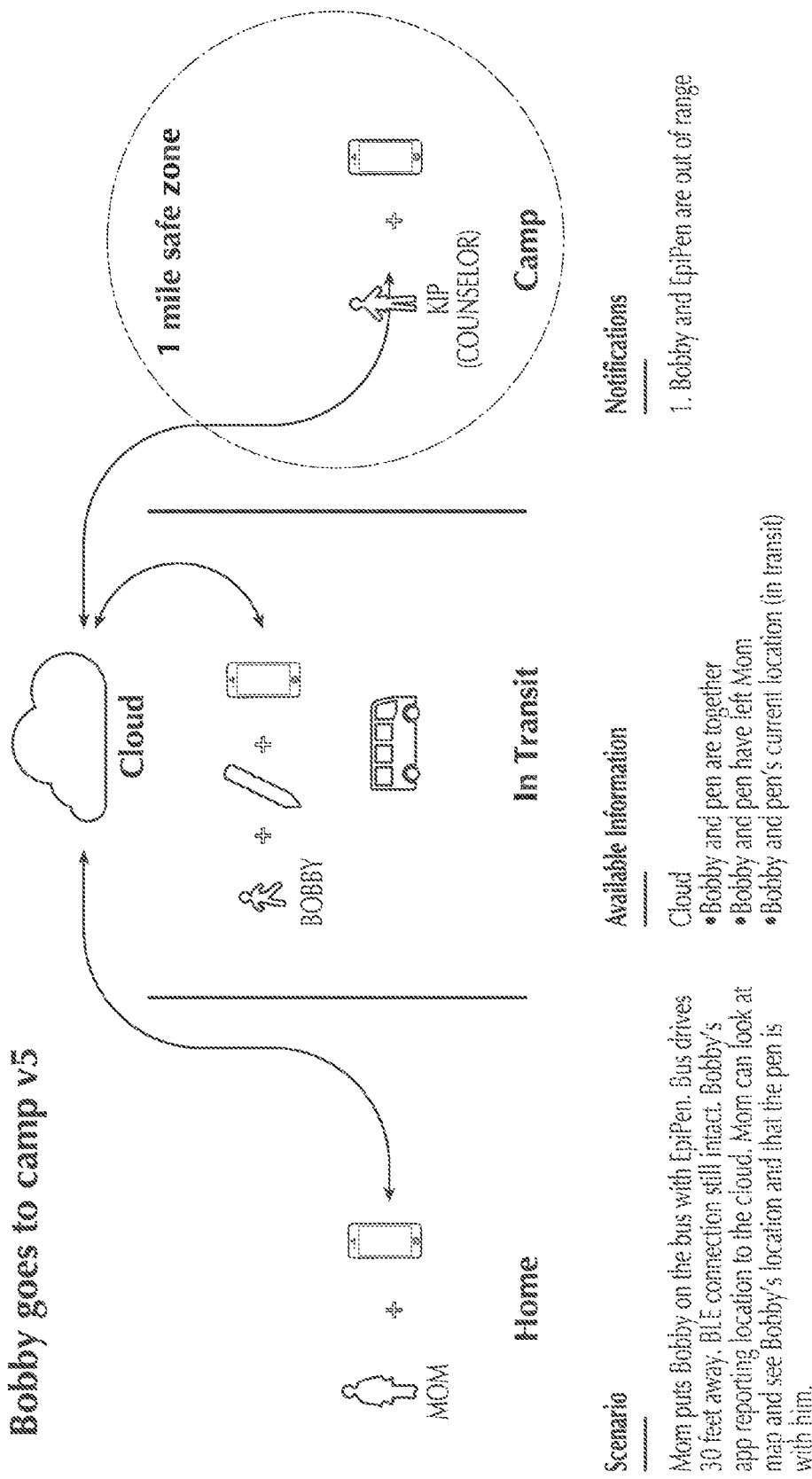

Next, referring to FIG. 49, the subject carries the sticker-attached epinephrine pen as well as the second smartphone with him and moves in transit away from the immediate family member. As the first smartphone loses connection with the sticker after the subject is more than about 30 feet away, the second smartphone remains connected with the sticker. The first smartphone determines that the epinephrine pen is out of the region and reports the "out of region" status to the cloud. However, because the second smartphone remains in region with the sticker, the "out of region" status is overridden. As a result, the first smartphone provides to the immediate family member a notification that both the subject and the epinephrine pen are out of region. The immediate family member has the option to review the location of the second smartphone as the subject is in transit to destination.

Figure 50:
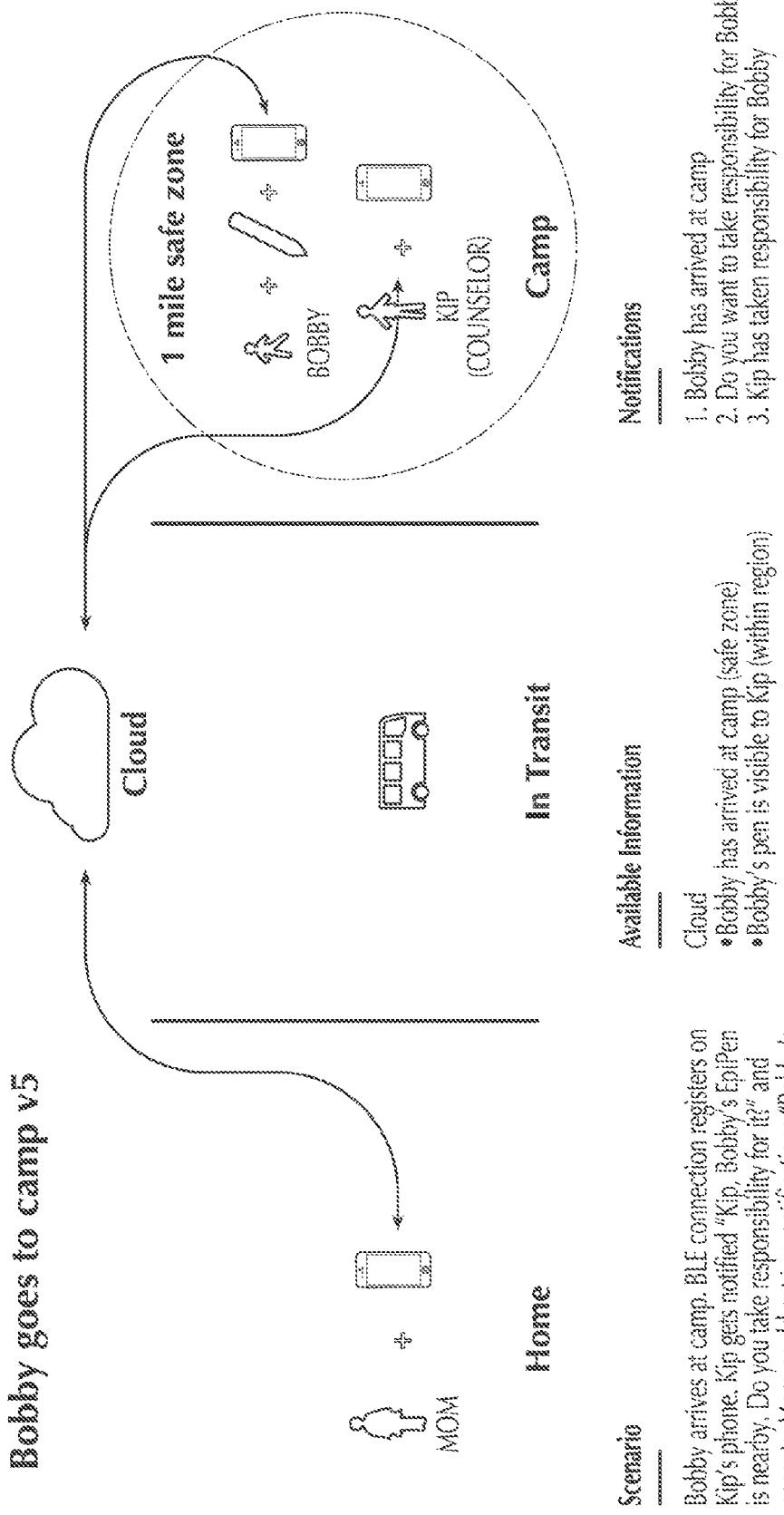

Referring to FIG. 50, the subject arrives at the destination carrying both the sticker-attached epinephrine pen and the second smartphone. The second smartphone continues to report an "in region" status to the cloud. Because the sticker is paired with the third smartphone, a connection between the sticker and the third smartphone would be established upon the arrival of the subject at the destination. The level 1 caregiver would be given the option to accept the transferred responsibility to track the epinephrine pen. Upon acceptance of the responsibility, the third smartphone would report to the cloud that the epinephrine pen is "in region." Based on the "in region" statuses provided by the second and third smartphones, the immediate family member would be notified through the first smartphone that the subject and the level 1 caregiver are in region with the epinephrine pen.

Figure 51:
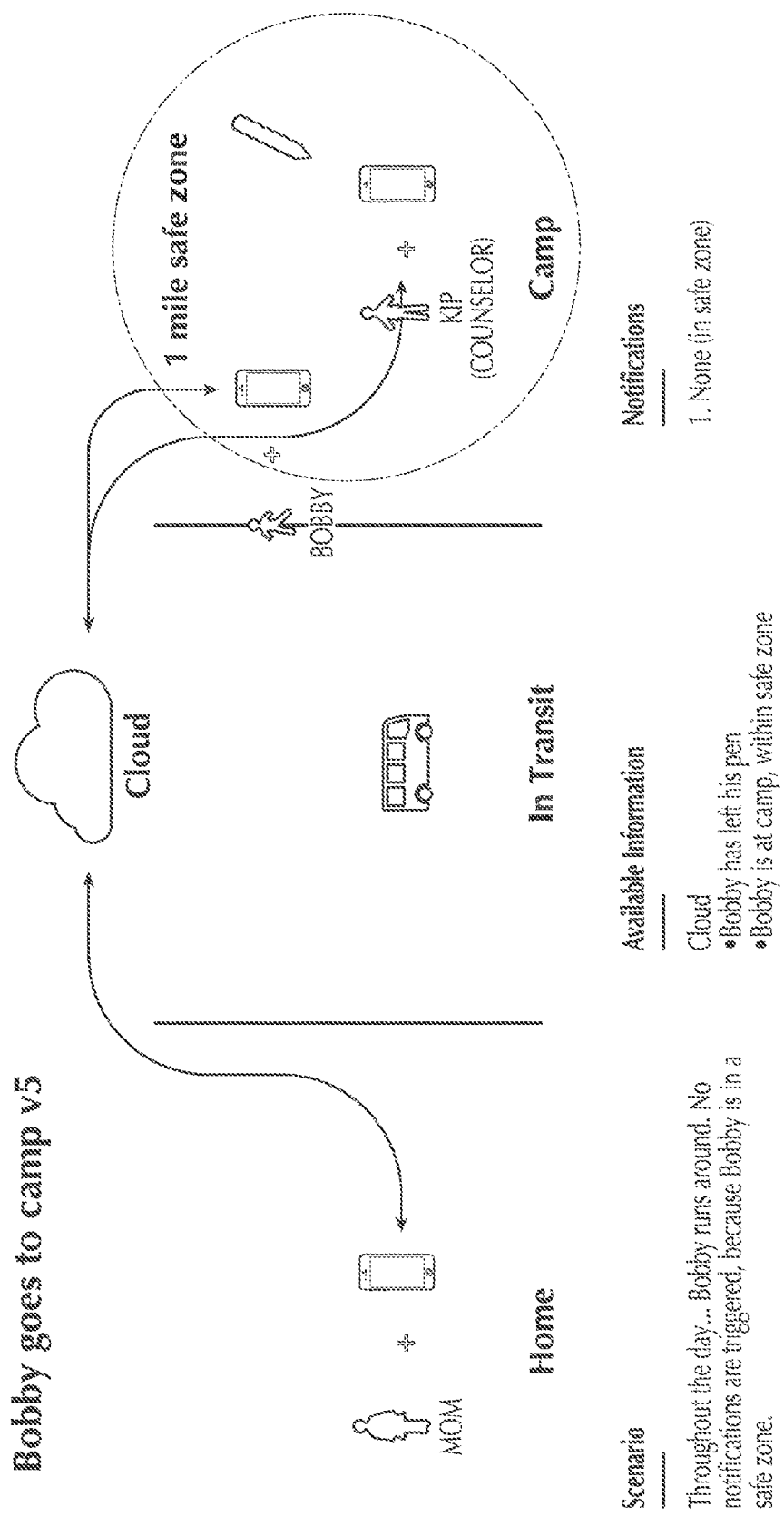

Referring to FIG. 51, the subject carrying the second smartphone is separated from the epinephrine pen attached to a the sticker for more than 30 feet. The second smartphone is disconnected from the sticker. Nonetheless, the second and third smartphones are within a 1 mile safe zone distance, and the third smartphone remains connected to the sticker. Accordingly, the second smartphone determines that the sticker device is still "in region." Accordingly, no additional notification would be provided to any smartphones.

Figure 52:
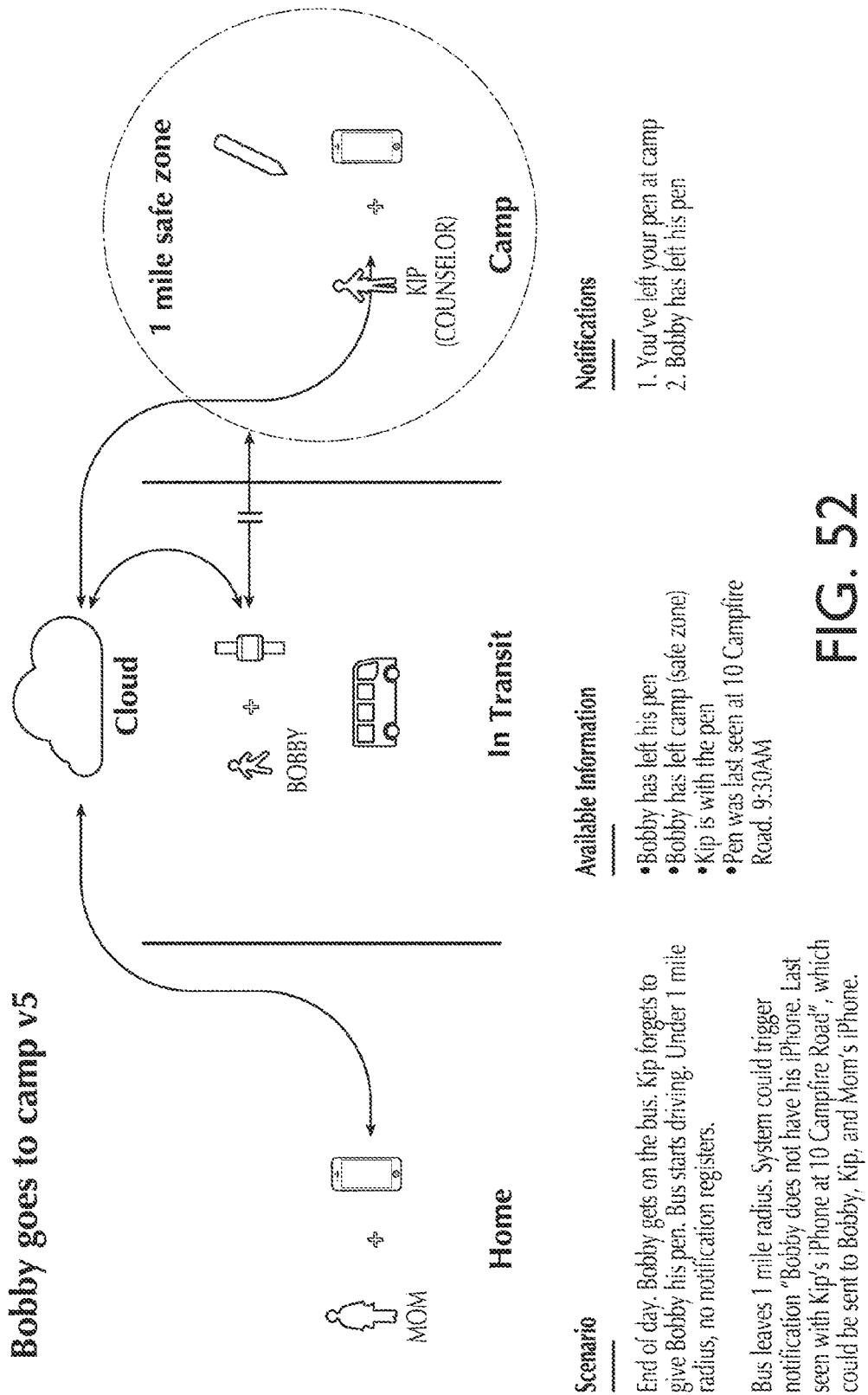

Finally, referring to FIG. 52, the subject carrying the second smartphone is in transit and is outside of the 1 mile safe zone as defined by the co-localization of the third smartphone and the sticker. The third smartphone is the only device that is connected with the sticker. The second smartphone determines that the sticker is "out of region," and reports such status information to cloud server. As a result, smartphones provide to all the team members a notification that both subject has left the epinephrine pen with level 1 caretaker.

Example 6

The use of a system comprising a sticker attached to an epinephrine pen, two smartphones, and a wearable by a subject, an immediate family member, and a level 1 caregiver is described. The first and second smartphones are possessed by the immediate family member and the level 1 caregiver, respectively. In this scenario, the subject leaves home to a destination.

Figure 53:
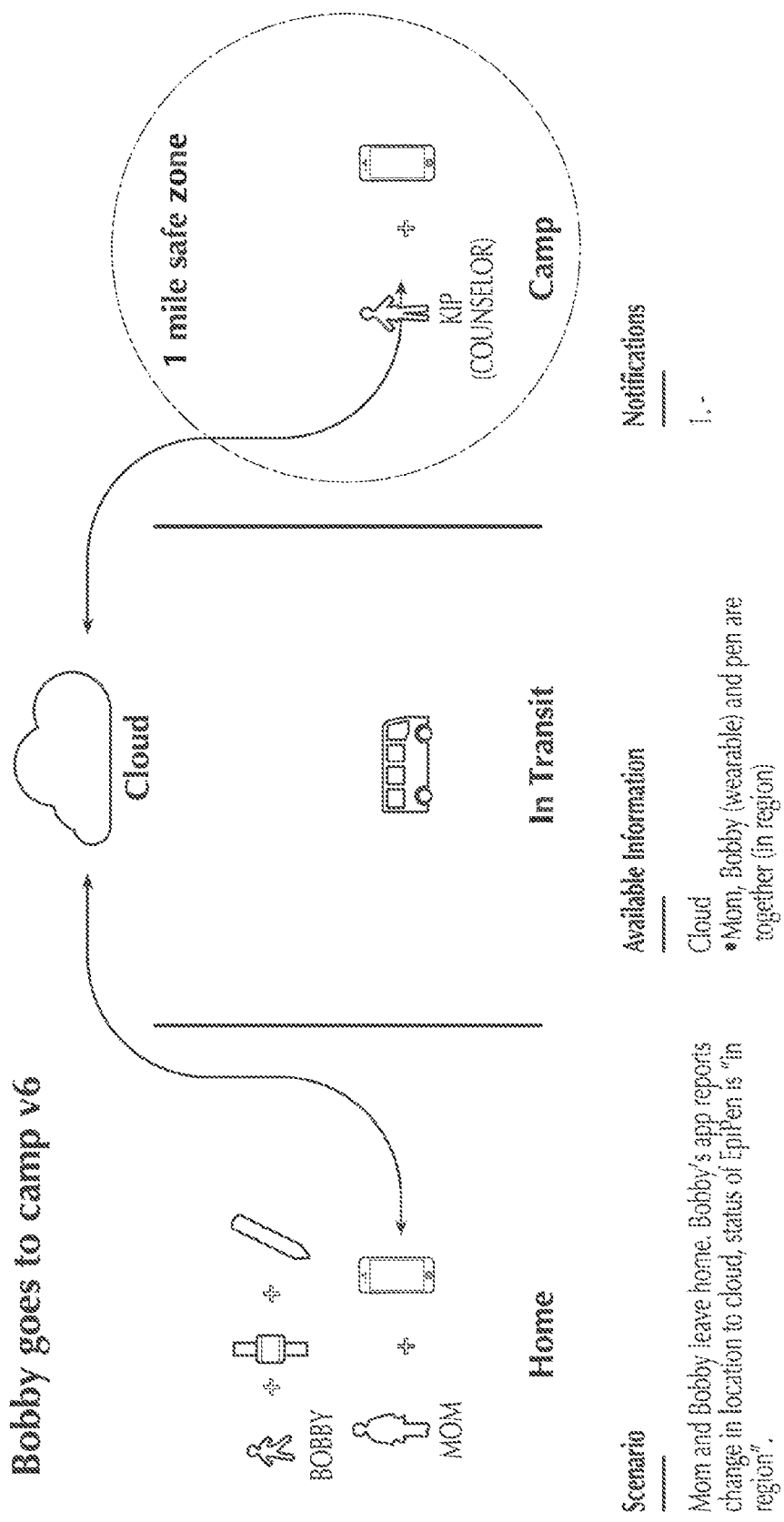
FIGS. 53-57 illustrate an exemplary system use scenario as described in Example 6.

Referring to FIG. 53, initially, the subject and the immediate family member are at home, and the level 1 caregiver is present at the destination. Accordingly, the sticker, wearable, and the first smartphone are connected and are in the same region. The first smartphone reports the "in region" status to the cloud server. Although the second smartphone is paired to the sticker but disconnected, the level 1 caregiver has not yet been granted responsibility of subject. In this case, the cloud server would allow the status reported by the first smartphone to override the status reported by the second smartphone. Based on the "in region" status, no notifications are made in the system.

Figure 54:
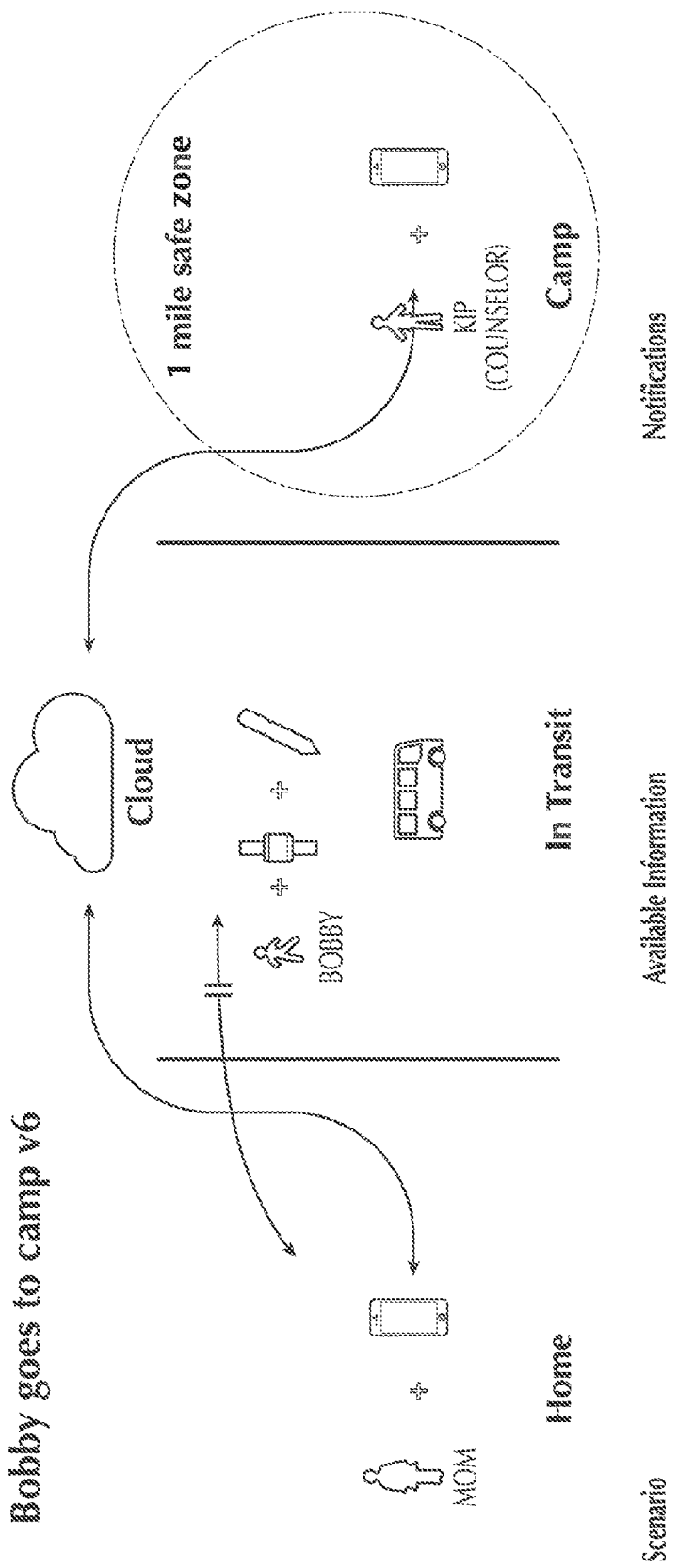

Next, referring to FIG. 54, the subject carries the sticker-attached epinephrine pen as well as the wearable with him and moves in transit away from the immediate family member. As the first smartphone loses connection with the sticker after the subject is more than about 30 feet away, the wearable remains connected with the sticker. The first smartphone determines that the epinephrine pen and wearable are out of the region and reports the "out of region" status to the cloud. The first smartphone further reports the location where it last co-localized with the sticker to the cloud. As a result, the first smartphone provides to immediate family member a notification that both subject and the epinephrine pen are out of region.

Figure 55:
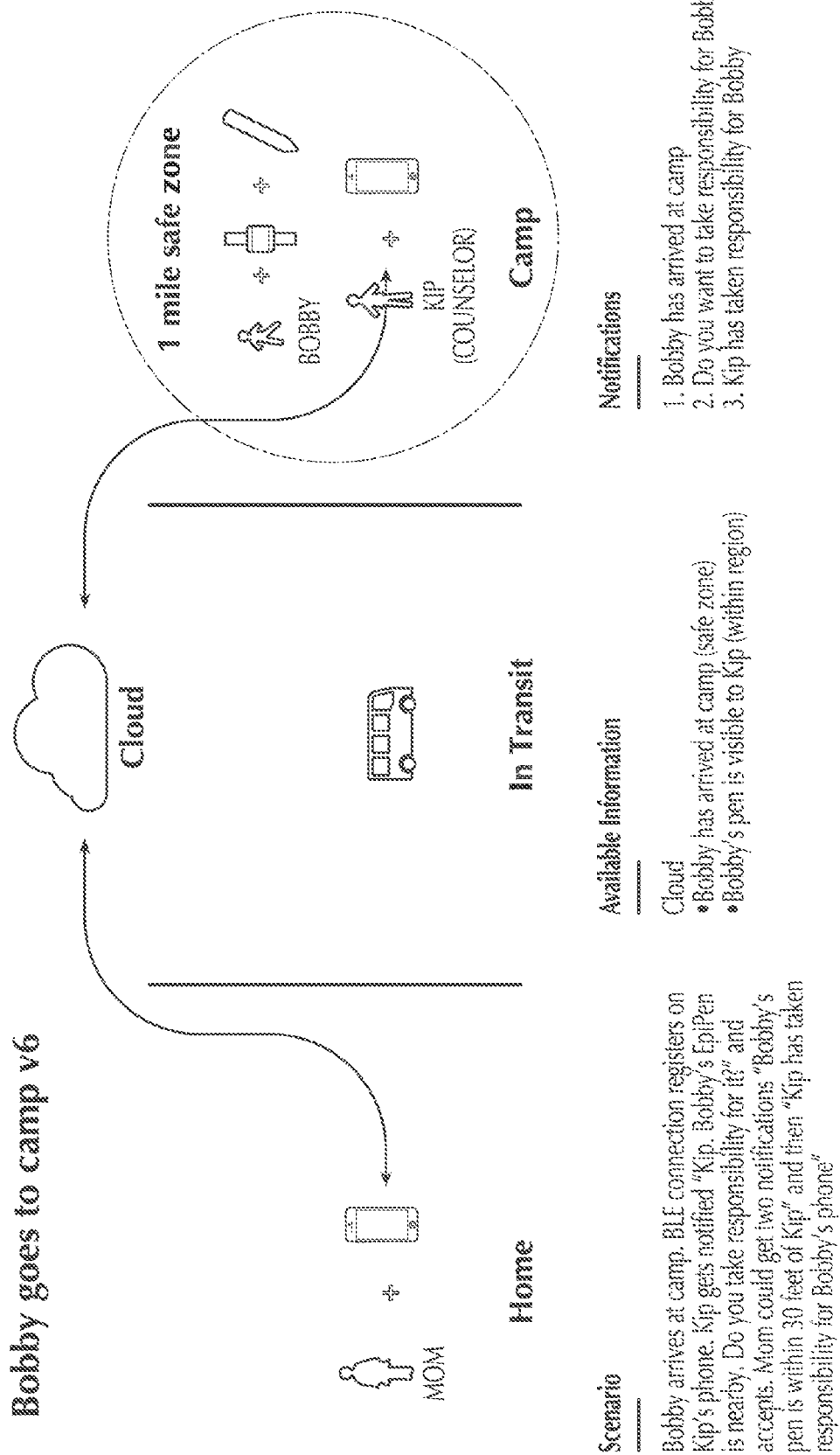

Referring to FIG. 55, the subject arrives at the destination carrying the sticker-attached epinephrine pen and wearing the wearable. Because the sticker is paired with the second smartphone, a connection between the sticker and the second smartphone would be established upon the arrival of subject at the destination. The level 1 caregiver would be given the option to accept the transferred responsibility to track the epinephrine pen. Upon acceptance of the responsibility, the second smartphone would report to the cloud that the epinephrine pen is "in region." Based on the "in region" statuses provided by the second smartphone, the immediate family member would be notified through the first smartphone that the subject and the level 1 caregiver are in region with the epinephrine pen.

Figure 56:
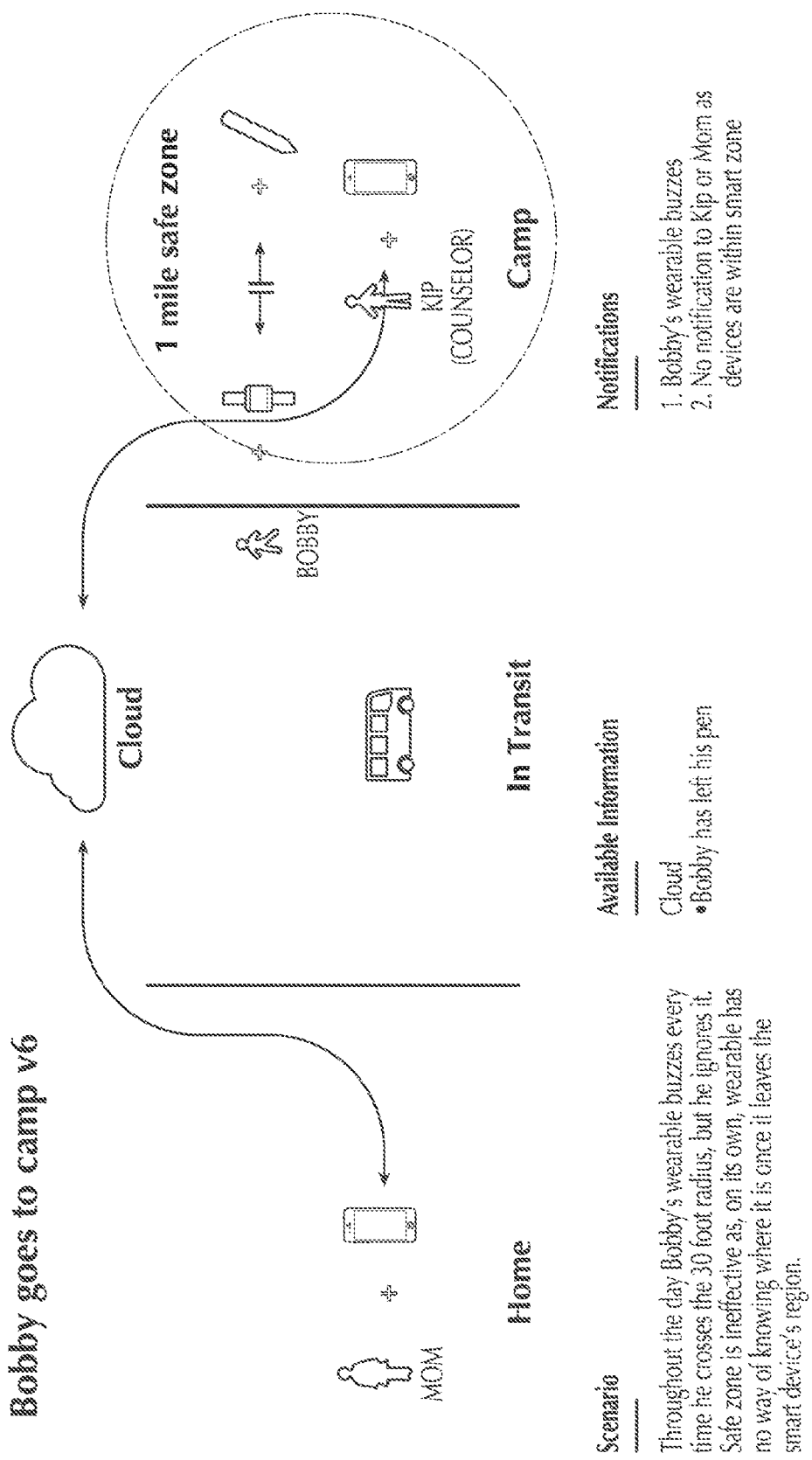

Referring to FIG. 56, the subject wearing the wearable is separated from the epinephrine pen attached to a sticker for more than 30 feet. The wearable loses connection with the sticker, which would trigger the wearable to vibrate. Such vibrations would notify subject that he has separated from the epinephrine pen. However, because wearable is not connected to the cloud, no additional notification would be provided to the first smartphone or the second smartphone. Indeed, because the second smartphone remains connected to the sticker, the second smartphone determines that the sticker device is still "in region." Accordingly, no additional notification would be provided to any smart devices.

Figure 57:
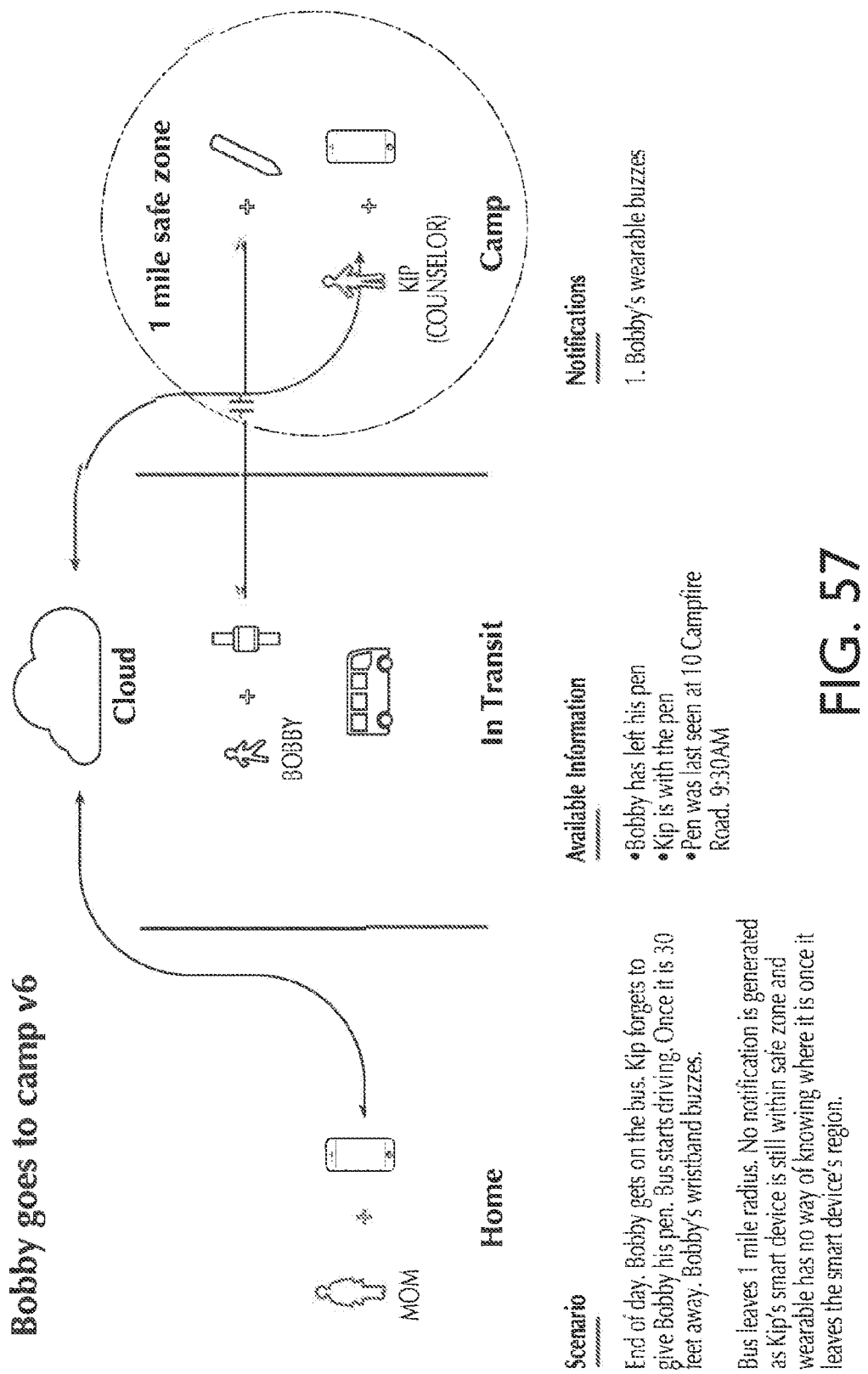

Finally, referring to FIG. 57, the subject wearing the wearable is in transit and is outside of the 1 mile safe zone as defined by the co-localization of the second smartphone and the sticker. The second smartphone is the only device that is connected with the sticker. The wearable continues to vibrate. Such vibrations would notify the subject that he has separated from the epinephrine pen. However, because the wearable is not connected to the cloud, no additional notification would be provided to the first smartphone or the second smartphone. Indeed, because the second smartphone remains connected to the sticker, the second smartphone determines that the sticker is still "in region." Accordingly, no additional notification would be provided to any smart devices.

Example 7

The use of a system comprising a the sticker attached to an epinephrine pen, two smartphones, and a the wearable by a subject, an immediate family member, and a level 1 caregiver is described. The smartphones are possessed by the immediate family member and the level 1 caregiver, respectively. In this scenario, the subject leaves home to a destination.

Figure 58:
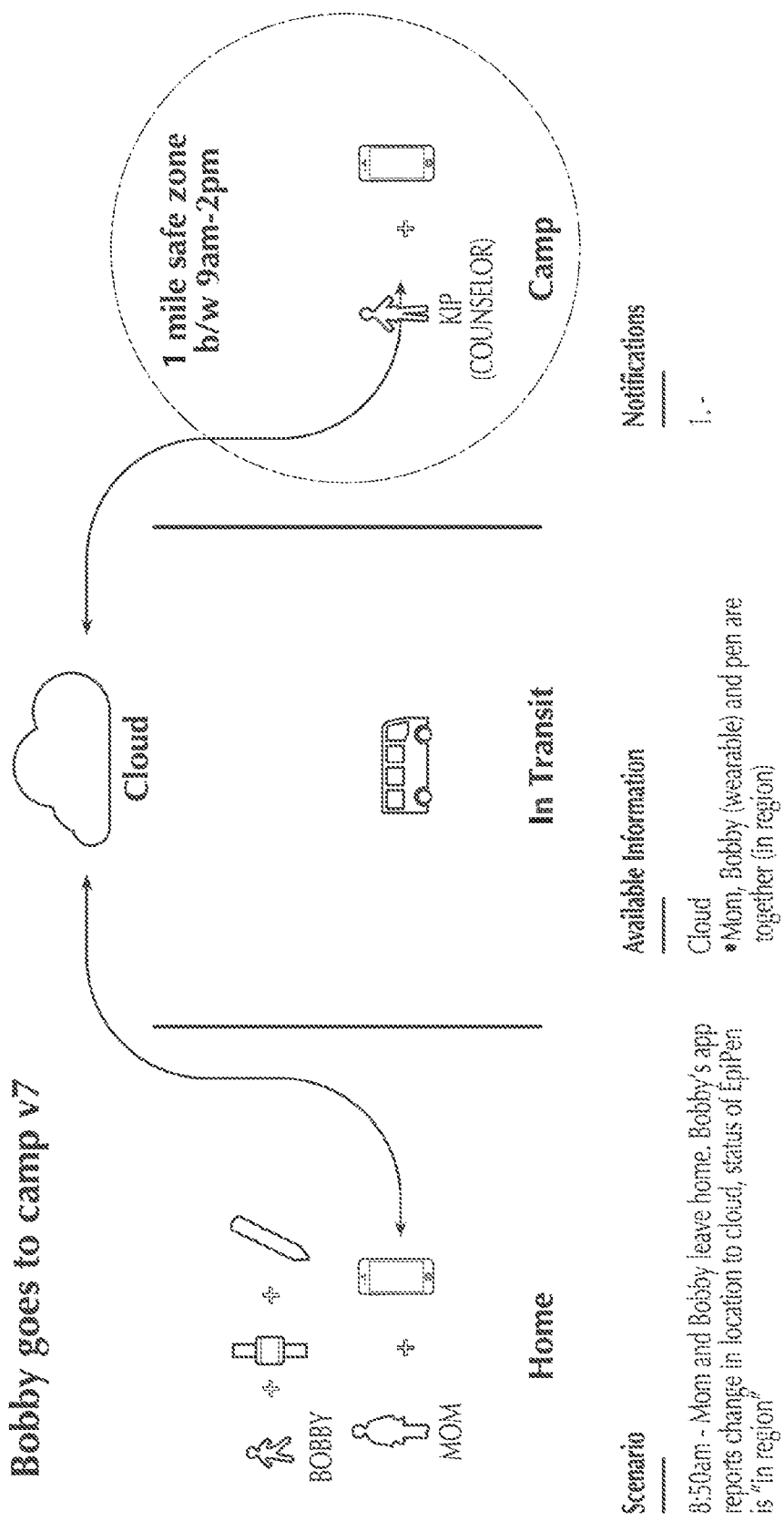

Referring to FIG. 58, initially, the subject and the immediate family member are at home, and the level 1 caregiver is present at the destination. Accordingly, the sticker, the wearable, and the first smartphone are connected and are in the same region. The first smartphone reports the "in region" status to the cloud server, Although the second smartphone is paired to the sticker but disconnected, the level 1 caregiver has not yet been granted responsibility of the subject. In this case, the cloud server would allow the status reported by the first smartphone to override the status reported by the second smartphone. Based on the "in region" status, no notifications are made in the system.

Figure 59:
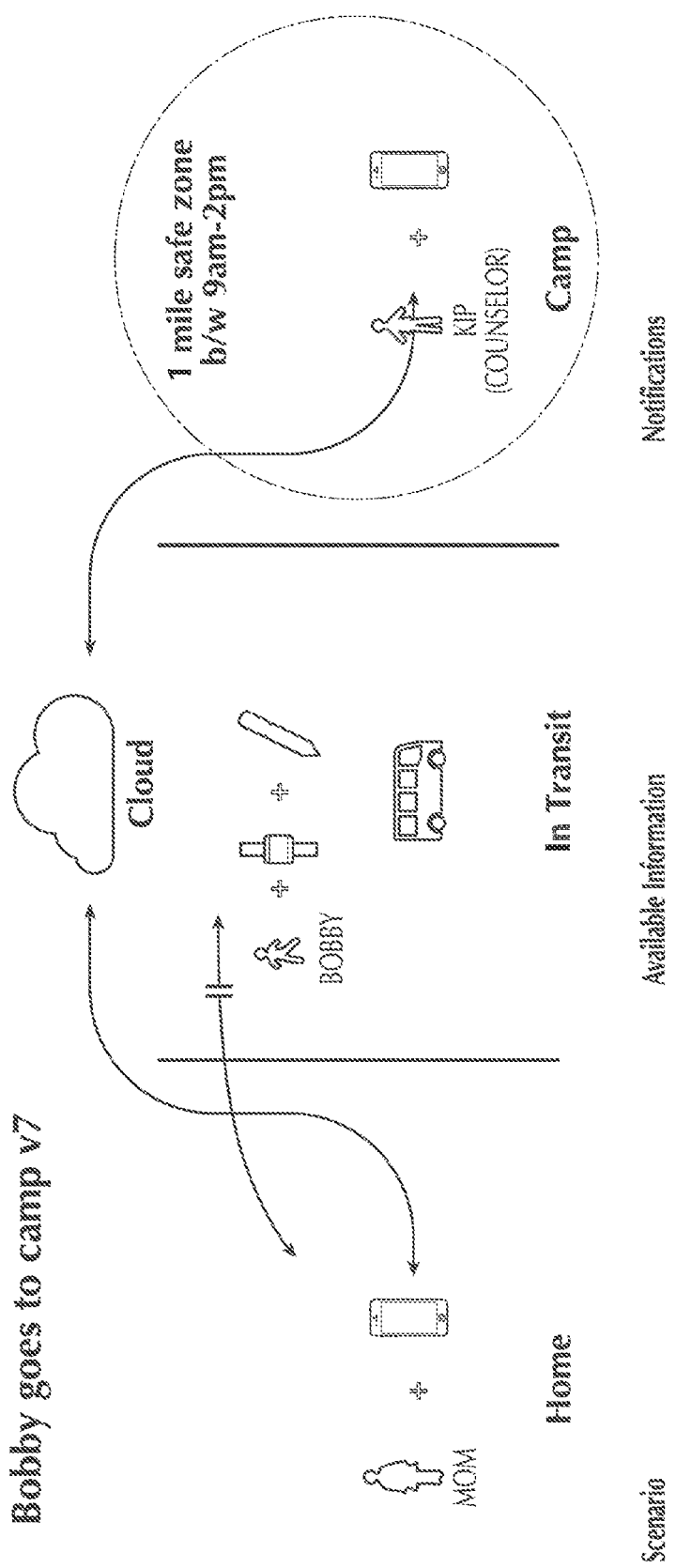

Next, referring to FIG. 59, subject carries the sticker-attached epinephrine pen as well as the wearable with him and moves in transit away from the immediate family member. As the first smartphone loses connection with the sticker after the subject is more than about 30 feet away, the wearable remains connected with the sticker. The first smartphone determines that the epinephrine pen and the wearable are out of the region and reports the "out of region" status to the cloud. The first smartphone further reports the location where it last co-localized with the sticker to the cloud. As a result, the first smartphone provides to the immediate family member a notification that both subject and the epinephrine pen are out of region.

Figure 60:
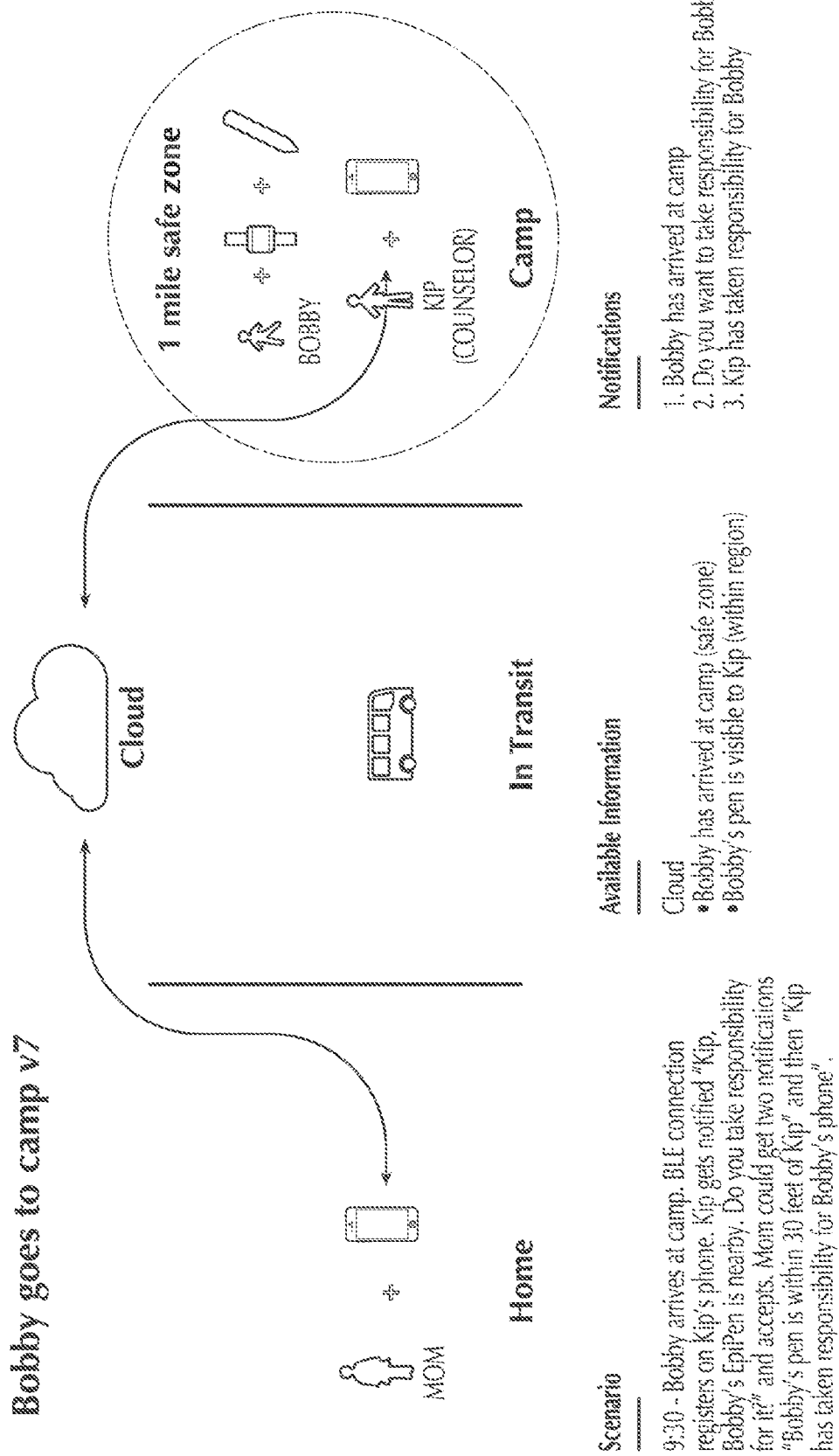

Referring to FIG. 60, the subject arrives at the destination carrying the sticker attached epinephrine pen and wearing the wearable. Because the sticker is paired with the second smartphone, a connection between the sticker and the second smartphone would be established upon the arrival of the subject at the destination. The level 1 caregiver would be given the option to accept the transferred responsibility to track the epinephrine pen. As a part of the responsibility transfer process, the level 1 caregiver would also define a safe time zone on the second smartphone. Upon acceptance of the responsibility, the second smartphone would report to the cloud that the epinephrine pen is "in region." Based on the "in region" statuses provided by the second smartphone, the immediate family member would be notified through the first smartphone that the subject and the level 1 caregiver are in region with the epinephrine pen. The safe time zone information would also be provided to the wearable.

Figure 61:
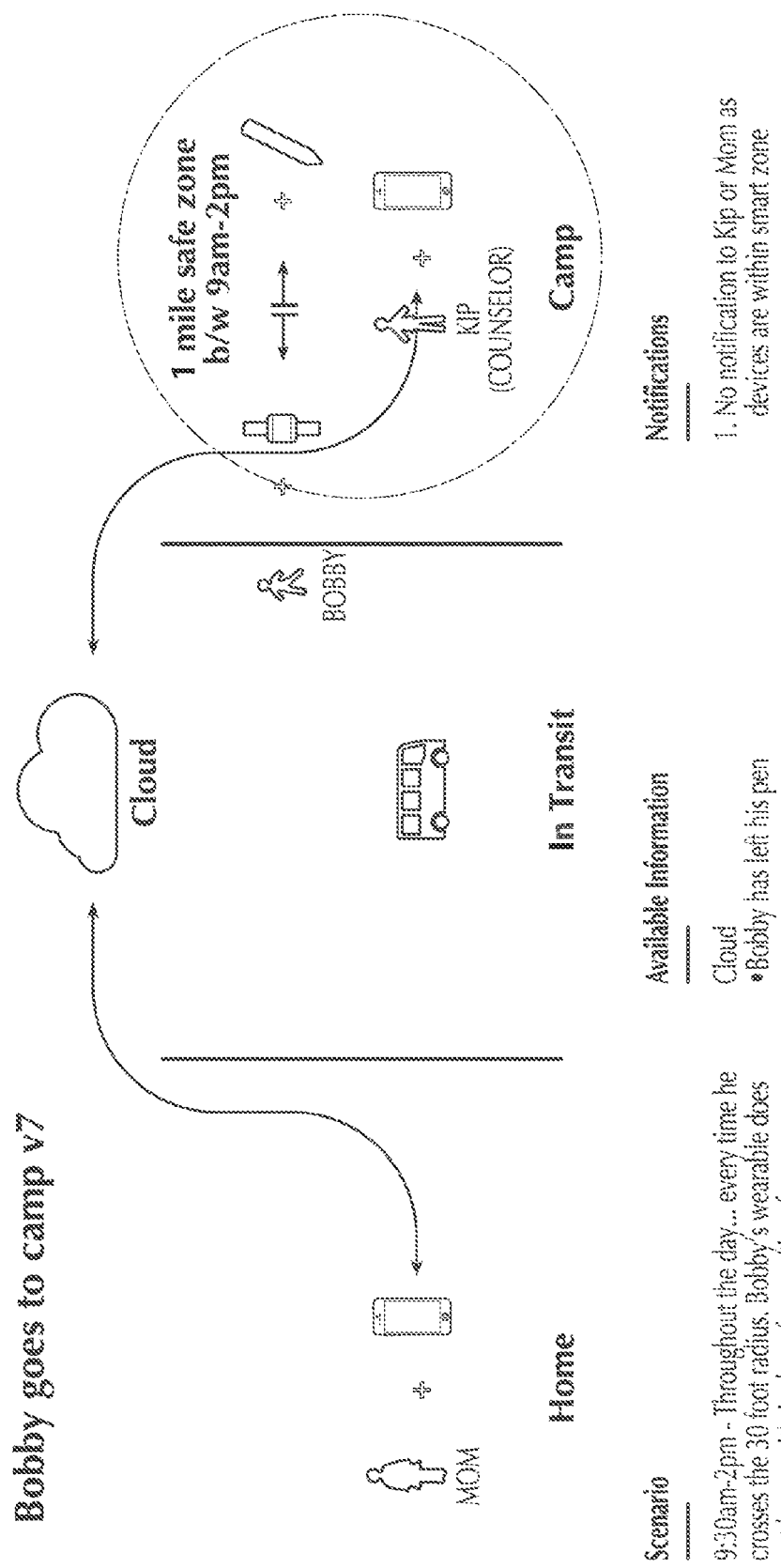

Referring to FIG. 61, the subject wearing the wearable is separated from the epinephrine pen attached to a the sticker for more than 30 feet during a safe time zone as previously defined. The wearable loses connection with the sticker, which would ordinarily trigger the wearable to vibrate. But the wearable would not vibrate during the safe time zone. The second smartphone remains connected to the sticker, hence, the second smartphone determines that the sticker device is still "in region". Accordingly, no additional notification would be provided to any smart devices.

Finally, referring to FIG. 62, the subject wearing the wearable is in transit. The safe time zone is expired and the subject is outside of the 1 mile safe zone as defined by the co-localization of the second smartphone and the sticker. As a result, the wearable vibrates. Such vibrations would notify the subject that he has separated from the epinephrine pen. Although the second smartphone remains connected to the sticker, the safe time zone has expired. Accordingly, the second smartphone determines that the subject is "out of region," and reports such status information to cloud server. As a result, the smartphones provide to all the team members a notification that the subject has left the epinephrine pen with the level 1 caretaker.

The invention claimed is:

1. A public base station, comprising:
a body;
a plurality of wells within the body, each well configured to receive a respective medication container;
a cover movably attached to the body, wherein the cover is movable between a closed position and an open position, wherein the cover in the closed position is configured to enclose within the base station one or more medication containers, each disposed within a respective well, and wherein the cover in the open position allows removal of a medication container disposed within one of the wells;
a programmable electronic processor disposed within the body;
one or more network interfaces operatively coupled to the processor;
a computer-readable storage medium operatively coupled to the processor and encoded with instructions that, when executed by the processor, cause the base station to participate in an electronic data network via at least one of the network interfaces;
one or more cover switches operatively coupled to the processor and configured to detect the position of the cover and to indicate to the processor the position of the cover;
a plurality of sensors, wherein:
each sensor is disposed within a respective one of the wells such that the sensor is able to detect the presence or absence of a medication container within the respective well; and each sensor is operatively coupled to the processor such that the sensor indicates to the processor the presence or absence of a medication container within the respective well in which the sensor is disposed;
wherein:
the one or more network interfaces comprise at least a first network interface that is capable of short-range wireless communication with a second device and a second network interface that is not the first network interface; the base station participates in the electronic data network via the second network interface; and the base station communicates via the electronic data network with a support infrastructure;
wherein the instructions comprise instructions that, when executed by the processor, cause the base station at least to:
attempt to establish a first connection, via the first network interface, with a portable wireless device;
consequent to establishing the first connection with the portable wireless device, transmit to the support infrastructure, via the electronic data network, first information indicating the establishment of the first connection with the portable wireless device;
subsequent to establishing the first connection with the portable wireless device, detect interruption of the first connection with the portable wireless device; and
consequent to detecting interruption of the first connection with the portable wireless device, transmit to the support infrastructure, via the electronic data network, second information indicating the interruption of the first connection with the portable wireless device.

2. The public base station of claim 1, wherein the instructions comprise instructions that, when executed by the processor, cause the base station at least to transmit, via the electronic data network to a support infrastructure, information comprising at least one of information regarding the position of the cover and information regarding the presence or absence of a medication container within one or more of the wells.

3. The public base station of claim 1, wherein the instructions comprise instructions that, when executed by the processor, cause the base station at least to: establish a connection, via the first network interface, with a sticker affixed to a medication container; receive first information from the sticker comprising information pertaining to the medication container; and transmit the first information to the support infrastructure via the electronic data network.

4. The public base station of claim 1, wherein the instructions comprise instructions that, when executed by the processor, cause the base station at least to: consequent to detecting interruption of the first connection with the portable wireless device, and prior to transmitting the second information to the support infrastructure, attempt to establish a second connection with the portable wireless device; and upon establishing the second connection with the portable wireless device within a preset time interval following detection of the interruption of the first connection with the portable wireless device, suppress transmission of the second information to the support infrastructure.

* * * * *